(12) United States Patent
Oda et al.

(10) Patent No.: US 8,378,114 B2
(45) Date of Patent: Feb. 19, 2013

(54) N-2-(HETERO)ARYLETHYLCARBOXAMIDE DERIVATIVE, AND PEST-CONTROLLING AGENT COMPRISING THE SAME

(75) Inventors: Masatsugu Oda, Kawachinagano (JP); Yoshihiro Matsuzaki, Kawachinagano (JP); Koji Tanaka, Kawachinagano (JP); Eiji Takizawa, Kawachinagano (JP); Motohiro Hasebe, Kawachinagano (JP); Nobutaka Kuroki, Kawachinagano (JP); Akiyuki Suwa, Kawachinagano (JP); Kenji Oshima, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 1033 days.

(21) Appl. No.: 12/225,361

(22) PCT Filed: Mar. 20, 2007

(86) PCT No.: PCT/JP2007/055726
§ 371 (c)(1),
(2), (4) Date: Dec. 19, 2008

(87) PCT Pub. No.: WO2007/108483
PCT Pub. Date: Sep. 27, 2007

(65) Prior Publication Data
US 2011/0136831 A1      Jun. 9, 2011

(30) Foreign Application Priority Data

Mar. 20, 2006 (JP) ................. 2006-077752
Oct. 30, 2006 (JP) ................. 2006-294810

(51) Int. Cl.
*C07D 211/72* (2006.01)
*C07D 213/56* (2006.01)
*A61K 31/4965* (2006.01)
*A01N 43/60* (2006.01)

(52) U.S. Cl. ............ 546/316; 514/255.06; 514/355; 514/433; 514/406; 544/407; 549/14; 548/374.1

(58) Field of Classification Search ............ 546/316; 544/407; 549/14; 514/255.06, 355, 433, 514/406
See application file for complete search history.

(56) References Cited

U.S. PATENT DOCUMENTS

| 4,957,533 | A | 9/1990 | Arnold et al. | |
|---|---|---|---|---|
| 5,399,564 | A | 3/1995 | Hackler et al. | |
| 6,194,458 | B1 | 2/2001 | Baker et al. | |
| 6,642,379 | B1 | 11/2003 | Furuya et al. | |
| 7,723,363 | B2 * | 5/2010 | Mansfield et al. | 514/341 |
| 2002/0151534 | A1 | 10/2002 | Ries et al. | |
| 2003/0153464 | A1 | 8/2003 | Nakamura et al. | |
| 2005/0164999 | A1 | 7/2005 | Foor et al. | |
| 2005/0234110 | A1 | 10/2005 | Mansfield et al. | |
| 2006/0052366 | A1 | 3/2006 | Mansfield et al. | |
| 2006/0246102 | A1 | 11/2006 | Mansfield et al. | |
| 2010/0222337 | A1 | 9/2010 | Nakamura et al. | |

FOREIGN PATENT DOCUMENTS

| CL | 3548-2000 | 12/2000 |
|---|---|---|
| CL | 199-2002 | 2/2002 |
| CL | 528-2003 | 3/2003 |
| EP | 0 340 709 | 11/1989 |
| EP | 1 428 817 | 6/2004 |
| JP | 1-151546 | 6/1989 |
| JP | 2001-302606 | 10/2001 |
| JP | 2001-342180 | 12/2001 |
| JP | 2001-342183 | 12/2001 |
| JP | 2004-269449 | 9/2004 |
| JP | 2005-179234 | 7/2005 |
| JP | 2005-535714 | 11/2005 |
| JP | 2007-210924 | 8/2007 |
| JP | 2008-100978 | 5/2008 |
| WO | 2004/016088 | 2/2004 |
| WO | 2004/074280 | 9/2004 |
| WO | 2005/014545 | 2/2005 |
| WO | 2005/058828 | 6/2005 |
| WO | 2005/058833 | 6/2005 |
| WO | 2005/085238 | 9/2005 |
| WO | 2006/016708 | 2/2006 |
| WO | 2007/060162 | 5/2007 |
| WO | 2007/060164 | 5/2007 |
| WO | 2007/060166 | 5/2007 |

OTHER PUBLICATIONS

International Search Report dated May 22, 2007 in the International (PCT) Application PCT/JP2007/055726 of which the present application is the U.S. National Stage. Supplementary European Search Report dated Oct. 21, 2010 issued in connection with European Patent Application No. 07 73 9169.

Bhabatosh Bhattacharya, "Isoquinoline Derivatives: Part XVIII—Formation of I- Alkyl-(or alkaryl or aryl)-3-methyl-7-chloro(or 5-chloro)-isoquinolines" Indian Journal of Chemistry, vol. 6, pp. 341-345, 1968.

G.A. White, "Substituted 2-Methylbenzanilides and Structurally Related Carboxamides: Inhibition of Complex II Activity in Mitochondria from a Wild-Type Strain and a Carboxin-Resistant Mutant Strain of *Ustilago maydis*" Pesticide Biochemistry and Physiology, vol. 34, No. 3, pp. 255-276, 1989.

(Continued)

*Primary Examiner* — Shirley V Gembeh
(74) *Attorney, Agent, or Firm* — Wenderoth, Lind & Ponack, L.L.P.

(57) ABSTRACT

An N-2-(hetero)arylethylcarboxamide derivative represented by the formula (I)

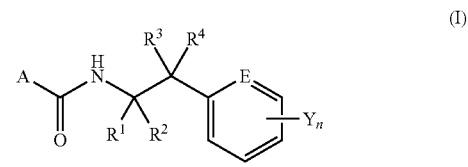

(I)

wherein $R^1$ and $R^2$ are each independently a hydrogen atom etc., $R^3$ and $R^4$ are each independently a hydrogen atom etc., each Y is independently a halogen atom; a $(C_1\text{-}C_6)$alkyl group optionally substituted by halogen atom(s) etc., n is an integer of 1 to 5, A is a specific substituted cyclic group, E is C—H; C—Y (Y is as defined above); or a nitrogen atom, a salt thereof, and a pest controlling agent containing the derivative or salt as an active ingredient show superior performance as compared to the prior art technique, and are is useful particularly as plant disease controlling agents or nematocides having a broad control spectrum at a low dose.

7 Claims, No Drawings

OTHER PUBLICATIONS

Database Beilstein accession No. 6216660, Jan. 1, 1989.

Eduardo Cortés Cortés et al., "Synthesis of Spectral Properties of 6,7-Dimethoxy-1-[(*ortho*; and *para*-R)-phenyl]-3,4-dihydroisoquinoline" Journal of Heterocyclic Chemistry, vol. 31, pp. 1425-1427, 1994.

Gema Rodriguez et al., "Dioxirane Epoxidation of 10-Membered-Ring Stilbene Lactams as Synthetic Precursors to Protoberberines" Journal of Organic Chemistry, vol. 64, No. 3, pp. 877-883, 1999.

Brian Hoffman et al., "Quantitative Structure-Activity Relationship Modeling of Dopamine $D_1$ Antagonists Using Comparative Molecular Field Analysis, Genetic Algorithms—Partial Least-Squares, and K Nearest Neighbor Methods" Journal of Medicinal Chemistry, vol. 42, pp. 3217-3226, 1999.

Carlos Lamas et al., "Synthesis of Isoquinoline Alkaloids through a 10-Membered Lactam Obtained by Radical Macrocyclisation" Tetrahedron Letters, vol. 33, pp. 5653-5654, 1992.

Chilean Office Action issued Feb. 16, 2009 in corresponding Chilean patent application No. 703-07.

Extended European Search Report issued Oct. 26, 2011 in corresponding European Application No. 11162239.5.

Taiwanese Search Report issued in Taiwanese Patent Application No. 096108514, received Jun. 21, 2012.

\* cited by examiner

N-2-(HETERO)ARYLETHYLCARBOXAMIDE DERIVATIVE, AND PEST-CONTROLLING AGENT COMPRISING THE SAME

TECHNICAL FIELD

The present invention relates to N-2-(hetero)arylethylcarboxamide derivatives, a salt thereof, and a pest controlling agent containing the compound as an active ingredient, particularly a plant disease controlling agent, nematocides and method of use thereof.

BACKGROUND ART

Conventionally, a certain kind of N-2-(hetero)arylethylcarboxamide derivative is known to have a fungicidal activity (e.g., see JP-A-1-151546, WO 04/016088, WO04/074280 or WO 06/016708).

DISCLOSURE OF THE INVENTION

However, phenethylcarboxamide derivatives described in JP-A-1-151546 hardly show activity against plant diseases at a practical level. While carboxamide derivatives described in WO 04/016088, WO04/074280 and WO 06/016708 may sometimes show a high fungicidal activity, they are problematic in that they do not have a sufficiently satisfactory fungicidal spectrum and the like. In the prior art, therefore, the efficacy and control spectrum of plant disease controlling agents are not entirely sufficient. In recent years, the burden on the global environment has been drawing attention, which gives rise to a demand for a compound for a plant disease controlling agent, which shows a broad control spectrum with a low dose.

The present inventors have conducted intensive studies in an attempt to solve the aforementioned problems and found that N-2-(hetero)arylethylcarboxamide derivatives represented by the formula (I) of the present invention and a salt thereof have a superior control efficacy and an extremely broad fungicidal spectrum as plant disease controlling agents, and a nematocidal activity as well, which resulted in the completion of the present invention.

Accordingly, the present invention relates to

[1] an $N^2$-(hetero)arylethylcarboxamide derivative represented by of the formula (I)

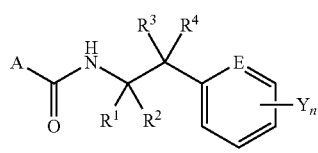

(I)

wherein $R^1$ and $R^2$ are each independently
a hydrogen atom; or
a $(C_1-C_3)$alkyl group,
or
$R^1$ and $R^2$ are optionally bonded to each other to form a $(C_3-C_6)$cycloalkane,
$R^3$ and $R^4$ are each independently
a hydrogen atom;
a halogen atom; or
a $(C_1-C_6)$alkyl group, or
$R^3$ and $R^4$ are optionally bonded to each other to form a $(C_3-C_6)$cycloalkane,
when A is a substituted cyclic group represented by the formula (A3), $R^3$ and $R^4$ optionally form an oxygen atom in combination,
each Y is independently
a halogen atom;
a cyano group;
a hydroxy group;
a $(C_1-C_6)$alkyl group optionally substituted by halogen atom(s);
a $(C_2-C_6)$alkenyl group optionally substituted by halogen atom(s);
a $(C_2-C_6)$alkynyl group optionally substituted by halogen atom(s);
a $(C_1-C_6)$alkoxy group optionally substituted by substituent(s) selected from the group consisting of a halogen atom and a $(C_1-C_6)$alkoxy group;
a $(C_2-C_6)$alkenyloxy group optionally substituted by halogen atom(s);
a $(C_2-C_6)$alkynyloxy group optionally substituted by halogen atom(s);
a $(C_1-C_6)$alkylthio group optionally substituted by halogen atom(s);
a $(C_1-C_6)$alkylsulfinyl group optionally substituted by halogen atom(s);
a $(C_1-C_6)$alkylsulfonyl group optionally substituted by halogen atom(s);
a $(C_1-C_6)$alkoxy-carbonyl group;
a $(C_1-C_6)$alkoxyimino$(C_1-C_3)$alkyl group;
a $(C_3-C_{30})$ trialkylsilyl group;
a phenyl group optionally substituted by one or more substituents selected from substituent group Z;
a phenoxy group optionally substituted by one or more substituents selected from substituent group Z; or
heterocyclyloxy group optionally substituted by one or more substituents selected from substituent group Z,
n is an integer of 1 to 5,
two Y's that become adjacent when n is an integer of 2 to 5 are optionally bonded to each other to show a $(C_3-C_5)$alkylene group;
a $(C_3-C_5)$alkenylene group;
a $(C_2-C_4)$alkyleneoxy group; or
a $(C_1-C_3)$alkylenedioxy group optionally substituted by halogen atom(s),
substituent group Z shows
a hydrogen atom;
a halogen atom;
a cyano group;
a $(C_1-C_6)$alkyl group optionally substituted by halogen atom(s);
a $(C_2-C_6)$alkenyl group optionally substituted by halogen atom(s);
a $(C_2-C_6)$alkynyl group optionally substituted by halogen atom(s);
a $(C_1-C_6)$alkoxy group optionally substituted by halogen atom(s);
a $(C_2-C_6)$alkenyloxy group optionally substituted by halogen atom(s);
a $(C_2-C_6)$alkynyloxy group optionally substituted by halogen atom(s);
a $(C_1-C_6)$alkylthio group optionally substituted by halogen atom(s);
a $(C_1-C_6)$alkylsulfinyl group optionally substituted by halogen atom(s);
a $(C_1-C_6)$alkylsulfonyl group optionally substituted by halogen atom(s);
a $(C_1-C_6)$alkoxy-carbonyl group;
a $(C_1-C_6)$ alkoxyimino$(C_1-C_3)$ alkyl group; or
a carbamoyl group, A is a substituted cyclic group selected from the group consisting of the formulas (A1) to (A10),

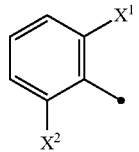 (A1)

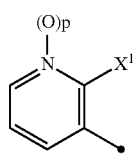 (A2)

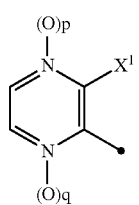 (A3)

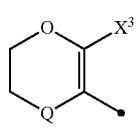 (A4)

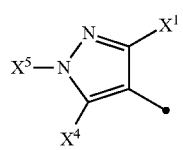 (A5)

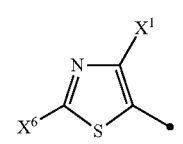 (A6)

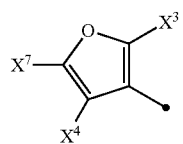 (A7)

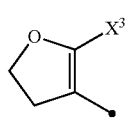 (A8)

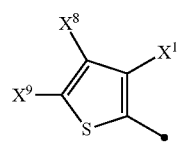 (A9)

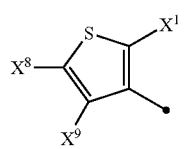 (A10)

wherein $X^1$ is
a halogen atom;
a $(C_1-C_3)$alkyl group optionally substituted by halogen atom(s);
a $(C_1-C_3)$alkoxy group optionally substituted by halogen atom(s);
or
a $(C_1-C_3)$alkylthio group optionally substituted by halogen atom(s),
$X^2$ is
a hydrogen atom; or
a halogen atom,
$X^3$ is a $(C_1-C_3)$alkyl group optionally substituted by halogen atom(s),
$X^4$, $X^7$, $X^8$ and $X^9$ are each independently
a hydrogen atom;
a halogen atom; or
a $(C_1-C_3)$alkyl group optionally substituted by halogen atom(s),
$X^5$ is
a hydrogen atom; or
a $(C_1-C_3)$alkyl group optionally substituted by halogen atom(s),
$X^6$ is
a hydrogen atom;
an amino group;
a mono$(C_1-C_3)$ alkylamino group;
a di$(C_1-C_3)$alkylamino group;
a halogen atom; or
a $(C_1-C_3)$alkyl group optionally substituted by halogen atom(s),
Q is
an oxygen atom;
a sulfur atom;
—SO$_2$— or
—CH$_2$—,
p and q are each independently 0 or 1, and
E is
C—H;
C—Y (Y is as defined above); or
a nitrogen atom,
provided that
(1) when E is a nitrogen atom, A is a substituted cyclic group represented by the formula (A3), and
(2) 2,6-dichloro-N-[2-{3-(trifluoromethyl)phenyl}ethyl]benzamide is excluded, or a salt thereof;
[2] the N-2-(hetero)arylethylcarboxamide derivative of the above-mentioned [1], wherein E is C—H or C—Y (Y is as defined in the above-mentioned [1]),
or a salt thereof;
[3] the N-2-(hetero)arylethylcarboxamide derivative of the above-mentioned [1] or [2], wherein
A is a substituted cyclic group represented by the formula (A1),
or a salt thereof;
[4] the N-2-(hetero)arylethylcarboxamide derivative of any one of the above-mentioned [1] to [3], wherein
A is a substituted cyclic group represented by the formula (A1),
E is
C—H or
C—Y (Y is as defined below),
$R^1$ and $R^2$ are each independently
a hydrogen atom; or
a $(C_1-C_3)$alkyl group, or
$R^1$ and $R^2$ are optionally bonded to each other to form a $(C_3-C_6)$cycloalkane, $R^3$ and $R^4$ are each independently
a hydrogen atom;
a halogen atom; or
a ($C_1$-$C_6$)alkyl group, or
$R^3$ and $R^4$ are optionally bonded to each other to form
a ($C_3$-$C_6$)cycloalkane,
each Y is independently
a halogen atom;
a cyano group;
a hydroxy group;
a ($C_1$-$C_6$)alkyl group optionally substituted by halogen atom(s);
a ($C_1$-$C_6$)alkoxy group optionally substituted by substituent(s) selected from the group consisting of a halogen atom and a ($C_1$-$C_6$)alkoxy group;
a ($C_2$-$C_6$)alkenyloxy group optionally substituted by halogen atom(s);
a ($C_1$-$C_6$)alkylthio group optionally substituted by halogen atom(s);
a ($C_1$-$C_6$)alkylsulfinyl group optionally substituted by halogen atom(s);
a ($C_1$-$C_6$)alkylsulfonyl group optionally substituted by halogen atom(s);
a phenyl group optionally substituted by the same or different one or more substituents selected from the group consisting of
  (i) a halogen atom,
  (ii) a ($C_1$-$C_6$)alkyl group optionally substituted by halogen atom(s) and
  (iii) a ($C_1$-$C_6$)alkoxy group optionally substituted by halogen atom(s);
a phenoxy group optionally substituted by the same or different one or more substituents selected from the group consisting of
  (i) a halogen atom,
  (ii) a ($C_1$-$C_6$)alkyl group optionally substituted by halogen atom(s) and
  (iii) a ($C_1$-$C_6$)alkoxy group optionally substituted by halogen atom(s); or
a heterocyclyloxy group optionally substituted by the same or different one or more substituents selected from the group consisting of
  (i) a halogen atom,
  (ii) a ($C_1$-$C_6$)alkyl group optionally substituted by halogen atom(s) and
  (iii) a ($C_1$-$C_6$)alkoxy group optionally substituted by halogen atom(s),
n is an integer of 1 to 3,
two Y's that become adjacent when n is an integer of 2 or 3 are optionally bonded to each other to show
a ($C_3$-$C_5$)alkylene group;
a ($C_3$-$C_5$)alkenylene group;
a ($C_2$-$C_4$)alkyleneoxy group; or
a ($C_1$-$C_3$)alkylenedioxy group optionally substituted by halogen atom(s),
$X^1$ is
a halogen atom;
a ($C_1$-$C_3$)alkyl group optionally substituted by halogen atom(s);
a ($C_1$-$C_3$)alkoxy group optionally substituted by halogen atom(s); or
a ($C_1$-$C_3$)alkylthio group optionally substituted by halogen atom(s), and
$X^2$ is
a hydrogen atom; or
a halogen atom,
or a salt thereof;

[5] the N-2-(hetero)arylethylcarboxamide derivative of the above-mentioned [1] or [2], wherein
A is a substituted cyclic group represented by the formula (A2),
or a salt thereof;
[6] the N-2-(hetero)arylethylcarboxamide derivative of any one of the above-mentioned [1], [2] and [5], wherein
A is a substituted cyclic group represented by the formula (A2),
E is
C—H or
C—Y (Y is as defined below),
$R^1$ and $R^2$ are each independently
a hydrogen atom; or
a ($C_1$-$C_3$)alkyl group, or
$R^1$ and $R^2$ are optionally bonded to each other to form
a ($C_3$-$C_6$)cycloalkane,
$R^3$ and $R^4$ are each independently
a hydrogen atom;
a halogen atom; or
a ($C_1$-$C_6$)alkyl group, or
$R^3$ and $R^4$ are optionally bonded to each other to form
a ($C_3$-$C_6$)cycloalkane,
each Y is independently
a halogen atom;
a cyano group;
a hydroxy group;
a ($C_1$-$C_6$)alkyl group optionally substituted by halogen atom(s);
a ($C_1$-$C_6$)alkoxy group optionally substituted by substituent(s) selected from the group consisting of a halogen atom and a ($C_1$-$C_6$)alkoxy group;
a ($C_2$-$C_6$)alkenyloxy group optionally substituted by halogen atom(s);
a ($C_1$-$C_6$)alkylthio group optionally substituted by halogen atom(s);
a ($C_1$-$C_6$)alkylsulfinyl group optionally substituted by halogen atom(s);
a ($C_1$-$C_6$)alkylsulfonyl group optionally substituted by halogen atom(s);
a phenyl group optionally substituted by the same or different one or more substituents selected from the group consisting of
  (i) a halogen atom,
  (ii) a ($C_1$-$C_6$)alkyl group optionally substituted by halogen atom(s) and
  (iii) a ($C_1$-$C_6$)alkoxy group optionally substituted by halogen atom(s);
a phenoxy group optionally substituted by the same or different one or more substituents selected from the group consisting of
  (i) a halogen atom,
  (ii) a ($C_1$-$C_6$)alkyl group optionally substituted by halogen atom(s) and
  (iii) a ($C_1$-$C_6$)alkoxy group optionally substituted by halogen atom(s); or
a heterocyclyloxy group optionally substituted by the same or different one or more substituents selected from the group consisting of
  (i) a halogen atom,
  (ii) a ($C_1$-$C_6$)alkyl group optionally substituted by halogen atom(s) and
  (iii) a ($C_1$-$C_6$)alkoxy group optionally substituted by halogen atom(s),
n is an integer of 1 to 3,
two Y's that become adjacent when n is an integer of 2 or 3 are optionally bonded to each other to show a ($C_3$-$C_5$)alkylene group;
a ($C_3$-$C_5$)alkenylene group;
a ($C_2$-$C_4$)alkyleneoxy group; or
a ($C_1$-$C_3$)alkylenedioxy group optionally substituted by halogen atom(s),
$X^1$ is
a halogen atom; or
a ($C_1$-$C_3$)alkyl group optionally substituted by halogen atom(s), and
p is 0,
or a salt thereof;
[7] the N-2-(hetero)arylethylcarboxamide derivative of the above-mentioned [1] or [2], wherein
A is a substituted cyclic group represented by the formula (A3),
or a salt thereof;
[8] the N-2-(hetero)arylethylcarboxamide derivative of the above-mentioned [1] or [7], wherein
A is a substituted cyclic group represented by the formula (A3),
E is
C—H;
C—Y (Y is as defined below) or
a nitrogen atom,
$R^1$ and $R^2$ are each independently
a hydrogen atom; or
a ($C_1$-$C_3$)alkyl group, or
$R^1$ and $R^2$ are optionally bonded to each other to form
a ($C_3$-$C_6$)cycloalkane,
$R^3$ and $R^4$ are each independently
a hydrogen atom;
a halogen atom; or
a ($C_1$-$C_6$)alkyl group,
$R^3$ and $R^4$ are optionally bonded to each other to form
a ($C_3$-$C_6$)cycloalkane, or
$R^3$ and $R^4$ optionally form an oxygen atom in combination,
each Y is independently
a halogen atom;
a cyano group;
a hydroxy group;
a ($C_1$-$C_6$)alkyl group optionally substituted by halogen atom(s);
a ($C_1$-$C_6$)alkoxy group optionally substituted by halogen atom(s);
a ($C_2$-$C_6$)alkenyloxy group optionally substituted by halogen atom(s);
a ($C_1$-$C_6$)alkylthio group optionally substituted by halogen atom(s);
a ($C_1$-$C_6$)alkylsulfinyl group optionally substituted by halogen atom(s);
a ($C_1$-$C_6$)alkylsulfonyl group optionally substituted by halogen atom(s);
a phenyl group optionally substituted by the same or different one or more substituents selected from the group consisting of
  (i) a halogen atom,
  (ii) a ($C_1$-$C_6$)alkyl group optionally substituted by halogen atom(s) and
  (iii) a ($C_1$-$C_6$)alkoxy group optionally substituted by halogen atom(s);
a phenoxy group optionally substituted by the same or different one or more substituents selected from the group consisting of
  (i) a halogen atom,
  (ii) a ($C_1$-$C_6$)alkyl group optionally substituted by halogen atom(s) and
  (iii) a ($C_1$-$C_6$)alkoxy group optionally substituted by halogen atom(s); or
a heterocyclyloxy group optionally substituted by the same or different one or more substituents selected from the group consisting of
  (i) a halogen atom,
  (ii) a ($C_1$-$C_6$)alkyl group optionally substituted by halogen atom(s) and
  (iii) a ($C_1$-$C_6$)alkoxy group optionally substituted by halogen atom(s),
n is an integer of 1 to 3,
two Y's that become adjacent when n is an integer of 2 or 3 are optionally bonded to each other to show
a ($C_3$-$C_5$)alkylene group;
a ($C_3$-$C_5$)alkenylene group;
a ($C_2$-$C_4$)alkyleneoxy group; or
a ($C_1$-$C_3$)alkylenedioxy group optionally substituted by halogen atom(s),
$X^1$ is
a halogen atom; or
a ($C_1$-$C_3$)alkyl group optionally substituted by halogen atom(s), and
p and q are each 0,
or a salt thereof;
[9] the N-2-(hetero)arylethylcarboxamide derivative of the above-mentioned [8], wherein
E is C—H or C—Y (Y is as defined in the above-mentioned [8]),
or a salt thereof;
[10] the N-2-(hetero)arylethylcarboxamide derivative of the above-mentioned [1] or [2], wherein
A is a substituted cyclic group represented by the formula (A4),
or a salt thereof;
[11] the N-2-(hetero)arylethylcarboxamide derivative of any one of the above-mentioned [1], [2] and [10], wherein
A is a substituted cyclic group represented by the formula (A4),
E is
C—H or
C—Y (Y is as defined below),
$R^1$ and $R^2$ are each independently
a hydrogen atom; or
a ($C_1$-$C_3$)alkyl group,
$R^3$ and $R^4$ are each independently
a hydrogen atom;
a halogen atom; or
a ($C_1$-$C_6$)alkyl group, or
$R^3$ and $R^4$ are optionally bonded to each other to form
a ($C_3$-$C_6$)cycloalkane,
each Y is independently
a halogen atom;
a cyano group;
a ($C_1$-$C_6$)alkyl group optionally substituted by halogen atom(s);
a ($C_1$-$C_6$)alkoxy group optionally substituted by halogen atom(s);
a ($C_1$-$C_6$)alkylthio group optionally substituted by halogen atom(s);
a ($C_1$-$C_6$)alkylsulfinyl group optionally substituted by halogen atom(s);
a ($C_1$-$C_6$)alkylsulfonyl group optionally substituted by halogen atom(s);
a phenyl group optionally substituted by the same or different one or more substituents selected from the group consisting of (i) a halogen atom,
(ii) a ($C_1$-$C_6$)alkyl group optionally substituted by halogen atom(s) and
(iii) a ($C_1$-$C_6$)alkoxy group optionally substituted by halogen atom(s); or
a phenoxy group optionally substituted by the same or different one or more substituents selected from the group consisting of
(i) a halogen atom,
(ii) a ($C_1$-$C_6$)alkyl group optionally substituted by halogen atom(s) and
(iii) a ($C_1$-$C_6$)alkoxy group optionally substituted by halogen atom(s),
n is an integer of 1 to 3,
two Y's that become adjacent when n is an integer of 2 or 3 are optionally bonded to each other to show
a ($C_3$-$C_5$)alkylene group;
a ($C_3$-$C_5$)alkenylene group;
a ($C_2$-$C_4$)alkyleneoxy group; or
a ($C_1$-$C_3$)alkylenedioxy group optionally substituted by halogen atom(s),
$X^3$ is a ($C_1$-$C_3$)alkyl group optionally substituted by halogen atom(s), and
Q is a sulfur atom,
or a salt thereof;
[12] the N-2-(hetero)arylethylcarboxamide derivative of the above-mentioned [1] or [2], wherein
A is a substituted cyclic group represented by the formula (A5),
or a salt thereof;
[13] the N-2-(hetero)arylethylcarboxamide derivative of any one of the above-mentioned [1], [2] and [12], wherein
A is substituted cyclic group represented by the formula (A5),
E is
C—H or
C—Y (Y is as defined below),
$R^1$ and $R^2$ are each independently
a hydrogen atom; or
a ($C_1$-$C_3$)alkyl group,
$R^3$ and $R^4$ are each independently
a hydrogen atom;
a halogen atom; or
a ($C_1$-$C_6$)alkyl group, or
$R^3$ and $R^4$ are optionally bonded to each other to form
a ($C_3$-$C_6$)cycloalkane,
each Y is independently
a halogen atom;
a cyano group;
a ($C_1$-$C_6$)alkyl group optionally substituted by halogen atom(s);
a ($C_1$-$C_6$)alkoxy group optionally substituted by halogen atom(s);
a ($C_1$-$C_6$)alkylthio group optionally substituted by halogen atom(s);
a ($C_1$-$C_6$)alkylsulfinyl group optionally substituted by halogen atom(s);
a ($C_1$-$C_6$)alkylsulfonyl group optionally substituted by halogen atom(s);
a phenyl group optionally substituted by the same or different one or more substituents selected from the group consisting of
(i) a halogen atom,
(ii) a ($C_1$-$C_6$)alkyl group optionally substituted by halogen atom(s) and
(iii) a ($C_1$-$C_6$)alkoxy group optionally substituted by halogen atom(s); or
a phenoxy group optionally substituted by the same or different one or more substituents selected from the group consisting of
(i) a halogen atom,
(ii) a ($C_1$-$C_6$)alkyl group optionally substituted by halogen atom(s) and
(iii) a ($C_1$-$C_6$)alkoxy group optionally substituted by halogen atom(s),
n is an integer of 1 to 3,
two Y's that become adjacent when n is an integer of 2 or 3 are optionally bonded to each other to show
a ($C_3$-$C_5$)alkylene group;
a ($C_3$-$C_5$) alkenylene group;
a ($C_2$-$C_4$)alkyleneoxy group; or
a ($C_1$-$C_3$)alkylenedioxy group optionally substituted by halogen atom(s),
$X^1$ is
a halogen atom; or
a ($C_1$-$C_3$)alkyl group optionally substituted by halogen atom(s),
$X^4$ is
a hydrogen atom;
a halogen atom; or
a ($C_1$-$C_3$)alkyl group optionally substituted by halogen atom(s), and
$X^5$ is
a hydrogen atom; or
a ($C_1$-$C_3$)alkyl group optionally substituted by halogen atom(s),
or a salt thereof;
[14] the N-2-(hetero)arylethylcarboxamide derivative of the above-mentioned [1] or [2], wherein
A is a substituted cyclic group represented by the formula (A6),
or a salt thereof;
[15] the N-2-(hetero)arylethylcarboxamide derivative of any one of the above-mentioned [1], [2] and [14], wherein
A is a substituted cyclic group represented by the formula (A6),
E is
C—H or
C—Y (Y is as defined below),
$R^1$ and $R^2$ are each independently
a hydrogen atom; or
a ($C_1$-$C_3$)alkyl group,
$R^3$ and $R^4$ are each independently
a hydrogen atom;
a halogen atom; or
a ($C_1$-$C_6$)alkyl group, or
$R^3$ and $R^4$ are optionally bonded to each other to form
a ($C_3$-$C_6$)cycloalkane,
each Y is independently
a halogen atom;
a cyano group;
a ($C_1$-$C_6$)alkyl group optionally substituted by halogen atom(s);
a ($C_1$-$C_6$)alkoxy group optionally substituted by halogen atom(s);
a ($C_1$-$C_6$)alkylthio group optionally substituted by halogen atom(s);
a ($C_1$-$C_6$)alkylsulfinyl group optionally substituted by halogen atom(s);
a ($C_1$-$C_6$)alkylsulfonyl group optionally substituted by halogen atom(s);
a phenyl group optionally substituted by the same or different one or more substituents selected from the group consisting of (i) a halogen atom,
(ii) a $(C_1-C_6)$alkyl group optionally substituted by halogen atom(s) and
(iii) a $(C_1-C_6)$alkoxy group optionally substituted by halogen atom(s); or
a phenoxy group optionally substituted by the same or different one or more substituents selected from the group consisting of
(i) a halogen atom,
(ii) a $(C_1-C_6)$alkyl group optionally substituted by halogen atom(s) and
(iii) a $(C_1-C_6)$alkoxy group optionally substituted by halogen atom(s),
n is an integer of 1 to 3,
two Y's that become adjacent when n is an integer of 2 or 3 are optionally bonded to each other to show
a $(C_3-C_5)$alkylene group;
a $(C_3-C_5)$alkenylene group;
a $(C_2-C_4)$alkyleneoxy group; or
a $(C_1-C_3)$alkylenedioxy group optionally substituted by halogen atom(s),
$X^1$ is
a halogen atom; or
a $(C_1-C_3)$alkyl group optionally substituted by halogen atom(s), and
$X^6$ is
a hydrogen atom;
an amino group;
a mono$(C_1-C_3)$ alkylamino group;
a di$(C_1-C_3)$alkylamino group;
a halogen atom; or
a $(C_1-C_3)$alkyl group optionally substituted by halogen atom(s),
or a salt thereof;
[16] the N-2-(hetero)arylethylcarboxamide derivative of the above-mentioned [1] or [2], wherein
A is a substituted cyclic group represented by the formula (A7),
or a salt thereof;
[17] the N-2-(hetero)arylethylcarboxamide derivative of any one of the above-mentioned [1], [2] and [16], wherein
A is a substituted cyclic group represented by the formula (A7),
E is
C—H or
C—Y (Y is as defined below),
$R^1$ and $R^2$ are each independently
a hydrogen atom; or
a $(C_1-C_3)$alkyl group,
$R^3$ and $R^4$ are each independently
a hydrogen atom;
a halogen atom; or
a $(C_1-C_6)$alkyl group, or
$R^3$ and $R^4$ are optionally bonded to each other to form
a $(C_3-C_6)$cycloalkane,
each Y is independently
a halogen atom;
a cyano group;
a $(C_1-C_6)$alkyl group optionally substituted by halogen atom(s);
a $(C_1-C_6)$alkoxy group optionally substituted by halogen atom(s);
a $(C_1-C_6)$alkylthio group optionally substituted by halogen atom(s);
a $(C_1-C_6)$alkylsulfinyl group optionally substituted by halogen atom(s);
a $(C_1-C_6)$alkylsulfonyl group optionally substituted by halogen atom(s);
a phenyl group optionally substituted by the same or different one or more substituents selected from the group consisting of
(i) a halogen atom,
(ii) a $(C_1-C_6)$alkyl group optionally substituted by halogen atom(s) and
(iii) a $(C_1-C_6)$alkoxy group optionally substituted by halogen atom(s); or
a phenoxy group optionally substituted by the same or different one or more substituents selected from the group consisting of
(i) a halogen atom,
(ii) a $(C_1-C_6)$alkyl group optionally substituted by halogen atom(s) and
(iii) a $(C_1-C_6)$alkoxy group optionally substituted by halogen atom(s),
n is an integer of 1 to 3,
two Y's that become adjacent when n is an integer of 2 or 3 are optionally bonded to each other to show
a $(C_3-C_5)$alkylene group;
a $(C_3-C_5)$ alkenylene group;
a $(C_2-C_4)$alkyleneoxy group; or
a $(C_1-C_3)$alkylenedioxy group optionally substituted by halogen atom(s),
$X^3$ is a $(C_1-C_3)$alkyl group optionally substituted by halogen atom(s), and
$X^4$ and $X^7$ are each independently
a hydrogen atom;
a halogen atom; or
a $(C_1-C_3)$alkyl group optionally substituted by halogen atom(s),
or a salt thereof;
[18] the N-2-(hetero)arylethylcarboxamide derivative of the above-mentioned [1] or [2], wherein
A is a substituted cyclic group represented by the formula (A8),
or a salt thereof;
[19] the N-2-(hetero)arylethylcarboxamide derivative of any one of the above-mentioned [1], [2] and [18], wherein
A is a substituted cyclic group represented by the formula (A8),
E is
C—H or
C—Y (Y is as defined below),
$R^1$ and $R^2$ are each independently
a hydrogen atom; or
a $(C_1-C_3)$alkyl group,
$R^3$ and $R^4$ are each independently
a hydrogen atom;
a halogen atom; or
a $(C_1-C_6)$ alkyl group, or
$R^3$ and $R^4$ are optionally bonded to each other to form
a $(C_3-C_6)$cycloalkane,
each Y is independently
a halogen atom;
a cyano group;
a $(C_1-C_6)$alkyl group optionally substituted by halogen atom(s);
a $(C_1-C_6)$alkoxy group optionally substituted by halogen atom(s);
a $(C_1-C_6)$alkylthio group optionally substituted by halogen atom(s);
a $(C_1-C_6)$alkylsulfinyl group optionally substituted by halogen atom(s);

a ($C_1$-$C_6$)alkylsulfonyl group optionally substituted by halogen atom(s);
a phenyl group optionally substituted by the same or different one or more substituents selected from the group consisting of
  (i) a halogen atom,
  (ii) a ($C_1$-$C_6$)alkyl group optionally substituted by halogen atom(s) and
  (iii) a ($C_1$-$C_6$)alkoxy group optionally substituted by halogen atom(s); or
a phenoxy group optionally substituted by the same or different one or more substituents selected from the group consisting of
  (i) a halogen atom,
  (ii) a ($C_1$-$C_6$)alkyl group optionally substituted by halogen atom(s) and
  (iii) a ($C_1$-$C_6$)alkoxy group optionally substituted by halogen atom(s),
n is an integer of 1 to 3,
two Y's that become adjacent when n is an integer of 2 or 3 are optionally bonded to each other to show
a ($C_3$-$C_5$)alkylene group;
a ($C_3$-$C_5$) alkenylene group;
a ($C_2$-$C_4$)alkyleneoxy group; or
a ($C_1$-$C_3$)alkylenedioxy group optionally substituted by halogen atom(s), and
$X^3$ is a ($C_1$-$C_3$)alkyl group optionally substituted by halogen atom(s),
or a salt thereof;
[20] the N-2-(hetero)arylethylcarboxamide derivative of the above-mentioned [1] or [2], wherein
A is a substituted cyclic group represented by the formula (A9),
or a salt thereof;
[21] the N-2-(hetero)arylethylcarboxamide derivative of any one of the above-mentioned [1], [2] and [20], wherein
A is a substituted cyclic group represented by the formula (A9),
E is
C—H or
C—Y (Y is as defined below),
$R^1$ and $R^2$ are each independently
a hydrogen atom; or
a ($C_1$-$C_3$)alkyl group,
$R^3$ and $R^4$ are each independently
a hydrogen atom;
a halogen atom; or
a ($C_1$-$C_6$) alkyl group, or
$R^3$ and $R^4$ are optionally bonded to each other to form a ($C_3$-$C_6$)cycloalkane,
each Y is independently
a halogen atom;
a cyano group;
a ($C_1$-$C_6$)alkyl group optionally substituted by halogen atom(s);
a ($C_1$-$C_6$)alkoxy group optionally substituted by halogen atom(s);
a ($C_1$-$C_6$)alkylthio group optionally substituted by halogen atom(s);
a ($C_1$-$C_6$)alkylsulfinyl group optionally substituted by halogen atom(s);
a ($C_1$-$C_6$)alkylsulfonyl group optionally substituted by halogen atom(s);
a phenyl group optionally substituted by the same or different one or more substituents selected from the group consisting of
  (i) a halogen atom,
  (ii) a ($C_1$-$C_6$)alkyl group optionally substituted by halogen atom(s) and
  (iii) a ($C_1$-$C_6$)alkoxy group optionally substituted by halogen atom(s); or
a phenoxy group optionally substituted by the same or different one or more substituents selected from the group consisting of
  (i) a halogen atom,
  (ii) a ($C_1$-$C_6$)alkyl group optionally substituted by halogen atom(s) and
  (iii) a ($C_1$-$C_6$)alkoxy group optionally substituted by halogen atom(s),
n is an integer of 1 to 3,
two Y's that become adjacent when n is an integer of 2 or 3 are optionally bonded to each other to show
a ($C_3$-$C_5$)alkylene group;
a ($C_3$-$C_5$)alkenylene group;
a ($C_2$-$C_4$)alkyleneoxy group; or
a ($C_1$-$C_3$)alkylenedioxy group optionally substituted by halogen atom(s),
$X^1$ is
a halogen atom; or
a ($C_1$-$C_3$)alkyl group optionally substituted by halogen atom(s), and
$X^9$ and $X^9$ are each independently
a hydrogen atom;
a halogen atom; or
a ($C_1$-$C_3$)alkyl group optionally substituted by halogen atom(s),
or a salt thereof;
[22] the N-2-(hetero)arylethylcarboxamide derivative of the above-mentioned [1] or [2], wherein
A is a substituted cyclic group represented by the formula (A10),
or a salt thereof;
[23] the N-2-(hetero)arylethylcarboxamide derivative of any one of the above-mentioned [1], [2] and [22], wherein
A is a substituted cyclic group represented by the formula (A10),
E is
C—H or
C—Y (Y is as defined below),
$R^1$ and $R^2$ are each independently
a hydrogen atom; or
a ($C_1$-$C_3$)alkyl group, or
$R^3$ and $R^4$ are each independently
a hydrogen atom;
a halogen atom; or
a ($C_1$-$C_6$) alkyl group, or
$R^3$ and $R^4$ are optionally bonded to each other to form a ($C_3$-$C_6$)cycloalkane,
each Y is independently
a halogen atom;
a cyano group;
a ($C_1$-$C_6$)alkyl group optionally substituted by halogen atom(s);
a ($C_1$-$C_6$)alkoxy group optionally substituted by halogen atom(s);
a ($C_1$-$C_6$)alkylthio group optionally substituted by halogen atom(s);
a ($C_1$-$C_6$)alkylsulfinyl group optionally substituted by halogen atom(s);
a ($C_1$-$C_6$)alkylsulfonyl group optionally substituted by halogen atom(s);
a phenyl group optionally substituted by the same or different one or more substituents selected from the group consisting of (i) a halogen atom,
(ii) a $(C_1-C_6)$alkyl group optionally substituted by halogen atom(s) and
(iii) a $(C_1-C_6)$alkoxy group optionally substituted by halogen atom(s); or a phenoxy group optionally substituted by the same or different one or more substituents selected from the group consisting of
(i) a halogen atom,
(ii) a $(C_1-C_6)$alkyl group optionally substituted by halogen atom(s) and
(iii) a $(C_1-C_6)$alkoxy group optionally substituted by halogen atom(s), n is an integer of 1 to 3,
two Y's that become adjacent when n is an integer of 2 or 3 are optionally bonded to each other to show
a $(C_3-C_5)$alkylene group;
a $(C_3-C_5)$alkenylene group;
a $(C_2-C_4)$alkyleneoxy group; or
a $(C_1-C_3)$alkylenedioxy group optionally substituted by halogen atom(s),
$X^1$ is a $(C_1-C_3)$alkyl group optionally substituted by halogen atom(s), and
$X^8$ and $X^9$ are each independently
a hydrogen atom;
a halogen atom; or
a $(C_1-C_3)$alkyl group optionally substituted by halogen atom(s),
or a salt thereof;

[24] a pest controlling agent comprising the N-2-(hetero)arylethylcarboxamide derivative of any one of the above-mentioned [1] to [23], or a salt thereof as an active ingredient;

[25] the pest controlling agent of the above-mentioned [24], which is a plant disease controlling agent;

[26] the pest controlling agent of the above-mentioned [24], which is a nematocide; and

[27] a method of controlling pests, which comprises treating an objective crop plant or the soil used for cultivation of the plant with an effective amount of the pest controlling agent of any one of the above-mentioned [24] to [26].

The present invention provides a compound useful as a pest controlling agent showing superior performance as compared to the prior art, particularly a plant disease controlling agent or nematocide having a broad control spectrum at a low dose.

BEST MODE FOR EMBODYING THE INVENTION

The definition of the formula (I) of the N-2-(hetero)arylethylcarboxamide derivative of the present invention is explained in the following.

The "halogen atom" means chlorine atom, bromine atom, iodine atom or fluorine atom.

The "$(C_1-C_6)$alkyl group" is straight chain or branched chain alkyl group having 1 to 6 carbon atoms such as methyl group, ethyl group, normal propyl group, isopropyl group, normal butyl group, isobutyl group, secondary butyl group, tertiary butyl group, normal pentyl group, neopentyl group, normal hexyl group and the like.

The "$(C_1-C_3)$alkyl group" is straight chain or branched chain alkyl group having 1 to 3 carbon atoms, such as methyl group, ethyl group, normal propyl group, isopropyl group and the like.

The "$(C_1-C_6)$alkyl group optionally substituted by halogen atom(s)" is straight chain or branched chain alkyl group having 1 to 6 carbon atoms, such as methyl group, ethyl group, normal propyl group, isopropyl group, normal butyl group, isobutyl group, secondary butyl group, tertiary butyl group, normal pentyl group, neopentyl group, normal hexyl group and the like; and straight chain or branched chain alkyl group having 1 to 6 carbon atoms, which is substituted by the same or different, one or more halogen atoms, such as trifluoromethyl group, difluoromethyl group, perfluoroethyl group, perfluoroisopropyl group, chloromethyl group, bromomethyl group, 1-bromoethyl group, 2,3-dibromopropyl group and the like.

The "$(C_1-C_3)$alkyl group optionally substituted by halogen atom(s)" is straight chain or branched chain alkyl group having 1 to 3 carbon atoms, such as methyl group, ethyl group, normal propyl group, isopropyl group and the like; and straight chain or branched chain alkyl group having 1 to 3 carbon atoms, which is substituted by the same or different, one or more halogen atoms, such as trifluoromethyl group, difluoromethyl group, perfluoroethyl group, perfluoroisopropyl group, chloromethyl group, bromomethyl group, 1-bromoethyl group, 2,3-dibromopropyl group and the like.

The "$(C_2-C_6)$alkenyl group optionally substituted by halogen atom(s)" is straight chain or branched chain alkenyl group having 2 to 6 carbon atoms, such as vinyl group, propenyl group, butenyl group and the like; and straight chain or branched chain alkenyl group having 2 to 6 carbon atoms, which is substituted by the same or different, one or more halogen atoms, such as fluorovinyl group, difluorovinyl group, perfluorovinyl group, 3,3-dichloro-2-propenyl group, 4,4-difluoro-3-butenyl group and the like.

The "$(C_2-C_6)$alkynyl group optionally substituted by halogen atom(s)" is straight chain or branched chain alkynyl group having 2 to 6 carbon atoms, such as ethynyl group, propynyl group, butynyl group and the like; and straight chain or branched chain alkynyl group having 2 to 6 carbon atoms, which is substituted by the same or different, one or more halogen atoms, such as group fluoroethynyl group, perfluoropropynyl group, 4,4,4-trifluoro-2-butynyl group and the like.

The "$(C_1-C_6)$alkoxy group optionally substituted by halogen atom(s)" is straight chain or branched chain alkoxy group having 1 to 6 carbon atoms such as methoxy group, ethoxy group, normal propoxy group, isopropoxy group, normal butoxy group, secondary butoxy group, tertiary butoxy group, normal pentyloxy group, isopentyloxy group, neopentyloxy group, normal hexyloxy group and the like; and straight chain or branched chain alkoxy group having 1 to 6 carbon atoms, which is substituted by the same or different, one or more halogen atoms, such as trifluoromethoxy group, difluoromethoxy group, perfluoroethoxy group, perfluoroisopropoxy group, chloromethoxy group, bromomethoxy group, 1-bromoethoxy group, 2,3-dibromopropoxy group and the like.

The "$(C_1-C_3)$alkoxy group optionally substituted by halogen atom(s)" is straight chain or branched chain alkoxy group having 1 to 3 carbon atoms such as methoxy group, ethoxy group, normal propoxy group, isopropoxy group and the like; and straight chain or branched chain alkoxy group having 1 to 3 carbon atoms, which is substituted by the same or different, one or more halogen atoms, such as trifluoromethoxy group, difluoromethoxy group, perfluoroethoxy group, perfluoroisopropoxy group, chloromethoxy group, bromomethoxy group, 1-bromoethoxy group, 2,3-dibromopropoxy group and the like.

The "$(C_1-C_6)$alkoxy group optionally substituted by substituent(s) selected from the group consisting of halogen atom and $(C_1-C_6)$alkoxy group" is straight chain or branched chain alkoxy group having 1 to 6 carbon atoms such as methoxy group, ethoxy group, normal propoxy group, isopropoxy group, normal butoxy group, secondary butoxy group, tertiary butoxy group, normal pentyloxy group, isopentyloxy group, neopentyloxy group, normal hexyloxy group and the like; and straight chain or branched chain alkoxy group having 1 to 6 carbon atoms, which is substituted by the same or different, one or more halogen atoms and/or the same or different, one or more ($C_1$-$C_6$)alkoxy groups, such as trifluoromethoxy group, difluoromethoxy group, perfluoroethoxy group, perfluoroisopropoxy group, chloromethoxy group, bromomethoxy group, 1-bromoethoxy group, 2,3-dibromopropoxy group, methoxymethoxy group, ethoxymethoxy group, propoxymethoxy group, methoxyethoxy group, ethoxyethoxy group and the like.

The "($C_2$-$C_6$)alkenyloxy group optionally substituted by halogen atom(s)" is straight chain or branched chain alkenyloxy group having 2 to 6 carbon atoms such as propenyloxy group, butenyloxy group, pentenyloxy group and the like; and straight chain or branched chain alkenyloxy group having 2 to 6 carbon atoms, which is substituted by the same or different, one or more halogen atoms, such as fluorovinyloxy group, difluorovinyloxy group, perfluorovinyloxy group, 3,3-dichloro-2-propenyloxy group, 4,4-difluoro-3-butenyloxy group and the like.

The "($C_2$-$C_6$)alkynyloxy group optionally substituted by halogen atom(s)" is straight chain or branched chain alkynyloxy group having 2 to 6 carbon atoms such as propynyloxy group, butynyloxy group, pentynyloxy group and the like; and straight chain or branched chain alkynyloxy group having 2 to 6 carbon atoms, which is substituted by the same or different, one or more halogen atoms, such as fluoroethynyloxy group, perfluoropropynyloxy group, 4,4,4-trifluoro-2-butynyloxy group and the like.

The "($C_1$-$C_6$)alkylthio group optionally substituted by halogen atom(s)" is straight chain or branched chain alkylthio group having 1 to 6 carbon atoms such as methylthio group, ethylthio group, normal propylthio group, isopropylthio group, normal butylthio group, secondary butylthio group, tertiary butylthio group, normal pentylthio group, isopentylthio group, normal hexylthio group and the like; and straight chain or branched chain alkylthio group having 1 to 6 carbon atoms, which is substituted by the same or different, one or more halogen atoms, such as trifluoromethylthio group, difluoromethylthio group, perfluoroethylthio group, perfluoroisopropylthio group, chloromethylthio group, bromomethylthio group, 1-bromoethylthio group, 2,3-dibromopropylthio group and the like.

The "($C_1$-$C_3$)alkylthio group optionally substituted by halogen atom(s)" is straight chain or branched chain alkylthio group having 1 to 3 carbon atoms such as methylthio group, ethylthio group, normal propylthio group, isopropylthio group and the like; and straight chain or branched chain alkylthio group having 1 to 3 carbon atoms, which is substituted by the same or different, one or more halogen atoms, such as trifluoromethylthio group, difluoromethylthio group, perfluoroethylthio group, perfluoroisopropylthio group, chloromethylthio group, bromomethylthio group, 1-bromoethylthio group, 2,3-dibromopropylthio group and the like.

The "($C_1$-$C_6$)alkylsulfinyl group optionally substituted by halogen atom(s)" is straight chain or branched chain alkylsulfinyl group having 1 to 6 carbon atoms such as methylsulfinyl group, ethylsulfinyl group, normal propylsulfinyl group, isopropylsulfinyl group, normal butylsulfinyl group, secondary butylsulfinyl group, tertiary butylsulfinyl group, normal pentylsulfinyl group, isopentylsulfinyl group, normal hexylsulfinyl group and the like; and straight chain or branched chain alkylsulfinyl group having 1 to 6 carbon atoms, which is substituted by the same or different, one or more halogen atoms, such as trifluoromethylsulfinyl group, difluoromethylsulfinyl group, perfluoroethylsulfinyl group, perfluoroisopropylsulfinyl group, chloromethylsulfinyl group, bromomethylsulfinyl group, 1-bromoethylsulfinyl group, 2,3-dibromopropylsulfinyl group and the like.

The "($C_1$-$C_6$)alkylsulfonyl group optionally substituted by halogen atom(s)" is straight chain or branched chain alkylsulfonyl group having 1 to 6 carbon atoms, such as methylsulfonyl group, ethylsulfonyl group, normal propylsulfonyl group, isopropylsulfonyl group, normal butylsulfonyl group, secondary butylsulfonyl group, tertiary butylsulfonyl group, normal pentylsulfonyl group, isopentylsulfonyl group, normal hexylsulfonyl group and the like; and straight chain or branched chain alkylsulfonyl group having 1 to 6 carbon atoms, which is substituted by the same or different, one or more halogen atoms, such as trifluoromethylsulfonyl group, difluoromethylsulfonyl group, perfluoroethylsulfonyl group, perfluoroisopropylsulfonyl group, chloromethylsulfonyl group, bromomethylsulfonyl group, 1-bromoethylsulfonyl group, 2,3-dibromopropylsulfonyl group and the like.

The "($C_1$-$C_6$)alkoxy-carbonyl group" is alkoxy-carbonyl group wherein the alkoxy is straight chain or branched chain and has 1 to 6 carbon atoms, such as methoxycarbonyl group, ethoxycarbonyl group, normal propoxycarbonyl group, isopropoxycarbonyl group, normal butoxycarbonyl group, tertiary butoxycarbonyl group and the like.

The "($C_1$-$C_6$)alkoxyimino($C_1$-$C_3$)alkyl group" is alkoxyimino($C_1$-$C_3$)alkyl group wherein the alkoxy is straight chain or branched chain and has 1 to 6 carbon atoms, such as methoxyiminomethyl group, ethoxyiminomethyl group, normal propoxyiminomethyl group, isopropoxyiminoethyl group and the like.

The "($C_3$-$C_{30}$)trialkylsilyl group" is straight chain or branched chain alkylsilyl group having 3 to 30 carbon atoms in total, such as trimethylsilyl group, triethylsilyl group and the like.

As the "($C_3$-$C_6$)cycloalkane" formed by $R^1$ and $R^2$ or $R^3$ and $R^4$, which are bonded to each other, cyclopropane, cyclobutane, cyclopentane, cyclohexane and the like can be mentioned.

As the "($C_3$-$C_5$)alkylene group", trimethylene group, tetramethylene group, pentamethylene group and the like can be mentioned.

As the "($C_3$-$C_5$)alkenylene group", —$CH_2$—CH=CH—, —$CH_2$—$CH_2$—CH=CH—, —CH=CH—CH=CH—, —$CH_2$—$CH_2$—$CH_2$—CH=CH—, —$CH_2$—$CH_2$—CH=CH—$CH_2$—, —CH=CH—CH=CH—$CH_2$— and the like can be mentioned.

As the "($C_2$-$C_4$)alkyleneoxy group", —$CH_2$—$CH_2$—O—, —$CH_2$—$CH_2$—$CH_2$—O—, —$CH_2$—$CH_2$—$CH_2$—$CH_2$—O— and the like can be mentioned.

As the "($C_1$-$C_3$)alkylenedioxy group optionally substituted by halogen atom(s)", alkylenedioxy group having 1 to 3 carbon atoms such as —O—$CH_2$—O—, —O—$CH_2$—$CH_2$—O—, —O—$CH_2$—$CH_2$—$CH_2$—O— and the like; and the alkylenedioxy group substituted by the same or different, one or more halogen atoms, such as —O—$CF_2$—O—, —O—$CF_2$—$CF_2$—O—, —O—$CCl_2$—O— and the like.

The "mono($C_1$-$C_3$)alkylamino group" is alkylamino group wherein the alkyl is straight chain or branched chain and has 1 to 3 carbon atoms, such as methylamino group, ethylamino group, normal propylamino group, isopropylamino group and the like.

The "di($C_1$-$C_3$)alkylamino group" is amino group having two the same or different straight chain or branched chain alkyl groups having 1 to 3 carbon atoms, such as dimethylamino group, diethylamino group, di-normal propylamino group, diisopropylamino group, N-methyl-N-ethylamino group, N-methyl-N-isopropylamino group and the like.

The "heterocyclyloxy group" is 5- or 6-membered heterocyclyloxy group having 1 to 3, the same or different hetero atoms selected from oxygen atom, sulfur atom and nitrogen atom, or fused heterocyclyloxy group thereof, such as furyloxy group, thienyloxy group, pyrazolyloxy group, imidazolyloxy group, triazolyloxy group, thiazolyloxy group, pyridyloxy group, pyrimidinyloxy group, pyrazinyloxy group, triazinyloxy group, indolyloxy group, benzothiazolyloxy group, quinolyloxy group, quinazolinyloxy group, quinoxalinyloxy group and the like.

The N-2-(hetero)arylethylcarboxamide derivative represented by the formula (I) of the present invention is under the following conditions (1) and (2), to avoid accidental coincidence with a known compound.

(1) When E is nitrogen atom, A is substituted cyclic group represented by the formula (A3).
(2) 2,6-Dichloro-N-[2-[3-(trifluoromethyl)phenyl]ethyl] benzamide is excluded.

As the salts of the N-2-(hetero)arylethylcarboxamide derivative represented by the formula (I) of the present invention, for example, inorganic acid salts such as hydrochloride, sulfate, nitrate, phosphate and the like, organic acid salts such as acetate, fumarate, maleate, oxalate, methanesulfonate, benzenesulfonate, paratoluenesulfonate and the like, and salts with inorganic or organic bases such as sodium ion, potassium ion, calcium ion, trimethylammonium and the like can be recited as examples.

In the compound represented by the formula (I) of the present invention, $R^1$ and $R^2$ are each preferably hydrogen atom; methyl group; or ethyl group. At least one of $R^1$ and $R^2$ is more preferably hydrogen atom, and one of the optically active enantiomers caused thereby is more preferable.

$R^3$ and $R^4$ are each independently hydrogen atom; fluorine atom; or $R^3$ and $R^4$ are preferably bonded to each other to form cyclopropane.

Y is preferably halogen atom such as fluorine atom, chlorine atom, bromine atom, iodine atom and the like; hydroxy group; $(C_1-C_4)$alkyl group optionally substituted by halogen atom(s); $(C_2-C_4)$alkenyl group optionally substituted by halogen atom(s); $(C_1-C_4)$alkoxy group optionally substituted by halogen atom(s); $(C_2-C_4)$alkenyloxy group optionally substituted by halogen atom(s); $(C_1-C_4)$alkylthio group optionally substituted by halogen atom(s); phenyl group optionally substituted by substituent(s) selected from substituent group Z; or phenoxy group optionally substituted by substituent(s) selected from substituent group Z, or the adjacent two Y's are preferably bonded to each other to form $(C_1-C_3)$alkylenedioxy group optionally substituted by halogen atom(s).

Z is preferably halogen atom; halo$(C_1-C_4)$alkyl group; or halo$(C_1-C_4)$ alkoxy group.

n is preferably 2 or 3.

A is preferably substituted cyclic group selected from the group consisting of the formula (A1), (A2), (A3), (A4), (A5), (A6), (A7) and (A9), and more preferably substituted cyclic group represented by the formula (A3).

$X^1$ is preferably halogen atom; $(C_1-C_3)$alkyl group optionally substituted by halogen atom(s) such as trifluoromethyl group, difluoromethyl group and the like; $(C_1-C_3)$alkoxy group optionally substituted by halogen atom(s) such as trifluoromethoxy group, difluoromethoxy group and the like; or $(C_1-C_3)$alkylthio group optionally substituted by halogen atom(s) such as trifluoromethylthio group, difluoromethylthio group and the like, and more preferably trifluoromethyl group.

$X^2$ is preferably hydrogen atom, fluorine atom or chlorine atom, and more preferably hydrogen atom.

$X^3$ is preferably methyl group, trifluoromethyl group or difluoromethyl group.

$X^4$, $X^7$, $X^8$ and $X^9$ are preferably hydrogen atoms.

$X^5$ is preferably methyl group.

$X^6$ is preferably hydrogen atom, amino group, chlorine atom or methyl group.

Q is preferably sulfur atom.

p and q are each preferably 0.

E is preferably C—H or C—Y (Y is as defined above).

While the compound of the present invention can be produced, for example, according to the following production methods, the production methods are not limited to them.

Production Method 1

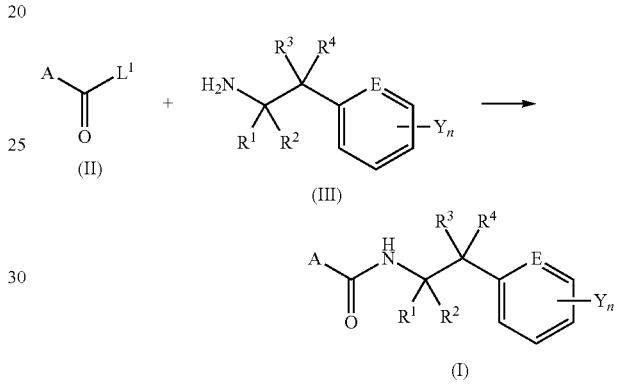

wherein A, $R^1$, $R^2$, $R^3$, $R^4$, E, Y and n are as defined above, and $L^1$ is leaving group such as chlorine atom, bromine atom, alkoxy group and the like.

The N-2-(hetero)arylethylcarboxamide derivative represented by the formula (I) of the present invention can be produced by reacting the (hetero)cyclic carboxylic acid derivative represented by the formula (II) with the 2-(hetero) arylethylamine derivative represented by the formula (III) in the presence of a base in an inert solvent.

The reaction temperature of this reaction is generally within the range of −20° C. to 120° C., and the reaction time is generally within the range of 0.2 hr to 24 hr. The N-2-(hetero)arylethylamine derivative represented by the formula (III) is generally used within the range of 0.2- to 5-fold mol relative to the (hetero)cyclic carboxylic acid derivative represented by the formula (II).

As the base, for example, inorganic bases such as sodium hydroxide, potassium hydroxide, sodium carbonate, potassium carbonate, sodium hydrogen carbonate, potassium hydrogen carbonate and the like; acetates such as sodium acetate, potassium acetate and the like; alkali metal alkoxides such as potassium-t-butoxide, sodium methoxide, sodium ethoxide and the like; tertiary amines such as triethylamine, diisopropylethylamine, 1,8-diazabicyclo[5.4.0]undec-7-ene and the like; nitrogen-containing aromatic compounds such as pyridine, dimethylaminopyridine and the like, and the like can be mentioned. The amount of the base used is generally within the range of 0.5- to 10-fold mol relative to the (hetero) cyclic carboxylic acid derivative represented by the formula (II).

In this reaction, a solvent may or may not be used. Any solvent can be used as long as it does not markedly inhibit the reaction and, for example, alcohols such as methanol, ethanol, propanol, butanol, 2-propanol and the like; linear or cyclic ethers such as diethyl ether, tetrahydrofuran, dioxane and the like; aromatic hydrocarbons such as benzene, toluene, xylene and the like; halogenated hydrocarbons such as methylene chloride, chloroform, carbon tetrachloride and the like, halogenated aromatic hydrocarbons such as chlorobenzene, dichlorobenzene and the like; nitriles such as acetonitrile and the like; esters such as ethyl acetate, butyl acetate and the like; polar solvents such as N,N-dimethylformamide, N,N-dimethylacetamide, dimethyl sulfoxide, 1,3-dimethyl-2-imidazolidinone, water, acetic acid and the like can be used. These inert solvents can be used alone or in a mixture of two or more kinds thereof.

After completion of the reaction, a desired compound can be isolated from a reaction mixture containing the desired compound by a conventional method and, where necessary, purified by recrystallization, column chromatography and the like.

The (hetero)cyclic carboxylic acid derivative represented by the formula (II) to be used for this reaction can be produced by a method described in a known publication (e.g., WO05/115994, WO01/42223, WO03/066609, WO03/066610, WO03/099803, WO03/099804, WO03/080628, etc.) or a method analogous thereto.

The 2-(hetero)arylethylamine derivative represented by the formula (III) can be produced, for example, according to the following intermediate production methods 1 to 4.

Intermediate Production Method 1 (when $R^1$ and $R^2$ are Hydrogen Atoms)

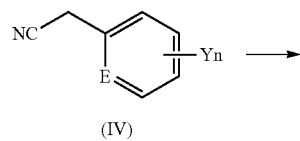

(IV)

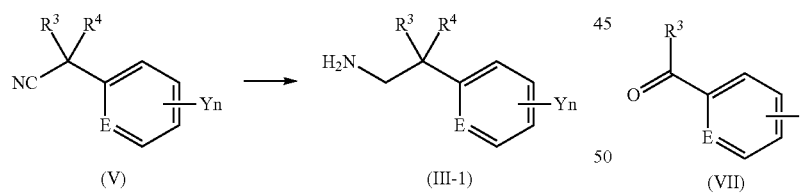

wherein $R^3$, $R^4$, E, Y and n are as defined above.

This reaction can be carried out according to a method described in a known publication (e.g., Tetrahedron, 2002, 58(11), p. 2211. etc.), or a method analogous thereto. That is, the 2-(hetero)arylethylamine derivative represented by the formula (III-1) can be produced by reacting the acetonitrile derivative represented by the formula (IV) with the corresponding alkylating agent in the presence of a base in an inert solvent to give the (hetero)arylacetonitrile derivative represented by the formula (V) and followed by, with or without isolating the (hetero)arylacetonitrile derivative (V), hydrogenation in an inert solvent in the presence of a catalyst such as Raney-nickel and the like, or reduction with a reducing agent such as lithium aluminum hydride and the like.

Intermediate Production Method 2 (when $R^2$ is Hydrogen Atom)

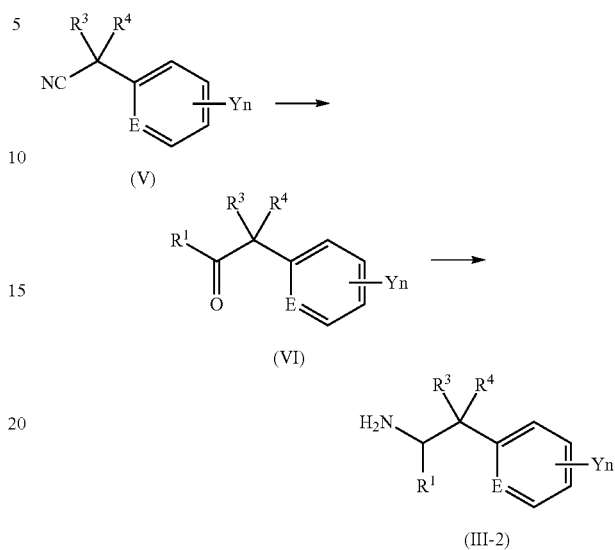

wherein $R^1$, $R^3$, $R^4$, E, Y and n are as defined above.

This reaction can be carried out according to a method described in a known publication (e.g., J. Med. Chem., 1986, 29, p. 302; Angew. Chem., 1989, 28(2), p. 218. etc.), or a method analogous thereto. That is, a 2-(hetero)arylethylamine derivative represented by the formula (III-2) can be produced by subjecting a (hetero)arylacetonitrile derivative represented by the formula (V) to a Grignard reaction to give a ketone derivative represented by the formula (VI) and followed by, with or without isolating the ketone derivative, a Leuckart-Wallach reaction or a similar reductive amination reaction, or reaction with hydroxylamine to give a hydroxime derivative, which is then hydrogenated in the presence of a catalyst such as Raney-nickel and the like.

Intermediate Production Method 3 (when $R^2$ and $R^4$ are Hydrogen Atoms)

wherein $R^1$, $R^3$, E, Y and n are as defined above.

This reaction can be carried out according to a method described in a known publication (e.g., Tetrahedron, 1995, 51(18), p. 5361. etc.), or a method analogous thereto. That is, a 2-(hetero)arylethylamine derivative represented by the formula (III-3) can be produced by reacting a ketone derivative represented by the formula (VII) with nitroalkane represented by the formula (VIII) to give a nitroalkene derivative represented by the formula (IX) and followed by, with or without isolating the nitroalkene derivative (IX), metal reduction with zinc powder and the like, catalytic hydrogenation using a catalyst such as Raney-nickel and the like, or reduction using a reducing agent such as lithium aluminum hydride and the like.

Intermediate Production Method 4

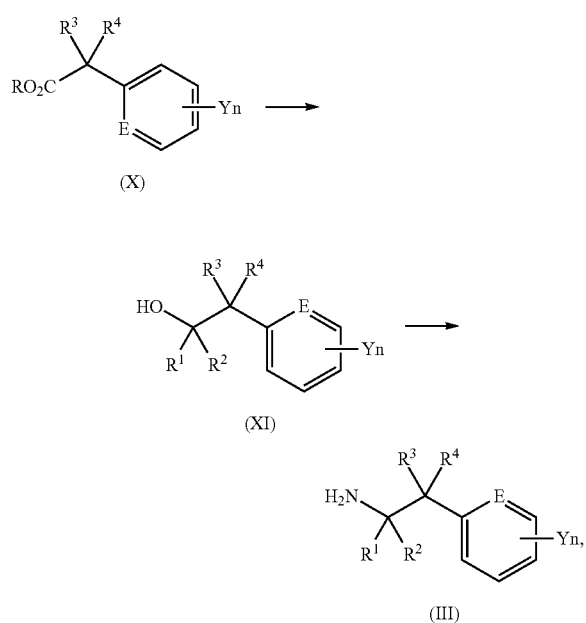

wherein $R^1$, $R^2$, $R^3$, $R^4$, E, Y and n are as defined above.

This reaction can be carried out according to a method described in a known publication (e.g., J. Am. Chem. Soc., 1950, 72, p. 2786. etc.), or a method analogous thereto. That is, a 2-(hetero)arylethylamine derivative represented by the formula (III) can be produced by subjecting a (hetero)arylacetate derivative represented by the formula (X) to a Grignard reaction or a similar reaction to give a (hetero)arylethylalcohol derivative represented by the formula (XI), followed by a Gabriel reaction of a (hetero)arylethyl halide derivative obtained from the (hetero)arylethylalcohol derivative (XI), or a reduction of a (hetero)arylethylazide derivative obtained from the alcohol derivative.

Production Method 2

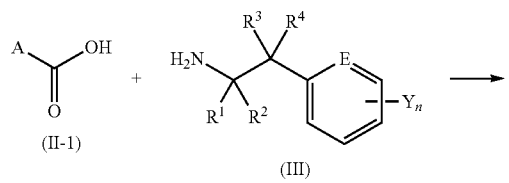

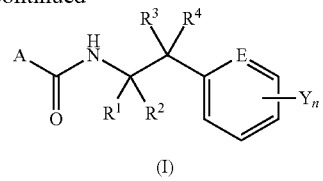

wherein A, $R^1$, $R^2$, $R^3$, $R^4$, E, Y and n are as defined above.)

The N-2-(hetero)arylethylcarboxamide derivative represented by the formula (I) of the present invention can be produced by reacting a (hetero)cyclic carboxylic acid represented by the formula (II-1) with a 2-(hetero)arylethylamine derivative represented by the formula (III) in the presence of a condensation agent and a base in an inert solvent.

The reaction temperature of this reaction is generally within the range of −20° C. to 120° C., and the reaction time is generally within the range of 0.2 hr to 24 hr. The 2-(hetero)arylethylamine derivative represented by the formula (III) is generally used within the range of 0.2- to 5-fold mol relative to the (hetero)cyclic carboxylic acid derivative represented by the formula (II-1).

As the condensation agent to be used in this reaction, for example, diethylphosphoryl cyanide (DEPC), carbonyldiimidazole (CDI), 1,3-dicyclohexylcarbodiimide (DCC), 1-ethyl-3-(3-dimethylaminopropyl)carbodiimide hydrochloride, chlorocarbonates, 2-chloro-1-methylpyridinium iodide and the like can be mentioned and the amount thereof to be used is generally within the range of 0.5- to 3-fold mol relative to the (hetero)cyclic carboxylic acid derivative represented by the formula (II-1).

As the base, for example, inorganic bases such as sodium hydroxide, potassium hydroxide, sodium carbonate, potassium carbonate, sodium hydrogen carbonate, potassium hydrogen carbonate and the like; acetates such as sodium acetate, potassium acetate and the like; alkali metal alkoxides such as potassium-t-butoxide, sodium methoxide, sodium ethoxide and the like; tertiary amines such as triethylamine, diisopropylethylamine, 1,8-diazabicyclo[5.4.0]undec-7-ene and the like; nitrogen-containing aromatic compounds such as pyridine, dimethylaminopyridine and the like, and the like can be mentioned. The amount of the base is generally used within the range of 0.5- to 10-fold mol relative to the (hetero)cyclic carboxylic acid derivative represented by the formula (II-1).

Any solvent can be used for this reaction as long as it does not markedly inhibit the reaction and, for example, linear or cyclic ethers such as diethyl ether, tetrahydrofuran, dioxane and the like; aromatic hydrocarbons such as benzene, toluene, xylene and the like; halogenated hydrocarbons such as methylene chloride, chloroform, carbon tetrachloride and the like; halogenated aromatic hydrocarbons such as chlorobenzene, dichlorobenzene and the like; nitriles such as acetonitrile and the like; esters such as ethyl acetate, acetic acid butyl and the like; and polar solvents such as N,N-dimethylformamide, N,N-dimethylacetamide, dimethyl sulfoxide, 1,3-dimethyl-2-imidazolidinone and the like can be mentioned. These inert solvents can be used alone or in a mixture of two or more kinds thereof.

After completion of the reaction, a desired compound can be isolated from a reaction mixture containing the desired compound by a conventional method and, where necessary, purified by recrystallization, column chromatography and the like.

Representative examples of the thus-obtained N-2-(hetero)arylethylcarboxamide derivative represented by the formula (I) of the present invention are shown in Table 1 to Table 11. However, the derivative of the present invention is not limited to them. In Table 1 to Table 11, "Me" shows methyl group, "Et" shows ethyl group, "Pr" shows propyl group, "Bu" shows butyl group, "Ph" shows phenyl group, "i-" shows iso, and "Q1-Q7" shows the following structures.

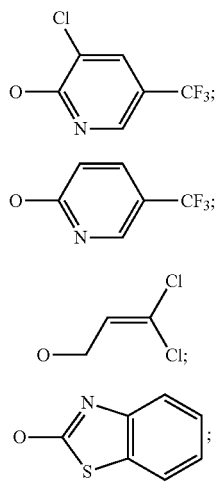

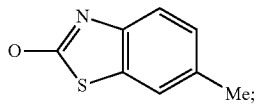

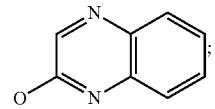

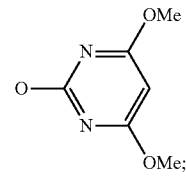

The properties show melting point (° C.) or refractive index $n_D$ (measurement temperature ° C.).

In Table 3, compound Nos. 3-43-R and 3-43-S are optically active forms of compound No. 3-43, and the optical rotation was $[\alpha]_D^{25.0}=-48.18$ (C=1.00, CHCl$_3$) for 3-43-R and $[\alpha]_D^{25.0}=+48.10$ (C=1.00, CHCl$_3$) for 3-43-S. Moreover, $^1$H NMR spectrum data of the compounds, for which "Paste" is indicated in the property column in Table 1 to Table 11, are shown in Table 12.

TABLE 1

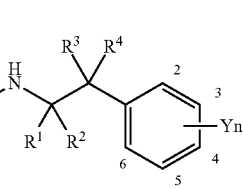

(I-1)

| Comp. No. | X$^1$ | X$^2$ | R$^1$ | R$^2$ | R$^3$ | R$^4$ | Yn | property |
|---|---|---|---|---|---|---|---|---|
| 1-1 | CF$_3$ | H | H | H | H | H | 2-Cl | 104.9-105.7 |
| 1-2 | CF$_3$ | H | H | H | H | H | 3-CF$_3$ | 63-65 |
| 1-3 | CF$_3$ | H | H | H | H | H | 4-Cl | 116.6-117.6 |
| 1-4 | CF$_3$ | H | H | H | Me | H | 4-Cl | 89 |
| 1-5 | CF$_3$ | H | H | H | Me | Me | 4-Cl | 91-92 |
| 1-6 | CF$_3$ | H | H | H | Et | H | 4-Cl | Paste |
| 1-7 | CF$_3$ | H | H | H | Me | Et | 4-Cl | Paste |
| 1-8 | CF$_3$ | H | H | H | Et | Et | 4-Cl | Paste |
| 1-9 | CF$_3$ | H | H | H | i-Bu | H | 4-Cl | Paste |
| 1-10 | I | H | H | H | Me | H | 4-Cl | 119 |
| 1-11 | I | H | H | H | Me | Me | 4-Cl | 121-122 |
| 1-12 | I | H | H | H | Et | H | 4-Cl | 103 |
| 1-13 | I | H | H | H | Me | Et | 4-Cl | Paste |
| 1-14 | I | H | H | H | Et | Et | 4-Cl | Paste |
| 1-15 | I | H | H | H | i-Bu | H | 4-Cl | 86-91 |
| 1-16 | CF$_3$ | H | H | H | H | H | 2,4-Cl$_2$ | 104.2-105.2 |
| 1-17 | CF$_3$ | H | H | H | H | H | 2,3-Cl$_2$ | 135-136 |
| 1-18 | I | H | H | H | H | H | 2,3-Cl$_2$ | 145-146 |
| 1-19 | CF$_3$ | H | H | H | H | H | 2,6-Cl$_2$ | 148.4-149.4 |
| 1-20 | CF$_3$ | H | H | H | H | H | 3,4-Cl$_2$ | 95-96.8 |
| 1-21 | I | H | H | H | H | H | 3,4-Cl$_2$ | 107.2-109.2 |
| 1-22 | CF$_3$ | H | H | H | H | H | 2-Cl-4-F | 81.5-82.8 |
| 1-23 | CF$_3$ | H | H | H | H | H | 2-Me-4-Cl | 97-98 |
| 1-24 | I | H | H | H | H | H | 2-Me-4-Cl | 121-122.7 |
| 1-25 | CF$_3$ | H | H | H | H | H | 2,5-Cl$_2$ | 89.8-90.9 |
| 1-26 | CF$_3$ | H | H | H | H | H | 2,4-(CF$_3$)$_2$ | 112.9-113.7 |
| 1-27 | CF$_3$ | H | H | H | H | H | 2,4-Me$_2$ | 75.1-77.2 |
| 1-28 | CF$_3$ | H | H | H | H | H | 2,5-Me$_2$ | 94-95 |

TABLE 1-continued

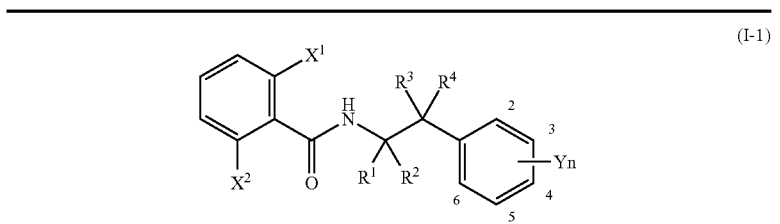

(I-1)

| Comp. No. | $X^1$ | $X^2$ | $R^1$ | $R^2$ | $R^3$ | $R^4$ | Yn | property |
|---|---|---|---|---|---|---|---|---|
| 1-29 | I | H | H | H | H | H | 2,5-Me$_2$ | 115-116 |
| 1-30 | CF$_3$ | H | H | H | H | H | 2-Cl-5-CF$_3$ | 95.7-96.9 |
| 1-31 | I | H | H | H | H | H | 2-Cl-5-CF$_3$ | 122-123 |
| 1-32 | CF$_3$ | H | Me | H | H | H | 2,4-Cl$_2$ | 142 |
| 1-33 | I | H | Me | H | H | H | 2,4-Cl$_2$ | 161-162 |
| 1-34 | CF$_3$ | H | H | H | CH$_2$CH$_2$ | | 2,4-Cl$_2$ | 108-112 |
| 1-35 | I | H | H | H | CH$_2$CH$_2$ | | 2,4-Cl$_2$ | 101-103 |
| 1-36 | F | F | H | H | CH$_2$CH$_2$ | | 2,4-Cl$_2$ | 99-101 |
| 1-37 | CF$_3$ | H | Me | H | CH$_2$CH$_2$ | | 2,4-Cl$_2$ | 107-110 |
| 1-38 | I | H | Me | H | CH$_2$CH$_2$ | | 2,4-Cl$_2$ | 50-51 |
| 1-39 | CF$_3$ | H | H | H | H | H | 2-F-4-CF$_3$ | 94-97 |
| 1-40 | I | H | H | H | H | H | 2-F-4-CF$_3$ | 118 |
| 1-41 | SCHF$_2$ | H | H | H | H | H | 2,4-Cl$_2$ | 103 |
| 1-42 | I | H | H | H | H | H | 2,4-Cl$_2$ | 125-126 |
| 1-43 | Br | H | H | H | H | H | 2,4-Cl$_2$ | 127-128 |
| 1-44 | Cl | H | H | H | H | H | 2,4-Cl$_2$ | 124-126 |
| 1-45 | Me | H | H | H | H | H | 2,4-Cl$_2$ | 136-138 |
| 1-46 | F | H | H | H | H | H | 2,4-Cl$_2$ | 78 |
| 1-47 | F | F | H | H | H | H | 2,4-Cl$_2$ | 75-76 |
| 1-48 | OCF$_3$ | H | H | H | H | H | 2,4-Cl$_2$ | 88-90 |
| 1-49 | CF$_3$ | H | H | H | H | H | 4-Ph(4'-OCF$_3$) | 64-65 |
| 1-50 | CF$_3$ | H | H | H | H | H | 2-F-4-Ph(4'-OCF$_3$) | 146-148 |
| 1-51 | CF$_3$ | H | H | H | H | H | 2-Cl-4-CF$_3$ | 102-103 |
| 1-52 | CF$_3$ | H | H | H | H | H | 2-F-4-Cl | 101-102 |
| 1-53 | CF$_3$ | H | H | H | H | H | 2-Me-4-CF(CF$_3$)$_2$ | Paste |
| 1-54 | I | H | H | H | H | H | 2-Me-4-CF(CF$_3$)$_2$ | 98-100 |
| 1-55 | CF$_3$ | H | H | H | H | H | 2,4-F$_2$ | 94.4-95.8 |
| 1-56 | CF$_3$ | H | H | H | H | H | 2-Cl-4-OCHF$_2$ | Paste |
| 1-57 | CF$_3$ | H | H | H | H | H | 2-Cl-4-Q1 | 135.7-137.2 |
| 1-58 | CF$_3$ | H | H | H | H | H | 2-Cl-4-Q2 | 137.8-138.8 |
| 1-59 | CF$_3$ | H | H | H | H | H | 2-Cl-4-OPh | Paste |
| 1-60 | CF$_3$ | H | H | H | H | H | 2-Cl-4-OPh(4'-CF$_3$) | 109.6-111.5 |
| 1-61 | CF$_3$ | H | H | H | H | H | 2,4,5-Cl$_3$ | 130-131.6 |
| 1-62 | CF$_3$ | H | H | H | H | H | 2,4,5-F$_3$ | |
| 1-63 | CF$_3$ | H | Me | H | H | H | 2-Cl-4-CF$_3$ | 144.5-145.5 |
| 1-64 | CF$_3$ | H | Me | H | H | H | 2,4-F$_2$ | 121.5-124.5 |
| 1-65 | CF$_3$ | H | Me | H | H | H | 2-F-4-Cl | 140.7-142.3 |
| 1-66 | CF$_3$ | H | Me | H | H | H | 2-Cl-4-OH | 169.2-171.6 |
| 1-67 | CF$_3$ | H | Me | H | H | H | 2-Cl-4-OCHF$_2$ | |
| 1-68 | CF$_3$ | H | Me | H | H | H | 2-Cl-4-OCH$_2$OCH$_3$ | 109.2-112.9 |
| 1-69 | CF$_3$ | H | Me | H | H | H | 2-Cl-4-Q1 | 159.5-160.8 |
| 1-70 | CF$_3$ | H | Me | H | H | H | 2-Cl-4-Q2 | |
| 1-71 | CF$_3$ | H | Me | H | H | H | 2-Cl-4-Q3 | 123.9-125.4 |
| 1-72 | CF$_3$ | H | Me | H | H | H | 2-Cl-4-Q4 | |
| 1-73 | CF$_3$ | H | Me | H | H | H | 2-Cl-4-Q5 | |
| 1-74 | CF$_3$ | H | Me | H | H | H | 2-Cl-4-Q6 | |
| 1-75 | CF$_3$ | H | Me | H | H | H | 2-Cl-4-Q7 | |
| 1-76 | CF$_3$ | H | Me | H | H | H | 2-Cl-4-OPh | 118.3-119.8 |
| 1-77 | CF$_3$ | H | Me | H | H | H | 2-Cl-4-OPh(4'-CF$_3$) | |
| 1-78 | CF$_3$ | H | Me | H | H | H | 2-Cl-4-OPh(4'-Cl) | |
| 1-79 | CF$_3$ | H | Me | H | H | H | 2,4,5-F$_3$ | 146.9-148.7 |
| 1-80 | CF$_3$ | H | Me | H | H | H | 2,4,5-Cl$_3$ | 169.1-169.8 |
| 1-81 | CF$_3$ | H | Me | H | H | H | 3,4-Cl$_2$ | 133 |
| 1-82 | I | H | Me | H | H | H | 3,4-Cl$_2$ | 143 |
| 1-83 | CF$_3$ | H | Me | H | H | H | 3-OCF$_2$O-4 | |
| 1-84 | CF$_3$ | H | Me | H | H | H | 3-OCF$_2$CF$_2$O-4 | |
| 1-85 | CF$_3$ | H | Me | H | H | H | 2-Cl-4-OCF$_2$O-5 | |
| 1-86 | CF$_3$ | H | Me | H | H | H | 2-F-4-OCF$_2$O-5 | |
| 1-87 | CF$_3$ | H | Me | Me | H | H | 2,4-Cl$_2$ | 121 |
| 1-88 | CF$_3$ | H | Me | Me | H | H | 3,4-Cl$_2$ | |
| 1-89 | CF$_3$ | H | Me | Me | H | H | 2,4-F$_2$ | |
| 1-90 | CF$_3$ | H | Me | Me | H | H | 3,4-F$_2$ | |
| 1-91 | CF$_3$ | H | CH$_2$CH$_2$ | | H | H | 2,4-Cl$_2$ | |
| 1-92 | CF$_3$ | H | CH$_2$CH$_2$ | | H | H | 2-Cl-4-CF$_3$ | |
| 1-93 | CF$_3$ | H | CH$_2$CH$_2$ | | H | H | 2-F-4-CF$_3$ | |
| 1-94 | CF$_3$ | H | H | H | H | H | 2,5-F$_2$-4-Cl | 95.4-96.2 |

TABLE 1-continued

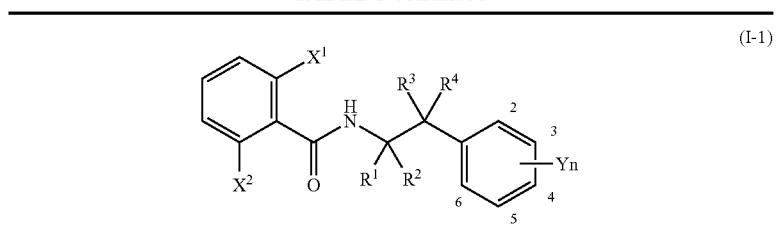

(I-1)

| Comp. No. | X¹ | X² | R¹ | R² | R³ | R⁴ | Yn | property |
|---|---|---|---|---|---|---|---|---|
| 1-95 | $CF_3$ | H | Me | H | H | H | 2,5-$F_2$-4-Cl | 160.2-161.1 |
| 1-96 | $CF_3$ | H | H | H | H | H | 2-Cl-4,5-$F_2$ | 103.6-104.7 |
| 1-97 | $CF_3$ | H | Me | H | H | H | 2-Cl-4,5-$F_2$ | |
| 1-98 | $CF_3$ | H | H | H | H | H | 2-F-4,5-$Cl_2$ | |
| 1-99 | $CF_3$ | H | Me | H | H | H | 2-F-4,5-$Cl_2$ | |
| 1-100 | $CF_3$ | H | H | H | H | H | 2,4-$Cl_2$-5-F | 98.7-99 |
| 1-101 | $CF_3$ | H | Me | H | H | H | 2,4-$Cl_2$-5-F | |
| 1-102 | $CF_3$ | H | H | H | H | H | 2-Cl-4-SMe | 74.1-76.3 |
| 1-103 | $CF_3$ | H | Me | H | H | H | 2-Cl-4-SMe | 125.4-128.4 |
| 1-104 | $CF_3$ | H | H | H | H | H | 2-Cl-4-SOMe | 128.9-129.6 |
| 1-105 | $CF_3$ | H | H | H | H | H | 2-Cl-4-$SO_2$Me | 135.4-137.1 |
| 1-106 | $CF_3$ | H | Me | H | H | H | 2-Br-4-Cl | 143.0 |
| 1-107 | $CF_3$ | H | H | H | H | H | 2-Br-4-F | 106.4 |
| 1-108 | $CF_3$ | H | H | H | H | H | 3-$OCF_2$O-4 | 126.0 |
| 1-109 | F | F | H | H | H | H | 2-Cl-4-Q1 | 134.6-136.7 |

TABLE 2

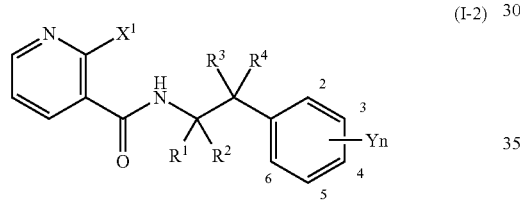

(I-2)

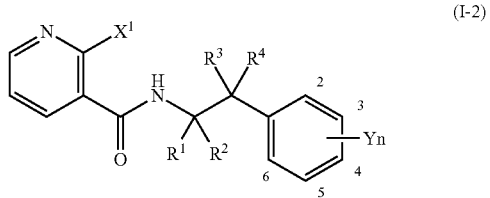

(I-2)

| Comp. No. | X¹ | R¹ | R² | R³ | R⁴ | Yn | property |
|---|---|---|---|---|---|---|---|
| 2-1 | $CF_3$ | H | H | H | H | 2,4-$Cl_2$ | 104.2-105.2 |
| 2-2 | Cl | H | H | H | H | 2-Cl | 92.4-93.3 |
| 2-3 | Cl | H | H | H | H | 3-$CF_3$ | 82-87 |
| 2-4 | Cl | H | H | H | H | 4-Cl | 112.5-113.2 |
| 2-5 | Cl | H | H | Me | H | 4-Cl | Paste |
| 2-6 | Cl | H | H | Me | Me | 4-Cl | Paste |
| 2-7 | Cl | H | H | Et | H | 4-Cl | Paste |
| 2-8 | Cl | H | H | Me | Et | 4-Cl | Paste |
| 2-9 | Cl | H | H | Et | Et | 4-Cl | Paste |
| 2-10 | Cl | H | H | H | H | 2,6-$Cl_2$ | 126.3-127.4 |
| 2-11 | Cl | H | H | H | H | 2,4-$Me_2$ | |
| 2-12 | Cl | H | H | H | H | 2-Cl-4-F | 108.3-109.4 |
| 2-13 | Cl | H | H | H | H | 2-F-4-$CF_3$ | 99 |
| 2-14 | Cl | H | H | H | H | 4-Ph(4-$OCF_3$) | 184-185 |
| 2-15 | Cl | H | H | H | H | 2,5-$Cl_2$ | 99.7-101 |
| 2-16 | Cl | H | H | H | H | 2,4-$Cl_2$ | 98.1-99.2 |
| 2-17 | Cl | H | H | Me | H | 2,4-$Cl_2$ | Paste |
| 2-18 | Cl | H | H | Et | H | 2,4-$Cl_2$ | Paste |
| 2-19 | Cl | H | H | Pr | H | 2,4-$Cl_2$ | 142-144 |
| 2-20 | Cl | H | H | i-Pr | H | 2,4-$Cl_2$ | 93-99 |
| 2-21 | Cl | H | H | Bu | H | 2,4-$Cl_2$ | 90-91 |
| 2-22 | Cl | H | H | i-Bu | H | 2,4-$Cl_2$ | Paste |
| 2-23 | Cl | H | H | Me | Me | 2,4-$Cl_2$ | Paste |
| 2-24 | Cl | H | H | $CH_2CH_2$ | | 2,4-$Cl_2$ | |
| 2-25 | Cl | Me | H | H | H | 2,4-$Cl_2$ | 88-109 |
| 2-26 | Cl | Me | H | $CH_2CH_2$ | | 2,4-$Cl_2$ | 53-63 |
| 2-27 | Cl | H | H | H | H | 2,6-$Cl_2$-4-$CF_3$ | 123.4-124 |
| 2-28 | Cl | H | H | H | H | 2-Cl-4-$CF_3$ | |
| 2-29 | Cl | H | H | H | H | 2-F-4-$CF_3$ | |
| 2-30 | Me | H | H | H | H | 2-Cl-4-$CF_3$ | |
| 2-31 | Me | H | H | H | H | 2,4-$Cl_2$ | 76-85 |
| 2-32 | Cl | H | H | F | H | 2,4-$Cl_2$ | |
| 2-33 | Cl | Me | H | F | H | 2,4-$Cl_2$ | |
| 2-34 | $CF_3$ | H | H | F | H | 2,4-$Cl_2$ | |
| 2-35 | $CF_3$ | Me | H | F | H | 2,4-$Cl_2$ | |
| 2-36 | Cl | H | H | H | H | 2-F-4-Cl | |
| 2-37 | Cl | H | H | H | H | 2-Me-4-CF($CF_3$)$_2$ | 124 |
| 2-38 | Cl | H | H | H | H | 2-Cl-4-$OCHF_2$ | Paste |
| 2-39 | Cl | H | H | H | H | 2-Cl-4-Q1 | 137.8-139.3 |
| 2-40 | Cl | H | H | H | H | 2-Cl-4-Q2 | 127-129 |
| 2-41 | Cl | H | H | H | H | 2-Cl-4-OPh | |
| 2-42 | Cl | H | H | H | H | 2-Cl-4-OPh(4'-$CF_3$) | |
| 2-43 | Cl | H | H | H | H | 2,4,5-$Cl_3$ | |
| 2-44 | Cl | H | H | H | H | 2,4,5-$F_3$ | |
| 2-45 | Cl | Me | H | H | H | 2-Cl-4-$CF_3$ | |
| 2-46 | Cl | Me | H | H | H | 2,4-$F_2$ | 107.6-111.9 |
| 2-47 | Cl | Me | H | H | H | 2-F-4-Cl | |
| 2-48 | Cl | Me | H | H | H | 2-Cl-4-OH | 156.8-158.3 |
| 2-49 | Cl | Me | H | H | H | 2-Cl-4-$OCH_2OCH_3$ | |
| 2-50 | Cl | Me | H | H | H | 2-Cl-4-$OCHF_2$ | |
| 2-51 | Cl | Me | H | H | H | 2-Cl-4-Q1 | 137.8-139.3 |
| 2-52 | Cl | Me | H | H | H | 2-Cl-4-Q2 | 127-129.1 |
| 2-53 | Cl | Me | H | H | H | 2-Cl-4-Q3 | 118.4-119.7 |
| 2-54 | Cl | Me | H | H | H | 2-Cl-4-Q4 | |
| 2-55 | Cl | Me | H | H | H | 2-Cl-4-Q5 | |
| 2-56 | Cl | Me | H | H | H | 2-Cl-4-Q6 | |
| 2-57 | Cl | Me | H | H | H | 2-Cl-4-Q7 | |
| 2-58 | Cl | Me | H | H | H | 2-Cl-4-OPh | 100.8-102.9 |
| 2-59 | Cl | Me | H | H | H | 2-Cl-4-OPh(4'-$CF_3$) | |
| 2-60 | Cl | Me | H | H | H | 2-Cl-4-OPh(4'-Cl) | |
| 2-61 | Cl | Me | H | H | H | 2,4,5-$F_3$ | |
| 2-62 | Cl | Me | H | H | H | 2,4,5-$Cl_3$ | 157.4-158.9 |
| 2-63 | Cl | Me | H | H | H | 3,4-$Cl_2$ | 104-109 |
| 2-64 | Cl | Me | H | H | H | 3-$OCF_2$O-4 | 138.4-138.5 |

TABLE 2-continued

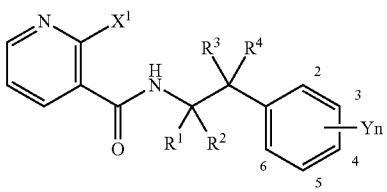
(I-2)

| Comp. No. | X¹ | R¹ | R² | R³ | R⁴ | Yn | property |
|---|---|---|---|---|---|---|---|
| 2-65 | Cl | Me | H | H | H | 3-OCF$_2$CF$_2$O-4 | |
| 2-66 | Cl | Me | H | H | H | 2-Cl-4-OCF$_2$O-5 | |
| 2-67 | Cl | Me | H | H | H | 2-F-4-OCF$_2$O-5 | |
| 2-68 | Cl | Me | Me | H | H | 2,4-Cl$_2$ | |
| 2-69 | Cl | Me | Me | H | H | 3,4-Cl$_2$ | |
| 2-70 | Cl | Me | Me | H | H | 2,4-F$_2$ | |
| 2-71 | Cl | Me | Me | H | H | 3,4-F$_2$ | |
| 2-72 | Cl | CH$_2$CH$_2$ | | H | H | 2,4-Cl$_2$ | |
| 2-73 | Cl | CH$_2$CH$_2$ | | H | H | 2-Cl-4-CF$_3$ | |
| 2-74 | Cl | CH$_2$CH$_2$ | | H | H | 2-F-4-CF$_3$ | |
| 2-75 | Cl | Et | H | H | H | 2,4-Cl$_2$ | |
| 2-76 | Cl | H | H | H | H | 2,5-F$_2$-4-Cl | 116-117.6 |
| 2-77 | Cl | Me | H | H | H | 2,5-F$_2$-4-Cl | 127-129 |
| 2-78 | Cl | H | H | H | H | 2-Cl-4,5-F$_2$ | 131.8-132.8 |
| 2-79 | Cl | Me | H | H | H | 2-Cl-4,5-F$_2$ | 128.4-129.5 |
| 2-80 | Cl | H | H | H | H | 2-F-4,5-Cl$_2$ | |
| 2-81 | Cl | Me | H | H | H | 2-F-4,5-Cl$_2$ | |
| 2-82 | Cl | H | H | H | H | 2,4-Cl$_2$-5-F | 104.5-105 |
| 2-83 | Cl | Me | H | H | H | 2,4-Cl$_2$-5-F | 140.8-141 |
| 2-84 | Cl | Me | H | H | H | 2-Cl-4-OPh(4'-F) | 108.5-109.9 |
| 2-85 | Cl | Me | H | H | H | 2-Cl-4-OPh(3'-F) | Paste |
| 2-86 | Cl | Me | H | H | H | 2-Cl-4-OPh(3'-OMe) | Paste |
| 2-87 | Cl | Me | H | H | H | 2-Br-4-Cl | 135.0 |
| 2-88 | Cl | H | H | H | H | 2-Cl-4-SMe | 76.9-79.4 |
| 2-89 | Cl | H | H | H | H | 2-Cl-4-SOMe | 71.9-113.6 |
| 2-90 | Cl | H | H | H | H | 2-Cl-4-SO$_2$Me | 117.8-119.7 |
| 2-91 | Cl | Me | H | H | H | 2-Cl-4-SMe | 114.1-114.2 |
| 2-92 | Cl | H | H | H | H | 2-Br-4-F | Paste |
| 2-93 | Cl | Me | H | H | H | 2-Br-4-F | 123.4-127.1 |

TABLE 3

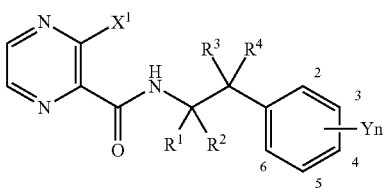
(I-3)

| Comp. No. | X¹ | R¹ | R² | R³ | R⁴ | Yn | property |
|---|---|---|---|---|---|---|---|
| 3-1 | CF$_3$ | H | H | H | H | 2-Cl | |
| 3-2 | CF$_3$ | H | H | H | H | 3-Cl | |
| 3-3 | CF$_3$ | H | H | H | H | 4-Cl | |
| 3-4 | CF$_3$ | H | H | H | H | 3-CF$_3$ | 104-106 |
| 3-5 | CF$_3$ | H | H | H | H | 2,4-Cl$_2$ | 110.2-111.2 |
| 3-6 | CF$_3$ | H | H | H | H | 2-Cl-4-F | 93.1-95.7 |
| 3-7 | CF$_3$ | H | H | H | H | 2-Me-4-Cl | 110.7-112.1 |
| 3-8 | CF$_3$ | H | H | H | H | 2,4-Me$_2$ | Paste |
| 3-9 | CF$_3$ | H | H | H | H | 2,4-(CF$_3$)$_2$ | 102-102.7 |
| 3-10 | CF$_3$ | H | H | H | H | 2-Cl-4-CF$_3$ | 118-119 |
| 3-11 | CF$_3$ | H | H | H | H | 2-F-4-CF$_3$ | 111-113 |
| 3-12 | CF$_3$ | H | H | H | H | 2,4-F$_2$ | 78-86 |
| 3-13 | CF$_3$ | H | H | H | H | 2-Cl-4-Br | |
| 3-14 | CF$_3$ | H | H | H | H | 2-OCHF$_2$-4-Cl | |
| 3-15 | CF$_3$ | H | H | H | H | 2-OPr(i)-4-Cl | 108-110 |
| 3-16 | CF$_3$ | H | H | H | H | 2-Cl-4-SMe | 106.3-108.0 |
| 3-17 | CF$_3$ | H | H | H | H | 2-Cl-4-SCF$_3$ | |
| 3-18 | CF$_3$ | H | H | H | H | 2-Cl-4-SO$_2$Me | 149.2-150.0 |

TABLE 3-continued

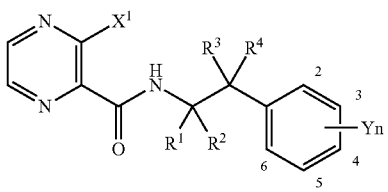
(I-3)

| Comp. No. | X¹ | R¹ | R² | R³ | R⁴ | Yn | property |
|---|---|---|---|---|---|---|---|
| 3-19 | CF$_3$ | H | H | H | H | 2-Cl-4-SO$_2$CF$_3$ | |
| 3-20 | CF$_3$ | H | H | H | H | 2,5-Cl$_2$ | |
| 3-21 | CF$_3$ | H | H | H | H | 2-Cl-5-F | |
| 3-22 | CF$_3$ | H | H | H | H | 2-Me-5-Cl | |
| 3-23 | CF$_3$ | H | H | H | H | 2,5-Me$_2$ | 105.7-106.6 |
| 3-24 | CF$_3$ | H | H | H | H | 2,5-(CF$_3$)$_2$ | |
| 3-25 | CF$_3$ | H | H | H | H | 2-Cl-5-CF$_3$ | 131-133 |
| 3-26 | CF$_3$ | H | H | H | H | 2-F-5-CF$_3$ | |
| 3-27 | CF$_3$ | H | H | H | H | 2,5-F$_2$ | |
| 3-28 | CF$_3$ | H | H | H | H | 2,3-Cl$_2$ | |
| 3-29 | CF$_3$ | H | H | H | H | 2,6-Cl$_2$ | |
| 3-30 | CF$_3$ | H | H | H | H | 3,4-Cl$_2$ | 114-115.2 |
| 3-31 | CF$_3$ | H | H | H | H | 3,4-(OMe)$_2$ | |
| 3-32 | CF$_3$ | H | H | H | H | 3-OCF$_2$O-4 | |
| 3-33 | CF$_3$ | H | H | H | H | 3-OCF$_2$CF$_2$O-4 | |
| 3-34 | CF$_3$ | H | H | H | H | 3,5-Cl$_2$ | |
| 3-35 | CF$_3$ | H | H | H | H | 3,5-(CF$_3$)$_2$ | |
| 3-36 | CF$_3$ | H | H | H | H | 3,5-F$_2$ | |
| 3-37 | CF$_3$ | H | H | H | H | 2,3,4-Cl$_3$ | 150-154 |
| 3-38 | CF$_3$ | H | H | H | H | 2,4,5-Cl$_3$ | |
| 3-39 | CF$_3$ | H | H | H | H | 2-Cl-4-OCH$_2$O-5 | |
| 3-40 | CF$_3$ | H | H | Me | H | 2,4-Cl$_2$ | |
| 3-41 | CF$_3$ | H | H | Et | H | 2,4-Cl$_2$ | |
| 3-42 | CF$_3$ | H | H | CH$_2$CH$_2$ | | 2,4-Cl$_2$ | 91-95 |
| 3-43 | CF$_3$ | Me | H | H | H | 2,4-Cl$_2$ | 163-164 |
| 3-43-R | CF$_3$ | Me | H | H | H | 2,4-Cl$_2$ | 184 |
| 3-43-S | CF$_3$ | Me | H | H | H | 2,4-Cl$_2$ | 183 |
| 3-44 | CF$_3$ | Me | H | CH$_2$CH$_2$ | | 2,4-Cl$_2$ | Paste |
| 3-45 | CF$_3$ | Me | H | F | H | 2,4-Cl$_2$ | |
| 3-46 | CF$_3$ | Me | H | F | F | 2,4-Cl$_2$ | |
| 3-47 | CF$_3$ | H | H | H | H | 4-Ph(4'-CF$_3$) | |
| 3-48 | CF$_3$ | H | H | H | H | 4-Ph(4'-OCF$_3$) | 149-150 |
| 3-49 | CF$_3$ | H | H | H | H | 2-Cl-4-Ph(4'-OCF$_3$) | 124-125 |
| 3-50 | CF$_3$ | H | H | H | H | 2-F-4-Ph(4'-OCF$_3$) | 126-127 |
| 3-51 | CF$_3$ | H | H | H | H | 2-F-4-Cl | 132-133 |
| 3-52 | CF$_3$ | H | H | H | H | 2-Me-4-CF(CF$_3$)$_2$ | Paste |
| 3-53 | CF$_3$ | H | H | H | H | 2-Cl-4-OCHF$_2$ | 68.3-71.9 |
| 3-54 | CF$_3$ | H | H | H | H | 2-Cl-4-Q1 | 128.8-129.9 |
| 3-55 | CF$_3$ | H | H | H | H | 2-Cl-4-Q2 | |
| 3-56 | CF$_3$ | H | H | H | H | 2-Cl-4-OPh | |
| 3-57 | CF$_3$ | H | H | H | H | 2-Cl-4-OPh(4'-CF$_3$) | |
| 3-58 | CF$_3$ | H | H | H | H | 2,4,5-Cl$_3$ | 127.9-130.4 |
| 3-59 | CF$_3$ | H | H | H | H | 2,4,5-F$_3$ | 103-105.9 |
| 3-60 | CF$_3$ | Me | H | H | H | 2-Cl-4-CF$_3$ | 177-178 |
| 3-61 | CF$_3$ | Me | H | H | H | 2,4-F$_2$ | 109.2-110 |
| 3-62 | CF$_3$ | Me | H | H | H | 2-F-4-Cl | 134-135.6 |
| 3-63 | CF$_3$ | Me | H | H | H | 2-Cl-4-OH | 159-162.4 |
| 3-64 | CF$_3$ | Me | H | H | H | 2-Cl-4-OCHF$_2$ | 137.4-140.7 |
| 3-65 | CF$_3$ | Me | H | H | H | 2-Cl-4-Q1 | 177.2-178.3 |
| 3-66 | CF$_3$ | Me | H | H | H | 2-Cl-4-Q2 | |
| 3-67 | CF$_3$ | Me | H | H | H | 2-Cl-4-Q3 | 136.6-137.5 |
| 3-68 | CF$_3$ | Me | H | H | H | 2-Cl-4-Q4 | |
| 3-69 | CF$_3$ | Me | H | H | H | 2-Cl-4-Q5 | |
| 3-70 | CF$_3$ | Me | H | H | H | 2-Cl-4-Q6 | |
| 3-71 | CF$_3$ | Me | H | H | H | 2-Cl-4-Q7 | |
| 3-72 | CF$_3$ | Me | H | H | H | 2-Cl-4-OPh | 127-128.7 |
| 3-73 | CF$_3$ | Me | H | H | H | 2-Cl-4-OPh(4'-CF$_3$) | |
| 3-74 | CF$_3$ | Me | H | H | H | 2-Cl-4-OPh(4'-Cl) | |
| 3-75 | CF$_3$ | Me | H | H | H | 2,4,5-F$_3$ | 125.1-127.9 |
| 3-76 | CF$_3$ | Me | H | H | H | 2,4,5-Cl$_3$ | 195.6-196.5 |
| 3-77 | CF$_3$ | Me | H | H | H | 3,4-Cl$_2$ | 129 |
| 3-78 | CF$_3$ | Me | H | H | H | 3-OCF$_2$O-4 | 164.2 |
| 3-79 | CF$_3$ | Me | H | H | H | 3-OCF$_2$CF$_2$O-4 | |
| 3-80 | CF$_3$ | Me | H | H | H | 2-Cl-4-OCF$_2$O-5 | |
| 3-81 | CF$_3$ | Me | H | H | H | 2-F-4-OCF$_2$O-5 | |
| 3-82 | CF$_3$ | Me | Me | H | H | 2,4-Cl$_2$ | 82-85 |

TABLE 3-continued (I-3)

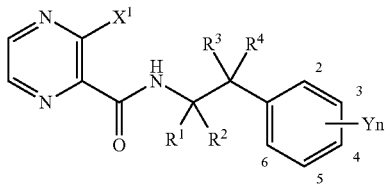

| Comp. No. | X¹ | R¹ | R² | R³ | R⁴ | Yn | property |
|---|---|---|---|---|---|---|---|
| 3-83 | CF₃ | Me | Me | H | H | 3,4-Cl₂ | |
| 3-84 | CF₃ | Me | Me | H | H | 2,4-F₂ | |
| 3-85 | CF₃ | Me | Me | H | H | 3,4-F₂ | |
| 3-86 | CF₃ | CH₂CH₂ | | H | H | 2,4-Cl₂ | 125-128 |
| 3-87 | CF₃ | CH₂CH₂ | | H | H | 2-Cl-4-CF₃ | |
| 3-88 | CF₃ | CH₂CH₂ | | H | H | 2-F-4-CF₃ | |
| 3-89 | CF₃ | Et | H | H | H | 2,4-Cl₂ | 169-175 |
| 3-90 | CF₃ | Et | H | H | H | 2,4-(CF₃)₂ | |
| 3-91 | CF₃ | H | H | H | H | 2,5-F₂-4-Cl | 110.3-112.9 |
| 3-92 | CF₃ | Me | H | H | H | 2,5-F₂-4-Cl | 145-147 |
| 3-93 | CF₃ | H | H | H | H | 2-Cl-4,5-F₂ | 132.2-132.7 |
| 3-94 | CF₃ | Me | H | H | H | 2-Cl-4,5-F₂ | 161.4-162.5 |
| 3-95 | CF₃ | H | H | H | H | 2-F-4,5-Cl₂ | |
| 3-96 | CF₃ | Me | H | H | H | 2-F-4,5-Cl₂ | Paste |
| 3-97 | CF₃ | H | H | O | | 2,4-Cl₂ | |
| 3-98 | CF₃ | Me | H | O | | 2,4-Cl₂ | |
| 3-99 | CF₃ | Me | Me | O | | 2,4-Cl₂ | Paste |
| 3-100 | CF₃ | Me | Me | O | | 3,4-Cl₂ | 133.9-135.2 |
| 3-101 | CF₃ | Me | Me | O | | 2,4,5-Cl₃ | |
| 3-102 | CF₃ | H | H | H | H | 2,4-Cl₂-5-F | 123.3-125.5 |
| 3-103 | CF₃ | Me | H | H | H | 2,4-Cl₂-5-F | 175.9-176 |
| 3-104 | CF₃ | Me | H | H | H | 2-Cl-4-OPh(4'-F) | 128.1-133.5 |
| 3-105 | CF₃ | Me | H | H | H | 2-Cl-4-OPh(3'-F) | 113.7-117 |
| 3-106 | CF₃ | Me | H | H | H | 2-Cl-4-OPh(3'-OMe) | 100.7-103 |
| 3-107 | CF₃ | Me | H | H | H | 2,4-Br₂ | |
| 3-108 | CF₃ | Me | H | H | H | 2-Br-4-F | |
| 3-109 | CF₃ | Me | H | H | H | 2-Br-4-CF₃ | |
| 3-110 | CF₃ | Me | H | H | H | 2-Br-4-OCHF₂ | |
| 3-111 | CF₃ | Me | H | H | H | 2-Br-4-OCHF₂ | |
| 3-112 | CF₃ | Me | H | H | H | 2-Br-4-Cl-5-F | |
| 3-113 | CF₃ | Me | H | H | H | 2,4-Br₂-5-F | |
| 3-114 | CF₃ | Me | H | H | H | 2-Br-4-SCF₃ | |
| 3-115 | CF₃ | Me | H | H | H | 2-Br-4-SOCF₃ | |
| 3-116 | CF₃ | Me | H | H | H | 2-Br-4-SO₂CF₃ | |
| 3-117 | CF₃ | Me | H | H | H | 2-Cl-4-OCF₃ | |
| 3-118 | CF₃ | Me | H | H | H | 2-Br-4-Cl | 154 |
| 3-119 | CF₃ | H | H | H | H | 2-Cl-SOMe | 101.4-103.4 |
| 3-120 | CF₃ | Me | H | H | H | 2-Cl-4-SMe | 142.4 |
| 3-121 | CF₃ | H | H | H | H | 2-Br-4-F | 112.0 |
| 3-122 | CF₃ | Me | H | H | H | 2-Br-4-F | 140.6-141.8 |
| 3-123 | CF₃ | Me | H | H | H | 2-Cl-4-OCH₂CH₃ | 153.1-154.0 |
| 3-124 | CF₃ | Me | H | H | H | 2-Cl-4-OCH(Me)₂ | 122.5 |
| 3'-1 | Cl | H | H | H | H | 2-Cl | |
| 3'-2 | Cl | H | H | H | H | 3-Cl | |
| 3'-3 | Cl | H | H | H | H | 4-Cl | |
| 3'-4 | Cl | H | H | H | H | 3-CF₃ | 98-100 |
| 3'-5 | Cl | H | H | H | H | 2,4-Cl₂ | 99-100 |
| 3'-6 | Cl | H | H | H | H | 2-Cl-4-F | 77-79 |
| 3'-7 | Cl | H | H | H | H | 2-Me-4-Cl | 96.5-97.4 |
| 3'-8 | Cl | H | H | H | H | 2,4-Me₂ | |
| 3'-9 | Cl | H | H | H | H | 2,4-(CF₃)₂ | |
| 3'-10 | Cl | H | H | H | H | 2-Cl-4-CF₃ | |
| 3'-11 | Cl | H | H | H | H | 2-F-4-CF₃ | 107-108 |
| 3'-12 | Cl | H | H | H | H | 2,4-F₂ | |
| 3'-13 | Cl | H | H | H | H | 2-Cl-4-Br | |
| 3'-14 | Cl | H | H | H | H | 2-OCHF₂-4-Cl | |
| 3'-15 | Cl | H | H | H | H | 2-OPr(i)-4-Cl | 70.4-71.3 |
| 3'-16 | Cl | H | H | H | H | 2-Cl-4-SMe | |
| 3'-17 | Cl | H | H | H | H | 2-Cl-4-SCF₃ | |
| 3'-18 | Cl | H | H | H | H | 2-Cl-4-SO₂Me | |
| 3'-19 | Cl | H | H | H | H | 2-Cl-4-SO₂CF₃ | |
| 3'-20 | Cl | H | H | H | H | 2,5-Cl₂ | |
| 3'-21 | Cl | H | H | H | H | 2-Cl-5-F | |
| 3'-22 | Cl | H | H | H | H | 2-Me-5-Cl | |
| 3'-23 | Cl | H | H | H | H | 2,5-Me₂ | |
| 3'-24 | Cl | H | H | H | H | 2,5-(CF₃)₂ | |
| 3'-25 | Cl | H | H | H | H | 2-Cl-5-CF₃ | 104-105 |
| 3'-26 | Cl | H | H | H | H | 2-F-5-CF₃ | |
| 3'-27 | Cl | H | H | H | H | 2,5-F₂ | |
| 3'-28 | Cl | H | H | H | H | 2,3-Cl₂ | |
| 3'-29 | Cl | H | H | H | H | 2,6-Cl₂ | |
| 3'-30 | Cl | H | H | H | H | 3,4-Cl₂ | 100-102 |
| 3'-31 | Cl | H | H | H | H | 3,4-(OMe)₂ | 83-85 |
| 3'-32 | Cl | H | H | H | H | 3-OCF₂O-4 | |
| 3'-33 | Cl | H | H | H | H | 3-OCF₂CF₂O-4 | |
| 3'-34 | Cl | H | H | H | H | 3,5-Cl₂ | |
| 3'-35 | Cl | H | H | H | H | 3,5-(CF₃)₂ | |
| 3'-36 | Cl | H | H | H | H | 3,5-F₂ | |
| 3'-37 | Cl | H | H | H | H | 2,3,4-Cl₃ | |
| 3'-38 | Cl | H | H | H | H | 2,4,5-Cl₃ | |
| 3'-39 | Cl | H | H | H | H | 2-Cl-4-OCH₂O-5 | 85-87 |
| 3'-40 | Cl | H | H | Me | H | 2,4-Cl₂ | |
| 3'-41 | Cl | H | H | Me | Me | 2,4-Cl₂ | Paste |
| 3'-42 | Cl | H | H | Et | H | 2,4-Cl₂ | Paste |
| 3'-43 | Cl | H | H | CH₂CH₂ | | 2,4-Cl₂ | Paste |
| 3'-44 | Cl | Me | H | H | H | 2,4-Cl₂ | 168 |
| 3'-45 | Cl | Me | H | CH₂CH₂ | | 2,4-Cl₂ | Paste |
| 3'-46 | Cl | Me | H | F | H | 2,4-Cl₂ | |
| 3'-47 | Cl | Me | H | F | F | 2,4-Cl₂ | |
| 3'-48 | Cl | H | H | H | H | 4-Ph(4'-CF₃) | |
| 3'-49 | Cl | H | H | H | H | 2-Cl-4-Ph(4'-OCF₃) | 132-133 |
| 3'-50 | Cl | H | H | H | H | 2-F-4-Ph(4'-OCF₃) | 136-137 |
| 3'-51 | Cl | H | H | H | H | 2-F-4-Cl | |
| 3'-52 | Cl | H | H | H | H | 2-Me-4-CF(CF₃)₂ | Paste |
| 3'-53 | Cl | H | H | H | H | 2-Cl-4-OCHF₂ | |
| 3'-54 | Cl | H | H | H | H | 2-Cl-4-Q1 | |
| 3'-55 | Cl | H | H | H | H | 2-Cl-4-Q2 | |
| 3'-56 | Cl | H | H | H | H | 2-Cl-4-OPh | |
| 3'-57 | Cl | H | H | H | H | 2-Cl-4-OPh(4'-CF₃) | |
| 3'-58 | Cl | H | H | H | H | 2,4,5-Cl₃ | |
| 3'-59 | Cl | H | H | H | H | 2,4,5-F₃ | |
| 3'-60 | Cl | Me | H | H | H | 2-Cl-4-CF₃ | |
| 3'-61 | Cl | Me | H | H | H | 2,4-F₂ | 149-150 |
| 3'-62 | Cl | Me | H | H | H | 2-F-4-Cl | 143.2-145.8 |
| 3'-63 | Cl | Me | H | H | H | 2-Cl-4-OH | |
| 3'-64 | Cl | Me | H | H | H | 2-Cl-4-OCHF₂ | |
| 3'-65 | Cl | Me | H | H | H | 2-Cl-4-Q1 | 183.7-184.6 |
| 3'-66 | Cl | Me | H | H | H | 2-Cl-4-Q2 | |
| 3'-67 | Cl | Me | H | H | H | 2-Cl-4-Q3 | |
| 3'-68 | Cl | Me | H | H | H | 2-Cl-4-Q4 | |
| 3'-69 | Cl | Me | H | H | H | 2-Cl-4-Q5 | |
| 3'-70 | Cl | Me | H | H | H | 2-Cl-4-Q6 | |
| 3'-71 | Cl | Me | H | H | H | 2-Cl-4-Q7 | |
| 3'-72 | Cl | Me | H | H | H | 2-Cl-4-OPh | |
| 3'-73 | Cl | Me | H | H | H | 2-Cl-4-OPh(4'-CF₃) | |
| 3'-74 | Cl | Me | H | H | H | 2-Cl-4-OPh(4'-Cl) | |
| 3'-75 | Cl | Me | H | H | H | 2,4,5-F₃ | |
| 3'-76 | Cl | Me | H | H | H | 2,4,5-Cl₃ | |
| 3'-77 | Cl | Me | H | H | H | 3,4-Cl₂ | |
| 3'-78 | Cl | Me | H | H | H | 3-OCF₂O-4 | |
| 3'-79 | Cl | Me | H | H | H | 3-OCF₂CF₂O-4 | |
| 3'-80 | Cl | Me | H | H | H | 2-Cl-4-OCF₂O-5 | |
| 3'-81 | Cl | Me | H | H | H | 2-F-4-OCF₂O-5 | |
| 3'-82 | Cl | Me | Me | H | H | 2,4-Cl₂ | |
| 3'-83 | Cl | Me | Me | H | H | 3,4-Cl₂ | |
| 3'-84 | Cl | Me | Me | H | H | 2,4-F₂ | |
| 3'-85 | Cl | Me | Me | H | H | 3,4-F₂ | |
| 3'-86 | Cl | CH₂CH₂ | | H | H | 2,4-Cl₂ | |
| 3'-87 | Cl | CH₂CH₂ | | H | H | 2-Cl-4-CF₃ | |
| 3'-88 | Cl | CH₂CH₂ | | H | H | 2-F-4-CF₃ | |
| 3'-89 | Cl | Et | H | H | H | 2,4-Cl₂ | |
| 3'-90 | Cl | Et | H | H | H | 2,4-(CF₃)₂ | |

TABLE 3-continued

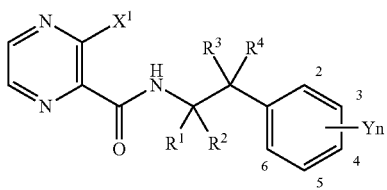

(I-3)

| Comp. No. | X¹ | R¹ | R² | R³ | R⁴ | Yn | property |
|---|---|---|---|---|---|---|---|
| 3'-91 | Cl | H | H | H | H | 2,5-F$_2$-4-Cl | |
| 3'-92 | Cl | Me | H | H | H | 2,5-F$_2$-4-Cl | |
| 3'-93 | Cl | H | H | H | H | 2-Cl-4,5-F$_2$ | |
| 3'-94 | Cl | Me | H | H | H | 2-Cl-4,5-F$_2$ | |
| 3'-95 | Cl | H | H | H | H | 2-F-4,5-Cl$_2$ | |
| 3'-96 | Cl | Me | H | H | H | 2-F-4,5-Cl$_2$ | |
| 3"-1 | Me | H | H | H | H | 2-Cl | |
| 3"-2 | Me | H | H | H | H | 3-Cl | |
| 3"-3 | Me | H | H | H | H | 4-Cl | |
| 3"-4 | Me | H | H | H | H | 3-CF$_3$ | |
| 3"-5 | Me | H | H | H | H | 2,4-Cl$_2$ | 83-91 |
| 3"-6 | Me | H | H | H | H | 2-Cl-4-F | |
| 3"-7 | Me | H | H | H | H | 2-Me-4-Cl | |
| 3"-8 | Me | H | H | H | H | 2,4-Me$_2$ | Paste |
| 3"-9 | Me | H | H | H | H | 2,4-(CF$_3$)$_2$ | |
| 3"-10 | Me | H | H | H | H | 2-Cl-4-CF$_3$ | |
| 3"-11 | Me | H | H | H | H | 2-F-4-CF$_3$ | |
| 3"-12 | Me | H | H | H | H | 2,4-F$_2$ | |
| 3"-13 | Me | H | H | H | H | 2-Cl-4-Br | |
| 3"-14 | Me | H | H | H | H | 2-OCHF$_2$-4-Cl | |
| 3"-15 | Me | H | H | H | H | 2-OPr(i)-4-Cl | |
| 3"-16 | Me | H | H | H | H | 2-Cl-4-SMe | |
| 3"-17 | Me | H | H | H | H | 2-Cl-4-SCF$_3$ | |
| 3"-18 | Me | H | H | H | H | 2-Cl-4-SO$_2$Me | |
| 3"-19 | Me | H | H | H | H | 2-Cl-4-SO$_2$CF$_3$ | |
| 3"-20 | Me | H | H | H | H | 2,5-Cl$_2$ | |
| 3"-21 | Me | H | H | H | H | 2-Cl-5-F | |
| 3"-22 | Me | H | H | H | H | 2-Me-5-Cl | |
| 3"-23 | Me | H | H | H | H | 2,5-Me$_2$ | |
| 3"-24 | Me | H | H | H | H | 2,5-(CF$_3$)$_2$ | |
| 3"-25 | Me | H | H | H | H | 2-Cl-5-CF$_3$ | |
| 3"-26 | Me | H | H | H | H | 2-F-5-CF$_3$ | |
| 3"-27 | Me | H | H | H | H | 2,5-F$_2$ | |
| 3"-28 | Me | H | H | H | H | 2,3-Cl$_2$ | |
| 3"-29 | Me | H | H | H | H | 2,6-Cl$_2$ | |
| 3"-30 | Me | H | H | H | H | 3,4-Cl$_2$ | 85.4-86.1 |
| 3"-31 | Me | H | H | H | H | 3,4-(OMe)$_2$ | |
| 3"-32 | Me | H | H | H | H | 3-OCF$_2$O-4 | |
| 3"-33 | Me | H | H | H | H | 3-OCF$_2$CF$_2$O-4 | |
| 3"-34 | Me | H | H | H | H | 3,5-Cl$_2$ | |
| 3"-35 | Me | H | H | H | H | 3,5-(CF$_3$)$_2$ | |
| 3"-36 | Me | H | H | H | H | 3,5-F$_2$ | |
| 3"-37 | Me | H | H | H | H | 2,3,4-Cl$_3$ | |
| 3"-38 | Me | H | H | H | H | 2,4,5-Cl$_3$ | |
| 3"-39 | Me | H | H | H | H | 2-Cl-4-OCH$_2$O-5 | |
| 3"-40 | Me | H | H | Me | Me | 2,4-Cl$_2$ | Paste |
| 3"-41 | Me | H | H | Et | H | 2,4-Cl$_2$ | |
| 3"-42 | Me | H | H | CH$_2$CH$_2$ | | 2,4-Cl$_2$ | Paste |
| 3"-43 | Me | Me | H | H | H | 2,4-Cl$_2$ | |
| 3"-44 | Me | Me | H | CH$_2$CH$_2$ | | 2,4-Cl$_2$ | |
| 3"-45 | Me | Me | H | F | H | 2,4-Cl$_2$ | |
| 3"-46 | Me | Me | H | F | F | 2,4-Cl$_2$ | |
| 3"-47 | Me | H | H | H | H | 4-Ph(4'-CF$_3$) | 123-124 |
| 3"-48 | Me | H | H | H | H | 4-Ph(4'-OCF$_3$) | 122-123 |
| 3"-49 | Me | H | H | H | H | 2-Cl-4-Ph(4'-OCF$_3$) | |
| 3"-50 | Me | H | H | H | H | 2-F-4-Ph(4'-OCF$_3$) | 85-86 |
| 3"-51 | Me | H | H | H | H | 2-F-4-Cl | |
| 3"-52 | Me | H | H | H | H | 2-Me-4-CF(CF$_3$)$_2$ | |
| 3"-53 | Me | H | H | H | H | 2-Cl-4-OCHF$_2$ | |
| 3"-54 | Me | H | H | H | H | 2-Cl-4-Q1 | |
| 3"-55 | Me | H | H | H | H | 2-Cl-4-Q2 | |
| 3"-56 | Me | H | H | H | H | 2-Cl-4-OPh | |
| 3"-57 | Me | H | H | H | H | 2-Cl-4-OPh(4'-CF$_3$) | |
| 3"-58 | Me | H | H | H | H | 2,4,5-Cl$_3$ | |
| 3"-59 | Me | H | H | H | H | 2,4,5-F$_3$ | |
| 3"-60 | Me | Me | H | H | H | 2-Cl-4-CF$_3$ | |

TABLE 3-continued

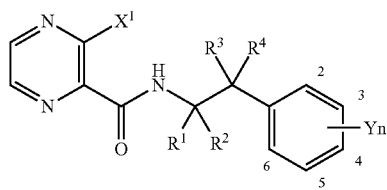

(I-3)

| Comp. No. | X¹ | R¹ | R² | R³ | R⁴ | Yn | property |
|---|---|---|---|---|---|---|---|
| 3"-61 | Me | Me | H | H | H | 2,4-F$_2$ | |
| 3"-62 | Me | Me | H | H | H | 2-F-4-Cl | |
| 3"-63 | Me | Me | H | H | H | 2-Cl-4-OH | |
| 3"-64 | Me | Me | H | H | H | 2-Cl-4-OCHF$_2$ | |
| 3"-65 | Me | Me | H | H | H | 2-Cl-4-Q1 | |
| 3"-66 | Me | Me | H | H | H | 2-Cl-4-Q2 | |
| 3"-67 | Me | Me | H | H | H | 2-Cl-4-Q3 | |
| 3"-68 | Me | Me | H | H | H | 2-Cl-4-Q4 | |
| 3"-69 | Me | Me | H | H | H | 2-Cl-4-Q5 | |
| 3"-70 | Me | Me | H | H | H | 2-Cl-4-Q6 | |
| 3"-71 | Me | Me | H | H | H | 2-Cl-4-Q7 | |
| 3"-72 | Me | Me | H | H | H | 2-Cl-4-OPh | |
| 3"-73 | Me | Me | H | H | H | 2-Cl-4-OPh(4'-CF$_3$) | |
| 3"-74 | Me | Me | H | H | H | 2-Cl-4-OPh(4'-Cl) | |
| 3"-75 | Me | Me | H | H | H | 2,4,5-F$_3$ | |
| 3"-76 | Me | Me | H | H | H | 2,4,5-Cl$_3$ | |
| 3"-77 | Me | Me | H | H | H | 3,4-Cl$_2$ | |
| 3"-78 | Me | Me | H | H | H | 3-OCF$_2$O-4 | |
| 3"-79 | Me | Me | H | H | H | 3-OCF$_2$CF$_2$O-4 | |
| 3"-80 | Me | Me | H | H | H | 2-Cl-4-OCF$_2$O-5 | |
| 3"-81 | Me | Me | H | H | H | 2-F-4-OCF$_2$O-5 | |
| 3"-82 | Me | Me | Me | H | H | 2,4-Cl$_2$ | |
| 3"-83 | Me | Me | Me | H | H | 3,4-Cl$_2$ | |
| 3"-84 | Me | Me | Me | H | H | 2,4-F$_2$ | |
| 3"-85 | Me | Me | Me | H | H | 3,4-F$_2$ | |
| 3"-86 | Me | CH$_2$CH$_2$ | | H | H | 2,4-Cl$_2$ | |
| 3"-87 | Me | CH$_2$CH$_2$ | | H | H | 2-Cl-4-CF$_3$ | |
| 3"-88 | Me | CH$_2$CH$_2$ | | H | H | 2-F-4-CF$_3$ | |
| 3"-89 | Me | Et | H | H | H | 2,4-Cl$_2$ | |
| 3"-90 | Me | Et | H | H | H | 2,4-(CF$_3$)$_2$ | |
| 3"-91 | Me | H | H | H | H | 2,5-F$_2$-4-Cl | |
| 3"-92 | Me | Me | H | H | H | 2,5-F$_2$-4-Cl | |
| 3"-93 | Me | H | H | H | H | 2-Cl-4,5-F$_2$ | |
| 3"-94 | Me | Me | H | H | H | 2-Cl-4,5-F$_2$ | |
| 3"-95 | Me | H | H | H | H | 2-F-4,5-Cl$_2$ | |
| 3"-96 | Me | Me | H | H | H | 2-F-4,5-Cl$_2$ | |
| 3'''-1 | Br | H | H | H | H | 2,4-Cl$_2$ | 125.2-126.1 |
| 3'''-2 | Br | Me | H | H | H | 2,4-Cl$_2$ | 176.7-178 |
| 3'''-3 | Br | Me | H | H | H | 3,4-Cl$_2$ | |
| 3'''-4 | Br | Me | H | H | H | 2,4,5-F$_3$ | |
| 3'''-5 | Br | H | H | H | H | 2-Cl-4-CF$_3$ | |
| 3''''-1 | I | Me | H | H | H | 2,4-Cl$_2$ | 160.9-161.8 |
| 3''''-2 | I | Me | H | H | H | 2,5-F$_2$-4-Cl | |
| 3''''-3 | I | Me | H | H | H | 2,4-Cl$_2$-5-F | |
| 3''''-4 | I | Me | H | H | H | 2-Cl-4,5-F$_2$ | |

TABLE 4

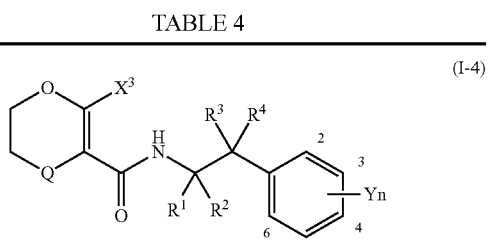

(I-4)

| Comp. No. | Q | X³ | R¹ | R² | R³ | R⁴ | Yn | property |
|---|---|---|---|---|---|---|---|---|
| 4-1 | S | CF$_3$ | H | H | H | H | 2,4-Cl$_2$ | 139 |
| 4-2 | S | Me | H | H | H | H | 2,4-Cl$_2$ | 104 |

TABLE 4-continued

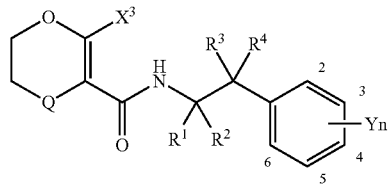

(I-4)

| Comp. No. | Q | X³ | R¹ | R² | R³ | R⁴ | Yn | property |
|---|---|---|---|---|---|---|---|---|
| 4-3 | S | $CF_3$ | H | H | H | H | 2-Cl-4-$CF_3$ | |
| 4-4 | S | Me | H | H | H | H | 2-Cl-4-$CF_3$ | |
| 4-5 | S | $CF_3$ | Me | H | H | H | 2,4-$Cl_2$ | |
| 4-6 | S | $CF_3$ | Me | H | H | H | 2,5-$F_2$-4-Cl | |

TABLE 4-continued

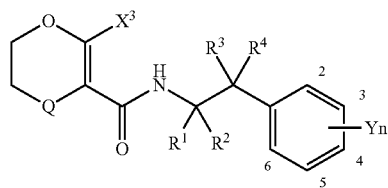

(I-4)

| Comp. No. | Q | X³ | R¹ | R² | R³ | R⁴ | Yn | property |
|---|---|---|---|---|---|---|---|---|
| 4-7 | S | $CF_3$ | Me | H | H | H | 2,4-$Cl_2$-5-F | |
| 4-8 | S | $CF_3$ | Me | H | H | H | 2-Cl-4,5-$F_2$ | |

TABLE 5

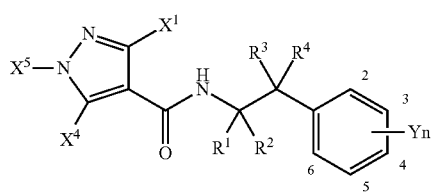

(I-5)

| Comp. No. | X¹ | X⁴ | X⁵ | R¹ | R² | R³ | R⁴ | Yn | property |
|---|---|---|---|---|---|---|---|---|---|
| 5-1 | Me | H | Me | H | H | H | H | 3,4-$Cl_2$ | 131-135 |
| 5-2 | Me | H | Me | H | H | H | H | 3-CH=CH—CH=CH-4 | 103-106 |
| 5-3 | Me | H | Me | H | H | H | H | 3-$CF_3$ | Paste |
| 5-4 | Me | H | Me | H | H | H | H | 2,4-$Cl_2$ | 110-115 |
| 5-5 | Me | H | Me | H | H | Et | H | 2,4-$Cl_2$ | Paste |
| 5-6 | $CF_3$ | H | Me | H | H | H | H | 2,4-$Cl_2$ | 102-103 |
| 5-7 | $CF_3$ | H | Me | H | H | H | H | 3,4-$Cl_2$ | 83-120 |
| 5-8 | $CF_3$ | Me | Me | H | H | H | H | 2,4-$Cl_2$ | 129 |
| 5-9 | Me | Me | Me | H | H | H | H | 2,4-$Cl_2$ | 145-150 |
| 5-10 | $CF_3$ | H | Me | H | H | H | H | 2-Cl-4-$CF_3$ | |
| 5-11 | I | Me | Et | H | H | H | H | 2,4-$Cl_2$ | 143-144 |
| 5-12 | I | Me | Me | H | H | H | H | 2,4-$Cl_2$ | 140-141 |
| 5-13 | Br | Me | Me | H | H | H | H | 2,4-$Cl_2$ | 129-130 |
| 5-14 | Cl | Me | Me | H | H | H | H | 2,4-$Cl_2$ | 112 |
| 5-15 | I | H | Me | H | H | H | H | 2,4-$Cl_2$ | 120-154 |
| 5-16 | Br | H | Me | H | H | H | H | 2,4-$Cl_2$ | 145-147 |
| 5-17 | Cl | H | Me | H | H | H | H | 2,4-$Cl_2$ | 155-157 |
| 5-18 | $CF_3$ | H | Me | H | H | H | H | 2-F-4-Cl | 1.5062 (26° C.) |
| 5-19 | $CF_3$ | H | Me | H | H | H | H | 2-Me-4-$CF(CF_3)_2$ | 77 |
| 5-20 | Me | H | Me | Me | H | H | H | 2,4-$Cl_2$ | 169-170 |
| 5-21 | $CF_3$ | H | Me | Me | H | H | H | 2,4-$Cl_2$ | 163 |
| 5-22 | Me | H | Me | Me | H | H | H | 3,4-$Cl_2$ | 129-134 |
| 5-23 | $CF_3$ | H | Me | Me | H | H | H | 3,4-$Cl_2$ | 133-134 |
| 5-24 | I | H | Me | Me | H | H | H | 2,4-$Cl_2$ | 152-188 |
| 5-25 | Br | H | Me | Me | H | H | H | 2,4-$Cl_2$ | 163-166 |
| 5-26 | Cl | H | Me | Me | H | H | H | 2,4-$Cl_2$ | 141-142 |
| 5-27 | $CHF_2$ | H | Me | Me | H | H | H | 2,4-$Cl_2$ | |
| 5-28 | $CHF_2$ | H | Me | Me | H | H | H | 2,5-$F_2$-4-Cl | |
| 5-29 | $CHF_2$ | H | Me | Me | H | H | H | 2,4-$Cl_2$-5-F | |
| 5-30 | $CHF_2$ | H | Me | Me | H | H | H | 2-Cl-4,5-$F_2$ | |

TABLE 6

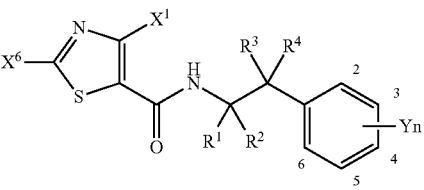

(I-6)

| Comp. No. | $X^1$ | $X^6$ | $R^1$ | $R^2$ | $R^3$ | $R^4$ | Yn | property |
|---|---|---|---|---|---|---|---|---|
| 6-1 | Me | Me | H | H | H | H | 2,4-$Cl_2$ | 95-97 |
| 6-2 | $CF_3$ | Me | H | H | H | H | 2,4-$Cl_2$ | 136 |
| 6-3 | Me | Me | H | H | H | H | 2,4-$Me_2$ | Paste |
| 6-4 | Me | Me | H | H | H | H | 3,4-$Cl_2$ | Paste |
| 6-5 | Me | Me | H | H | H | H | 2-Me-4-Cl | Paste |
| 6-6 | Me | Me | H | H | H | H | 3-CH=CH—CH=CH-4 | 97-99 |
| 6-7 | Me | Me | H | H | H | H | 2-i-Pr-4-Cl | Paste |
| 6-8 | Me | Me | H | H | H | H | 2-Cl-4-$CF_3$ | |
| 6-9 | Me | Me | H | H | H | H | 3-$CF_3$ | 89-90 |
| 6-10 | Me | Me | H | H | H | H | 2-Cl-4-$CF_3$ | |
| 6-11 | Me | Me | H | H | H | H | 2-F-4-$CF_3$ | 115-116 |
| 6-12 | Me | Me | H | H | Me | H | 4-Cl | 89 |
| 6-13 | Me | Me | H | H | Me | Me | 4-Cl | 81 |
| 6-14 | Me | Me | H | H | Et | H | 4-Cl | Paste |
| 6-15 | Me | Me | H | H | Et | Me | 4-Cl | Paste |
| 6-16 | Me | Me | H | H | Et | Et | 4-Cl | Paste |
| 6-17 | Me | Me | H | H | Et | H | 2,4-$Cl_2$ | Paste |
| 6-18 | Me | Me | H | H | n-Pr | H | 2,4-$Cl_2$ | Paste |
| 6-19 | Me | Me | H | H | $CH_2CH_2$ | | 2,4-$Cl_2$ | Paste |
| 6-20 | Me | Me | H | H | i-Pr | H | 2,4-$Cl_2$ | Paste |
| 6-21 | Me | Me | H | H | i-Bu | H | 2,4-$Cl_2$ | Paste |
| 6-22 | Me | Me | Me | H | H | H | 2,4-$Cl_2$ | 154 |
| 6-23 | Me | Me | Me | H | $CH_2CH_2$ | | 2,4-$Cl_2$ | Paste |
| 6-24 | Me | Cl | H | H | H | H | 2,4-$Cl_2$ | Paste |
| 6-25 | $CF_3$ | Me | H | H | H | H | 2-Me-4-CF($CF_3$)$_2$ | 114-115 |
| 6-26 | $CF_3$ | Me | Me | H | H | H | 2,4-$Cl_2$ | 142-144 |
| 6-27 | Me | Me | Me | H | H | H | 3,4-$Cl_2$ | 143 |
| 6-28 | $CF_3$ | Me | Me | H | H | H | 3,4-$Cl_2$ | 142-143 |
| 6-29 | $CHF_2$ | Me | Me | H | H | H | 2,4-$Cl_2$ | |
| 6-30 | $CHF_2$ | Me | Me | H | H | H | 2,5-$F_2$-4-Cl | |
| 6-31 | $CHF_2$ | Me | Me | H | H | H | 2,4-$Cl_2$-5-F | |
| 6-32 | $CHF_2$ | Me | Me | H | H | H | 2-Cl-4,5-$F_2$ | |

TABLE 7

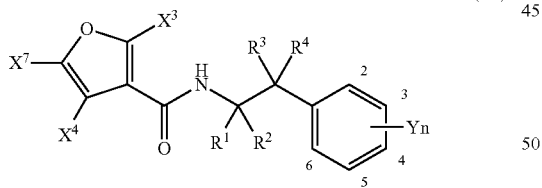

(I-7)

| Comp. No. | $X^3$ | $X^4$ | $X^7$ | $R^1$ | $R^2$ | $R^3$ | $R^4$ | Yn | property |
|---|---|---|---|---|---|---|---|---|---|
| 7-1 | Me | H | H | H | H | H | H | 2,4-$Cl_2$ | 106-107° C. |
| 7-2 | Me | H | H | H | H | H | H | 2-Cl-4-$CF_3$ | |
| 7-3 | $CF_3$ | H | H | H | H | H | H | 2,4-$Cl_2$ | |
| 7-4 | $CF_3$ | H | H | H | H | H | H | 2-Cl-4-$CF_3$ | |
| 7-5 | $CF_3$ | H | H | Me | H | H | H | 2,4-$Cl_2$ | |
| 7-6 | $CF_3$ | H | H | Me | H | H | H | 2,5-$F_2$-4-Cl | |
| 7-7 | $CF_3$ | H | H | Me | H | H | H | 2,4-$Cl_2$-5-F | |
| 7-8 | $CF_3$ | H | H | Me | H | H | H | 2-Cl-4,5-$F_2$ | |

TABLE 8

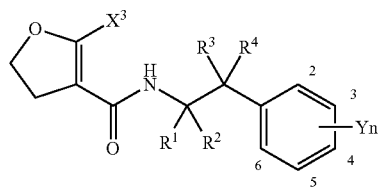

(I-8)

| Comp. No. | $X^3$ | $R^1$ | $R^2$ | $R^3$ | $R^4$ | Yn | property |
|---|---|---|---|---|---|---|---|
| 8-1 | Me | H | H | H | H | 2,4-$Cl_2$ | |
| 8-2 | Me | H | H | H | H | 2-Cl-4-$CF_3$ | |
| 8-3 | $CF_3$ | H | H | H | H | 2,4-$Cl_2$ | |
| 8-4 | $CF_3$ | H | H | H | H | 2-Cl-4-$CF_3$ | |
| 8-5 | $CF_3$ | Me | H | H | H | 2,4-$Cl_2$ | |
| 8-6 | $CF_3$ | Me | H | H | H | 2,5-$F_2$-4-Cl | |
| 8-7 | $CF_3$ | Me | H | H | H | 2,4-$Cl_2$-5-F | |
| 8-8 | $CF_3$ | Me | H | H | H | 2-Cl-4,5-$F_2$ | |

TABLE 9

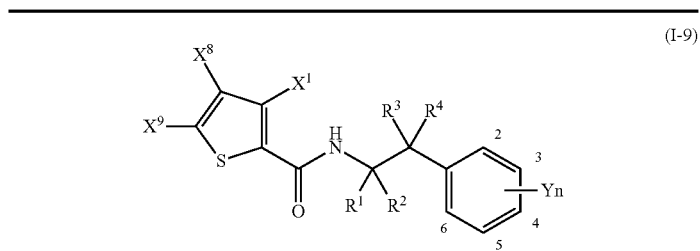

(I-9)

| Comp. No. | X¹ | X⁸ | X⁹ | R¹ | R² | R³ | R⁴ | Yn | property |
|---|---|---|---|---|---|---|---|---|---|
| 9-1 | CF₃ | H | H | H | H | H | H | 2,4-Cl₂ | 67-70° C. |
| 9-2 | I | H | H | H | H | H | H | 2,4-Cl₂ | 81-87° C. |
| 9-3 | CF₃ | H | H | H | H | H | H | 2-Cl-4-CF₃ | |
| 9-4 | Me | H | H | H | H | H | H | 2-Cl-4-CF₃ | |
| 9-5 | CF₃ | H | H | Me | H | H | H | 2,4-Cl₂ | |
| 9-6 | CF₃ | H | H | Me | H | H | H | 2,5-F₂-4-Cl | |
| 9-7 | CF₃ | H | H | Me | H | H | H | 2,4-Cl₂-5-F | |
| 9-8 | CF₃ | H | H | Me | H | H | H | 2-Cl-4,5-F₂ | |

TABLE 10

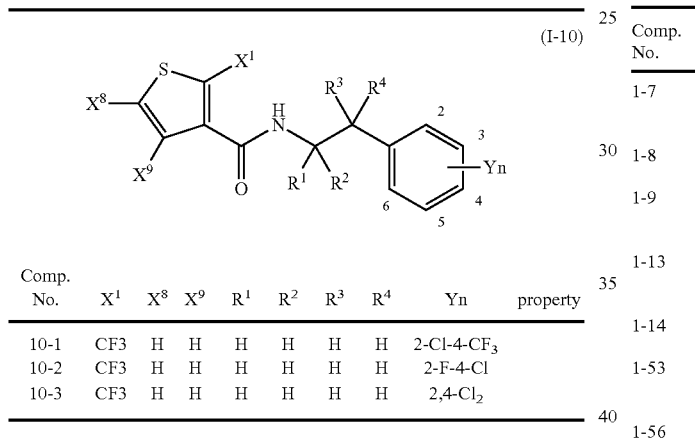

(I-10)

| Comp. No. | X¹ | X⁸ | X⁹ | R¹ | R² | R³ | R⁴ | Yn | property |
|---|---|---|---|---|---|---|---|---|---|
| 10-1 | CF3 | H | H | H | H | H | H | 2-Cl-4-CF₃ | |
| 10-2 | CF3 | H | H | H | H | H | H | 2-F-4-Cl | |
| 10-3 | CF3 | H | H | H | H | H | H | 2,4-Cl₂ | |

TABLE 11

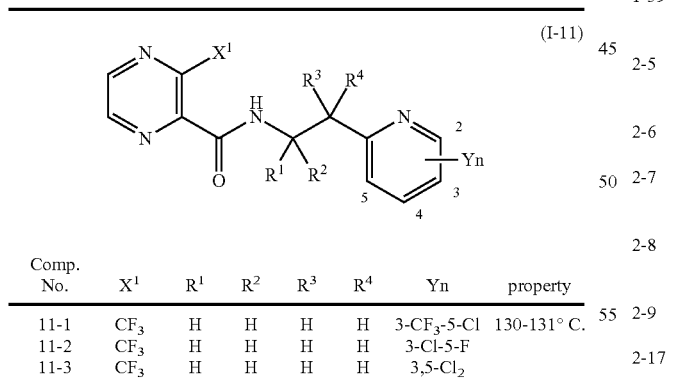

(I-11)

| Comp. No. | X¹ | R¹ | R² | R³ | R⁴ | Yn | property |
|---|---|---|---|---|---|---|---|
| 11-1 | CF₃ | H | H | H | H | 3-CF₃-5-Cl | 130-131° C. |
| 11-2 | CF₃ | H | H | H | H | 3-Cl-5-F | |
| 11-3 | CF₃ | H | H | H | H | 3,5-Cl₂ | |

TABLE 12

| Comp. No. | ¹H-NMR [CDCl₃/TMS, δ value (ppm)] |
|---|---|
| 1-6 | 7.65(dd, 1H), 7.51(m, 2H), 7.32(dd, 1H), 7.30(d, 2H), 7.14(d, 2H), 5.58(br, 1H), 3.92(m, 1H), 3.38(m, 1H), 2.80(m, 1H), 1.79(m, 1H), 1.60(m, 1H), 0.83(t, 3H) |

TABLE 12-continued

| Comp. No. | ¹H-NMR [CDCl₃/TMS, δ value (ppm)] |
|---|---|
| 1-7 | 7.65(d, 1H), 7.51(m, 2H), 7.25-7.36(m, 5H), 5.40(br, 1H), 3.77(dd, 1H), 3.59(dd, 1H), 1.80(m, 1H), 1.66(m, 1H), 1.37(s, 3H), 0.74(t, 3H) |
| 1-8 | 7.65(dd, 1H), 7.51(m, 2H), 7.26-7.37(m, 5H), 5.31(br, 1H), 3.74(d, 2H), 1.75(m, 4H), 0.79(t, 6H) |
| 1-9 | 7.65(dd, 1H), 7.51(m, 2H), 7.32(dd, 1H), 7.29(d, 2H), 7.15(d, 2H), 5.56(br, 1H), 3.87(m, 1H), 3.33(m, 1H), 2.98(m, 1H), 1.53(m, 2H), 1.40(m, 1H), 0.87(t, 3H) |
| 1-13 | 7.81(dd, 1H), 7.27-7.34(m, 5H), 7.22(dd, 1H), 7.05(dt, 1H), 5.43(br, 1H), 3.76(dd, 1H), 3.61(dd, 1H), 1.83(m, 1H), 1.68(m, 1H), 1.41(s, 3H), 0.75(t, 3H) |
| 1-14 | 7.81(dd, 1H), 7.30-7.35(m, 5H), 7.22(dd, 1H), 7.06(dt, 1H), 5.34(br, 1H), 3.75(d, 2H), 1.78(m, 4H), 0.81(t, 6H) |
| 1-53 | 7.70(d, 1H), 7.58(t, 1H), 7.53(t, 1H), 7.46(d, 1H), 7.40(s, 1H), 7.39(d, 1H), 7.30(d, 1H), 5.86(br, 1H), 3.71(dd, 2H), 3.00(t, 2H), 2.44(s, 3H) |
| 1-56 | 7.70(d, 1H), 7.51-7.60(m, 2H), 7.47(d, 1H), 7.30(d, 1H), 7.19(d, 1H), 7.01(dd, 1H), 6.49(t, 1H), 5.84(br, 1H), 3.72(q, 2H), 3.07(t, 2H) |
| 1-59 | 7.69(d, 1H), 7.47-7.60(m, 3H), 7.36(t, 2H), 7.24(d, 1H), 7.15(t, 1H), 7.00-7.03(m, 3H), 6.88(dd, 1H), 5.85(br, 1H), 3.73(q, 2H), 3.05(t, 2H) |
| 2-5 | 8.41(dd, 1H), 8.00(dd, 1H), 7.31(m, 3H), 7.20(d, 1H), 6.39(br, 1H), 3.79(m, 1H), 3.50(m, 1H), 3, 11(m, 1H), 1.35(d, 3H) |
| 2-6 | 8.41(dd, 1H), 8.01(dd, 1H), 7.27-7.36(m, 5H), 6.23(br, 1H), 3.69(d, 2H), 1.43(s, 6H) |
| 2-7 | 8.40(dd, 1H), 7.99(dd, 1H), 7.26-7.33(m, 3H), 7.17(d, 1H), 6.32(br, 1H), 3.91(m, 1H), 3.45(m, 1H), 2.83(m, 1H), 1.80(m, 1H), 1.62(m, 1H), 0.85(t, 3H) |
| 2-8 | 8.41(dd, 1H), 8.03(dd, 1H), 7.27-7.34(m, 4H), 6.18(br, 1H), 3.79(dd, 2H), 3.62(dd, 2H), 1.85(m, 1H), 1.68(m, 1H), 1.41(s, 3H), 0.75(t, 3H) |
| 2-9 | 8.41(dd, 1H), 8.05(dd, 1H), 7.29-7.35(m, 4H), 6.13(br, 1H), 3.77(d, 2H), 1.79(m, 4H), 0.80(t, 6H) |
| 2-17 | 8.42(dd, 1H), 8.00(dd, 1H), 7.39(dd, 1H), 7.31(dd, 1H), 7.27(m, 2H), 6.43(br, 1H), 3.77(m, 1H), 3.65(m, 2H), 1.34(d, 3H) |
| 2-18 | 8.41(dd, 1H), 7.99(dd, 1H), 7.40(d, 1H), 7.30(dd, 1H), 7.25(m, 2H), 6.36(br, 1H), 3.86(m, 1H), 3.60(m, 1H), 3.51(m, 1H), 3.84(m, 1H), 1.67(m, 1H), 0.88(t, 3H) |
| 2-22 | 8.42(dd, 1H), 8.00(dd, 1H), 7.39(dd, 1H), 7.31(dd, 1H), 7.27(m, 2H), 6.36(br, 1H), 3.83(m, 1H), 3.68(m, 1H), 3.51(m, 1H), 1.64(m, 1H), 1.57(m, 1H), 1.44(m, 1H), 0.90(dd, 6H) |
| 2-23 | 8.36(dd, 1H), 7.98(dd, 1H), 7.37(m, 2H), 7.28(dd, 2H), 7.22(dd, 2H), 6.26(br, 1H), 4.06(d, 2H), 1.57(s, 6H) |

TABLE 12-continued

| Comp. No. | $^1$H-NMR [CDCl$_3$/TMS, δ value (ppm)] |
|---|---|
| 2-38 | 8.46(dd, 1H), 8.08(dd, 1H), 7.34(dd, 1H), 7.30(d, 1H), 7.20(d, 1H), 7.02(dd, 1H), 6.55(br, 1H), 6.49(t, 1H), 3.77(q, 2H), 3.10(t, 2H) |
| 2-85 | 8.45(dd, 1H), 8.00(dd, 1H), 7.33(dd, 1H), 7.30(t, 1H), 7.29(d, 1H), 7.05(d, 1H), 6.90(dd, 1H), 6.83(m, 1H), 6.78(dd, 1H), 6.69-6.72(m, 1H), 6.36(d, 1H), 4.50-4.61(m, 1H), 3.07(dd, 1H), 2.99(dd, 1H), 1.35(d, 3H) |
| 2-86 | 8.44(dd, 1H), 7.99(dd, 1H), 7.32(dd, 1H), 7.24(t, 2H), 7.03(d, 1H), 6.88(dd, 1H), 6.75(d, 1H), 6.58(d, 1H), 6.57(s, 1H), 6.35(d, 1H), 4.48-4.59(m, 1H), 3.79(s, 3H), 3.06(dd, 1H), 2.97(dd, 1H), 1.34(d, 3H) |
| 2-92 | 8.46(dd, 1H), 8.09(dd, 1H), 7.27-7.36(m, 3H), 7.00(ddd, 1H), 6.56(br, 1H), 3.76(q, 2H), 3.10(t, 2H) |
| 3-8 | 8.8(d, 1H), 8.7(d, 1H), 7.45(br, 1h), 6.9-7.1(m, 3H), 3.7(q, 2H), 2.9(t, 2H), 2.33(s, 3H), 2.30(s, 3H) |
| 3-44 | 8.80(d, 1H), 8.72(d, 1H), 7.37(d, 1H), 7.32(d, 1H), 7.20(dd, 1H), 4.10(m, 1H), 1.28(m, 1H), 1.24(d, 3H), 1.02(m, 1H), 0.90(m, 1H) |
| 3-52 | 8.82(d, 1H), 8.71(d, 1H), 7.50(br, 1H), 7.40(s, 1H), 7.38(d, 1H), 7.30(d, 1H), 3.75(dd, 2H), 3.02(t, 2H), 2.44(s, 3H) |
| 3'-41 | 8.49(d, 1H), 8.39(d, 1H), 7.42(d, 1H), 7.34(d, 1H), 7.24(br, 1H), 7.21(dd, 1H), 4.02(d, 2H), 1.54(s, 6H) |
| 3'-42 | 8.50(d, 1H), 8.42(d, 1H), 7.47(br, 1H), 7.39(d, 1H), 7.22-7.28(m, 2H), 3.80(m, 1H), 3.58(m, 1H), 3.49(m, 1H), 1.83(m, 1H), 1.68(m, 1H), 0.87(t, 3H) |
| 3'-43 | 8.52(d, 1H), 8.45(d, 1H), 7.61(br, 1H), 7.38(d, 1H), 7.28(d, 1H), 7.16(dd, 1H), 3.65(d, 2H), 1.11(dd, 2H), 0.91(dd, 2H) |
| 3'-45 | 8.53(d, 1H), 8.47(d, 1H), 7.56(br, 1H), 7.37(d, 1H), 7.32(d, 1H), 7.19(dd, 1H), 4.11(m, 1H), 1.28(m, 1H), 1.23(d, 3H), 0.92(m, 1H), 0.87(m, 1H) |
| 3'-52 | 8.54(d, 1H), 8.46(d, 1H), 7.73(br, 1H), 7.40(s, 1H), 7.38(d, 1H), 7.30(d, 1H), 3.71(dd, 2H), 3.01(t, 2H), 2.45(s, 3H) |
| 3''-8 | 8.6(d, 1H), 8.3(d, 1H), 8.0(br, 1H), 7.1(d, 1H), 7.0(d, 1H), 6.97(dd, 1H), 3.6(q, 2H), 3.0(s, 3H), 2.9(t, 2H), 2.34(s, 3H) |
| 3''-40 | 8.55(d, 1H), 8.27(d, 1H), 7.70(br, 1H), 7.42(d, 1H), 7.34(d, 1H), 7.20(dd, 1H), 3.99(d, 2H), 2.96(s, 3H), 1.54(s, 6H) |
| 3''-42 | 8.58(d, 1H), 8.33(d, 1H), 7.97(br, 1H), 7.38(d, 1H), 7.28(d, 1H), 7.16(dd, 1H), 3.63(d, 2H), 2.94(s, 3H), 1.09(dd, 2H), 0.89(dd, 2H) |
| 5-3 | 7.62(s, 1H), 7.4-7.5(m, 4H), 5.55(br, 1H), 3.82(s, 3H), 3.7(q, 2H), 2.98(t, 2H), 2.35(s, 3H) |
| 5-5 | 7.57(s, 1H), 7.39(d, 1H), 7.20-7.29(m, 2H), 5.60(br, 1H), 3.78(s, 3H), 3.78(m, 1H), 3.45(m, 2H), 2.29(s, 3H), 1.79(m, 2H), 1.63(m, 1H), 0.85(t, 3H) |
| 6-3 | 6.9-7.0(m, 3H), 5.7(br, 1H), 3.6(q, 2H), 2.9(t, 2H), 2.7(s, 3H), 2.6(s, 3H), 2.32(s, 3H), 2.30(s, 3H) |
| 6-4 | 7.39(d, 1H), 7.32(d, 1H), 7.07(dd, 1H), 5.65(br, 1H), 3.63(q, 2H), 2.88(t, 2H), 2.66(s, 3H), 2.60(s, 3H) |
| 6-5 | 7.18(d, 1H), 7.13(d, 1H), 7.07(d, 1H), 5.96(br, 1H), 3.59(q, 2H), 2.89(t, 2H), 2.67(s, 3H), 2.60(s, 3H), 2.34(s, 3H) |
| 6-7 | 7.06(d, 1H), 6.88(dd, 1H), 6.87(d, 1H), 5.8(br, 1H), 4.55(m, 1H), 3.60(q, 2H), 2.86(t, 2H), 2.65(s, 3H), 2.57(s, 3H), 1.59(s, 6H) |
| 6-14 | 7.32(d, 2H), 7.14(d, 2H), 5.48(br, 1H), 3.86(m, 1H), 3.30(m, 1H), 2.77(m, 1H), 2.63(s, 3H), 2.47(s, 1H), 1.77(m, 1H), 1.60(m, 1H), 0.84(t, 3H) |
| 6-15 | 7.35(d, 2H), 7.27(d, 2H), 5.30(br, 1H), 3.69(dd, 1H), 3.49(dd, 1H), 2.62(s, 3H), 2.44(s, 3H), 1.82(m, 1H), 1.64(m, 1H), 1.34(s, 3H), 0.74(t, 3H) |
| 6-16 | 7.35(d, 2H), 7.29(d, 2H), 5.22(br, 1H), 3.64(d, 2H), 2.62(s, 3H), 2.42(s, 3H), 1.74(q, 4H), 0.79(t, 6H) |
| 6-17 | 7.41(d, 1H), 7.27(dd, 1H), 7.21(d, 1H), 5.54(br, 1H), 3.77(m, 1H), 3.47(m, 2H), 2.64(s, 3H), 2.50(s, 3H), 1.79(m, 1H), 1.65(m, 1H), 0.86(t, 3H) |
| 6-18 | 7.40(d, 1H), 7.27(dd, 1H), 7.22(d, 1H), 5.52(br, 1H), 3.76(m, 1H), 3.54(m, 1H), 3.45(m, 1H), 2.64(s, 3H), 2.50(s, 3H), 1.65(m, 2H), 1.25(m, 2H), 0.88(t, 3H) |
| 6-19 | 7.39(d, 1H), 7.28(d, 1H), 7.20(dd, 1H), 5.76(br, 1H), 3.57(m, 2H), 2.65(s, 3H), 2.56(s, 3H), 1.07(dd, 2H), 0.90(dd, 2H), |
| 6-20 | 7.42(d, 1H), 7.27(dd, 1H), 7.21(d, 1H), 5.39(br, 1H), 3.96(m, 1H), 3.48(m, 1H), 3.27(m, 1H), 2.62(s, 3H), 2.44(s, 3H), 1.94(m, 1H), 1.11(d, 3H), 0.79(d, 3H) |
| 6-21 | 7.40(d, 1H), 7.27(dd, 1H), 7.22(d, 1H), 5.53(br, 1H), 3.74(m, 1H), 3.62(m, 1H), 3.40(m, 1H), 2.64(s, 3H), 2.51(s, 3H), 1.61(m, 1H), 1.51(m, 1H), 1.41(m, 1H), 0.88(dd, 6H) |
| 6-23 | 7.40(d, 1H), 7.30(d, 1H), 7.22(dd, 1H), 5.69(br, 1H), 4.00(m, 1H), 2.67(s, 3H), 2.61(s, 3H), 1.24(m, 1H), 1.19(d, 3H), 0.88-0.99(m, 3H) |
| 6-24 | 7.41(d, 1H), 7.22(dd, 1H), 7.18(d, 1H), 5.78(br, 1H), 3.66(q, 2H), 3.04(t, 2H), 2.56(s, 3H) |

The pest controlling agent containing N-2-(hetero)arylethylcarboxamide derivative represented by the formula (I) of the present invention or a salt thereof as an active ingredient is particularly suitable for plant disease control of paddy rice, fruit trees, vegetables, other crop plants and flowers and ornamental plants, as well as control of soil pests such as nematodes and the like.

The targeted diseases of the plant disease controlling agent of the present invention are diseases caused by fungi or molds, diseases caused by bacteria, and diseases caused by viruses and, for example, the agent is suitable for controlling the diseases caused by the Fungi Imperfecti family (e.g., the diseases caused by the *Botrytis* genus, the *Helminthsporium* genus, the *Fusarium* genus, the *Septoria* genus, the *Cercospora* genus, the *Pseudocercosporella* genus, the *Rhynchosporium* genus, the *Pyricularia* genus, the *Alternaria* genus, etc.), the diseases caused by the Basidomycetes family (e.g., the diseases caused by the *Hemileia* genus, the *Rhizoctonia* genus, the *Ustilago* genus, the *Typhula* genus, the *Puccinia* genus, etc.), the diseases caused by the Ascomycetes family (e.g., the diseases caused by the *Venturia* genus, the *Podosphaera* genus, the *Leptosphaeria* genus, the *Blumeria* genus, the *Erysiphe* genus, the *Microdochium* genus, *Sclerotinia* genus, the *Gaeumannomyces* genus, the *Monilinia* genus, the *Uncinula* genus, etc.), the diseases caused by miscellaneous families of fungi (e.g., the diseases caused by the *Ascochyta* genus, the *Phoma* genus, the *Pythium* genus, the *Corticium* genus, the *Pyrenophora* genus, etc.), the diseases caused by bacteria, such as the diseases caused by the *Pseudomonas* genus, the *Xanthomonas* genus, the *Erwinia* genus and the like, or the diseases caused by viruses (e.g., the diseases caused by the tobacco mosaic virus, etc.), and the like.

Specific plant diseases include, for example, blast of rice plant (*Pyricularia oryzae*), sheath blight of rice plant (*Rhizoctonia solani*), stripe of rice plant (*Cochiobolus miyabeanus*), seedling blight of rice plant (*Rhizopus chinensis, Pythium graminicola, Fusarium graminicola, Fusarium roseum, Mucor* sp., *Phoma* sp., *Tricoderma* sp.), "bakanae" disease of rice plant (*Gibberella fujikuroi*), powdery mildew of barley and wheat plants (*Blumeria graminis*), or powdery mildew of cucumber plant (*Sphaerotheca fuliginea*), powdery mildew of eggplant plant (*Erysiphe cichoracoarum*), etc. and powdery mildews of miscellaneous host plants, eye spot of barley and wheat plants (*Pseudocercosporella herpotrichoides*), smut of wheat plant (*Urocystis tritici*), snow blight of barley and wheat plants (*Microdochium nivalis, Pythium iwayamai, Typhla ishikariensis, Typhla incarnata, Sclerotinia borealis*), scab of barley and wheat plants (*Fusarium graminearum, Fusarium avenaceum, Fusarium culmorum, Microdochium nivalis*), rust of barley and wheat plants (*Puccinia recondita, Puccinia striiformis, Puccinia graminis*), take-all of barley and wheat plants (*Gaeumannomyces graminis*), crown rust of oat plant (*Puccinia coronata*), and rust of miscellaneous plants, gray mold of cucumber and strawberry plants (*Botrytis cinerea*), stem rot of tomato and cabbage plants (*Sclerotinia sclerotiorum*), late blight of potato and tomato plants (*Phytophthora infestans*) and late blight of miscellaneous plants, downy mildew of various plants such as downy mildew of cucumber plant (*Pseudoperonospora cubensis*), downy mildew of grape tree (*Plasmopara viticola*) and the like, scab of apple tree (*Venturia inaequalis*), leaf spot of apple tree (*Alternaria mali*), black spot of Japanese pear tree (*Alternaria kikuchiana*), stem end rot of citrus fruit trees (*Diaporthe citri*), scab of citrus fruit trees (*Elsinoe fawcetti*), brown leaf spot of beet plant (*Cercospora beticola*), brown leaf spot of peanut plant (*Cercospora arachidicola*), leaf spot of peanut plant (*Cercospora personata*), speckled leaf blotch of wheat plant (*Septoria tritici*), glume blotch of wheat plant (*Leptosphaeria nodorum*), rot blotch of barley plant (*Pyrenophora teres*), leaf stripe of barley plant (*Pyrenophora graminea*), scald of barley plant (*Rhynchosporium secalis*), loose smut of wheat plant (*Ustilago nuda*), stinking smut of wheat plant (*Tilletia caries*), brown patch of turf or lawn grass (*Rhizoctonia solani*), dollar spot of turf or lawn grass (*Sclerotinia homoeocarpa*), the diseases caused by bacteria such as the diseases caused by *Psuedomonas* genus (for example, bacterial spot blotch of cucumber plant (*Pseudomonas syringae* pv. *lachrymans*), bacterial wilt of tomato plant (*Pseudomonas solanacearum*) and bacterial grain rot of rice plant (*Pseudomonas glumae*)), the diseases caused by *Xanthomonas* genus (for example, black rot of cabbage plant (*Xanthomonas campestris*), bacterial leaf blight of rice plant (*Xanthomonas oryzae*), and canker of citrus fruit trees (*Xanthomonas citri*)), the diseases caused by the *Erwinia* genus (for example, bacterial soft rot of cabbage plant (*Erwinia carotovora*)) and the like, the diseases caused by viruses such as tobacco mosaic (Tobacco mosaic virus) and the like, and the like.

In addition, the agent is suitable for controlling nematodes such as root-lesion nematode (*Pratylenchus coffeae*), potato cyst nematode (*Glabodera rostchiensis*), root-knot nematode (*Meloidogyne* sp.), southern root-knot nematode (*Meloidogyne incognita*), citrus nematode (*Tylenchulus semipenetrans*), mycophagous nematode (*Aphelenchus avenae*), chrysanthemum foliar (*Aphelenchoides ritzemabosi*) and the like.

The plants, for which a pest controlling agent of the present invention can be used, are not specifically limited and include, for example, plants such as cereals (e.g. rice, barley, wheat, rye, oat, maize, kaoliang, etc.); legume (soybean, adzuki bean, fava bean, bean, peanut, etc.); fruit trees and fruits (apple, citrus fruits, pear, grapes, peach, plum, cherry, walnut, almond, banana, strawberry, etc.); vegetables (cabbage, tomato, spinach, broccoli, lettuce, onion, welsh onion, green pepper, etc.); root vegetables (carrot, potato, sweet potato, radish, lotus root, turnip, etc.); crop for processing (cotton, flax, paper mulberry, paperbush, rape, beet, hop, sugar cane, sugar beet, olive, rubber, coffee, tobacco, tea, etc.); gourd (pumpkin, cucumber, watermelon, melon, etc.); grass (orchard grass, sorghum, timothy, clover, alfalfa, etc.); grass (Korean lawn grass, bent grass, etc.); crop for spicery (lavender, rosemary, thyme, parsley, pepper, ginger, etc.); and flowers (chrysanthemum, rose, orchid, etc.), etc.

Recently, IPM (integrated pest management) technology using gene recombinant crops (herbicide resistant crop, insect pest resistant crop incorporated with insecticidal toxin generating gene, disease resistant crop incorporated with disease resistance inducer producing gene, taste improved crop, preservability improved crop, yield improved crop, etc.), insect sex pheromone (pheromone disrupting chemicals for leaf roller moths, cabbage armyworm, etc.), natural enemy insect and the like have made progress, and pest controlling agent of the present invention can be used in combination with or by systematization with such technologies.

When the compound of the present invention is used as an active ingredient of pest controlling agents, it may be used as such without addition of other ingredients, but is preferably used after processing into an agrochemical formulation form convenient for use in accordance with the conventional agrochemical-formulation processing method.

That is, the N-2-(hetero)arylethylcarboxamide derivative represented by the formula (I) of the present invention or a salt thereof and, optionally, an adjuvant are blended with a suitable inert carrier in a proper proportion and prepared into a suitable formulation form such as a suspension, emulsifiable concentrate, soluble concentrate, wettable powder, water dispersible granule, granules, dust, tablets, pack or the like through dissolution, dispersion, suspension, mixing, impregnation, adsorption or sticking.

The inert carrier usable in the present invention may be either solid or liquid. As a material usable as the solid carrier, there can be exemplified soybean flour, cereal flour, wood flour, bark flour, saw dust, powdered tobacco stalks, powdered walnut shells, bran, powdered cellulose, extraction residue of vegetables, resins such as powdered synthetic polymers and the like, clays (e.g. kaolin, bentonite, and acid clay), talcs (e.g. talc and pyrophyllite), silica powders or flakes (e.g. diatomaceous earth, silica sand, mica and white carbon [synthetic, high-dispersion silicic acid, also called finely divided hydrated silica or hydrated silicic acid, some of commercially available products contain calcium silicate as the major component]), activated carbon, inorganic or mineral powders such as powdered sulfur, pumice, calcined diatomaceous earth, ground brick, fly ash, sand, calcium carbonate, calcium phosphate and the like, plastic carriers such as polyethylene, polypropylene, poly(vinylidene chloride) and the like, chemical fertilizers (e.g. ammonium sulfate, ammonium phosphate, ammonium nitrate, urea and ammonium chloride), and compost. These carriers may be used alone or as a mixture of two or more kinds thereof.

A material usable as the liquid carrier is selected from materials that have solubility in themselves or which, even without such solubility, are capable of dispersing an active ingredient with the aid of an adjuvant. The following are typical examples of the liquid carrier and can be used alone or as a mixture of two or more kinds thereof: water, alcohols (e.g. methanol, ethanol, isopropanol, butanol and ethylene glycol), ketones (e.g. acetone, methyl ethyl ketone, methyl isobutyl ketone, diisobutyl ketone and cyclohexanone), ethers (e.g. ethyl ether, dioxane, Cellosolve, dipropyl ether and tetrahydrofuran), aliphatic hydrocarbons (e.g. kerosene and mineral oils), aromatic hydrocarbons (e.g. benzene, toluene, xylene, solvent naphtha and alkylnaphthalenes), halogenated hydrocarbons (e.g. dichloroethane, chloroform, carbon tetrachloride and chlorobenzene), esters (e.g. ethyl acetate, diisopropyl phthalate, dibutyl phthalate and dioctyl phthalate), amides (e.g. dimethylformamide, diethylformamide and dimethylacetamide), nitriles (e.g. acetonitrile), and dimethyl sulfoxide.

The following are typical examples of the adjuvant, which are used depending upon purposes and used alone or in combination of two or more kinds, or in some cases, need not be used at all.

To emulsify, disperse, dissolve and/or wet a compound as active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalene sulfonic acid condensation products, ligninsulfonates and higher alcohol sulfate esters.

Further, to stabilize the dispersion of a compound as active ingredient, tackify it and/or bind it, the adjuvants exemplified below may also be used, namely, there may also be used adjuvants such as casein, gelatin, starch, methyl cellulose, carboxymethyl cellulose, gum arabic, poly(vinyl alcohol)s, turpentine, bran oil, bentonite and ligninsulfonates.

To improve the flowability of a solid product, the following adjuvants may also be used, namely, there may be used adjuvants such as waxes, stearates, alkyl phosphates, etc.

Adjuvants such as naphthalenesulfonic acid condensation products and polycondensates of phosphates may be used as a peptizer for dispersible products Adjuvants such as silicone oils may also be used as a defoaming agent.

Adjuvants such as 1,2-benzisothiazoline-3-one, p-chlorom-xylenol, butyl p-hydroxybenzoate may also be added as a preservative.

Further, if necessary, functional spreading agents, active enhancers such as metabolic decomposition inhibitor like piperonyl butoxide, anti-freezing agents such as propylene glycol, antioxidants such as BHT, ultraviolet absorbers, and the other additives may also be added.

The content of the compound as active ingredient may be varied as required, and the compound as active ingredient may be used in a proportion properly chosen in the range of 0.01 to 90 parts by weight per 100 parts of the pest controlling agents. For example, in emulsifiable concentrate, wettable powders, dusts or granules, the suitable content of the compound as active ingredient is from 0.01 to 50% by weight.

In order to control a variety of pests, the pest controlling agent of the present invention may be applied as it is or after being properly diluted with or suspended in water or the like. The applying dosage of the pest controlling agent of the present invention is varied depending upon various factors such as a purpose, pests to be controlled, a growth state of a plant, tendency of pests appearance, weather, environmental conditions, a formulation form, an application method, an application site and application time. It may be properly chosen in the range of 0.001 g to 10 kg, preferably 0.01 g to 1 kg, (in terms of the compound as active ingredient) per 10 ares depending upon purposes.

In order to control a variety of pests, the pest controlling agent to be used for a method of the present invention may be applied to seeds of target plants on which the pests are expected to appear or cultivation carrier for sowing the seeds and the like, as it is or after being properly diluted with or suspended in water or the like, in an amount effective for control of the pests, through the conventional methods such as application methods such as application to rice nursery box, seed dressing and the like, application methods such as seed disinfection method, planting pit application, plant foot application, planting row application, soil incorporation and the like. For plant diseases developed in crops such as fruit trees, cereals, vegetables and the like, the agent can be applied by seed treatments such as dressing or dipping and the like, dipping treatment of nursery root, soil injection of nursery carriers such as planting row at the time of sowing and the like, cultivation container for nursery, planting pit, plant foot and the like, watering after surface dressing, incorporation treatment and the like, to allow absorption of the agent by the plants. The pest controlling agent may be used for treating a water culture medium for hydroponic culture.

As methods for seed treatment, conventional methods such as a method comprising penetration of the agent by dipping of seeds in the liquid agent obtained by diluting or not diluting a liquid formulation or diluting a solid formulation, a method comprising adhering a solid formulation or liquid formulation to the seed surface by admixing the formulation with seeds, dressing and the like, a method comprising admixing the formulation with highly-adhesive carriers such as resin, polymer and the like and forming a single layer or multi-layer coat on the seeds, a method comprising application near the seeds simultaneously with planting and the like can be mentioned.

The "seed" to be subjected to the seed treatment means, in a wise sense, the same as the "plant body for propagation" in the present invention, which includes what is called seeds, as well as plant body for vegetative propagation such as bulb, tuber, seed potato, scaly bulb, stem for cutting propagation, and the like.

The "soil" and "cultivation carrier" when practicing the method of the present invention mean supports for cultivation of plants, and the material is not particularly limited. The material may be any as long as plants can grow therein and includes, for example, various soils, nursery mat, water and the like. In addition, sand, vermiculite, cotton, paper, diatomaceous earth, agar, gelled substance, polymer substance, rock wool, glass wool, wood chip, bark, pumice and the like can also be used.

For application to the soil, for example, a method comprising application of a liquid or solid formulation to the vicinity of plant body, nursery for raising seedling and the like with or without dilution in water, a method comprising application the vicinity of plant body or nursery with granules, a method comprising application with wettable powder, water dispersible granule, granule and the like before sowing or transplantation to allow them to be incorporated into the entire soil, a method comprising application planting pit, planting row and the like with dust, wettable powder, water dispersible granule, granule and the like before sowing or planting
and the like can be mentioned.

In the case of the paddy rice nursery box, the dosage form may vary depending on the timing of, for example, application on sowing, application during greening, application during transplanting and the like. However, the dosage forms of dust, water dispersible granule, granule and the like can be employed.

Application is also possible by incorporation into the grove soil, wherein the grove soil may be mixed with a dust, water dispersible granule, granule and the like and, for example, incorporation into bed soil, incorporation into cover soil, incorporation into the entire grove soil and the like can be employed.

Alternatively, a grove soil and various formulations may be applied in alternate layers. The timing for application on sowing may be any of before sowing, simultaneously with sowing and after sowing. In addition, application after covering soil is available.

For upland crops such as wheat and the like, treatment of seeds, a cultivation carrier to be placed near the plant body and the like during the period of from sowing to raising seedling is preferable. For plants to be directly sown in the field, a direct treatment of seeds, a treatment of a cultivation carrier to be placed near the plant under cultivation and the like are preferable. A application with granules, an soil injection treatment with a liquid agent with or without dilution with water and the like are possible.

For a treatment on sowing or during raising seedling of a cultivated plant to be transplanted, a direct treatment of seeds, an soil injection treatment of nursery for raising seedling with a liquid agent or a dispersal treatment thereof with granules can be applied. In addition, a planting pit may be treated with granules or a cultivation carrier to be placed near the transplantation site may be mixed with the granules during fix planting.

The pest controlling agent of the present invention may be used in admixture with other fungicides, insecticides, acaricides, nematocides, biotic pesticides or the like in order to expand both spectrum of controllable pest species and the period of time when effective application are possible or to reduce the dosage. Furthermore, the agrohorticultural insecticide of the present invention may be used in admixture with herbicides, plant growth regulators, fertilizers or the like, depending upon application situations.

As the other fungicides used for the above purpose, there can be exemplified fungicides such as Sulfur, Lime sulfur, Copper sulfate basic, Iprobenfos, Edifenfos, Tolclofos-methyl, Thiram, Polycarbamate, Zineb, Maneb, Mancozeb, Propineb, Thiophanate, Thiophanate methyl, Benomyl, Iminoctadin acetate, Iminocutadin albecylate, Mepronil, Flutolanil, Pencycuron, Furametpyl, Thifluzamide, Metalaxyl, Oxadixyl, Carpropamid, Dichlofluanid, Flusulfamide, Chlorothalonil, Kresoxim-methyl, Fenoxanil, Himexazol, Etridiazol, Fluoroimide, Procymidone, Vinclozolin, Iprodione, Triadimefon, Bitertanol, Triflumizole, Ipconazole, Fluconazole, Propiconazole, Diphenoconazole, Myclobutanil, Tetraconazole, Hexaconazole, Tebuconazole, Thiadinil, Imibenconazole, Prochloraz, Pefurazoate, Cyproconazole, Isoprothiolane, Fenarimol, Pyrimetanil, Mepanipyrim, Pyrifenox, Fluazinam, Triforine, Diclomezine, Azoxystrobin, Thiadiazin, Captan, Probenazole, Acibenzolar-S-methyl, Fthalide, Tricyclazole, Pyroquilon, Chinomethionat, Oxolinic acid, Dithianon, Kasugamycin, Validamycin, Polyoxin, Blasticidin, Streptomycin, etc.

As the insecticides, acaricides and nematocides, which are used for the same purpose as above, there can be to exemplified insecticides, acaricides and nematocides, such as Ethion, Trichlorfon, Metamidophos, Acephate, Dichlorvos, Mevinphos, Monocrotophos, Malathion, Dimethoate, Formothion, Mecarbam, Vamidothion, Thiometon, Disulfoton, Oxydeprofos, Naled, Methylparathion, Fenitrothion, Cyanophos, Propaphos, Fenthion, Prothiofos, Profenofos, Isofenphos, Temephos, Phenthoate, Dimethylvinphos, Chlorfenvinphos, Tetrachlorvinphos, Phoxim, Isoxathion, Pyraclofos, Methidathion, Chlorpyrifos, Chlorpyrifos-methyl, Pyridaphenthion, Diazinon, Pirimiphosmethyl, Phosalone, Phosmet, Dioxabenzophos, Quinalphos, Terbuphos, Ethoprophos, Cadusafos, Mesulfenfos, DPS (NK-0795), Phosphocarb, Fenamiphos, Isoamidophos, Fosthiazate, Isazophos, Ethoprophos, Fenthion, Fostietane, Dichlofenthion, Thionazin, Sulprofos, Fensulfothion, Diamidafos, Pyrethrin, Allethrin, Prallethrin, Resmethrin, Permethrin, Tefluthrin, Bifenthrin, fenpropathrin, Cypermethrin, α-Cypermethrin, Cyhalothrin, λ-Cyhalothrin, Deltamethrin, Acrinathrin, Fenvalerate, Esfenvalerate, Cycloprothrin, Ethofenprox, Halfenprox, Silafluofen, Flucythrinate, Fluvalinate, Methomyl, Oxamyl, Thiodicarb, Aldicarb, Alanycarb, Cartap, Metolcarb, Xylylcarb, Propoxur, Phenoxycarb, Fenobucarb, Ethiophencarb, Fenothiocarb, Bifenazate, BPMC (2-secondary butyl-phenyl-N-methylcarbamate), Carbaryl, Pirimicarb, Carbofuran, Carbosulfan, Furathiocarb, Benfuracarb, Aldoxycarb, Diafenthiuron, Diflubenzuron, Teflubenzuron, Hexaflumuron, Novaluron, Lufenuron, Flufenoxuron, Chlorfluazuron, Fenbutatin oxide, Tricyclohexyltin hydroxide, Sodium oleate, Potassium oleate, Methoprene, Hydroprene, Binapacryl, Amitraz, Dicofol, Kersen, Chlorobenzilate, Phenisobromolate, Tetradifon, Bensultap, Benzoximate, Tebufenozide, Methoxyfenozide, Pyridalyl, Metaflumizone, Flubendiamide, Chromafenozide, Propargite, Acequinosyl, Endosulfan, Diofenolan, Chlorfenapyl, Fenpyroximate, Tolfenpyrad, Fipronil, Tebufenpyrad, Triazamate, Etoxazole, Hexythiazox, Nicotine sulfate, Nitenpyram, Acetamiprid, Thiacloprid, Imidacloprid, Thiamethoxam, Clothianidin, Dinotefuran, Fluazinam, Pyriproxyfen, Hydramethylnon, Pyrimidifen, Pyridaben, Cyromazine, TPIC (tripropyl isocyanurate), Pymetrozin, Clofentezin, Buprofedin, Thiocyclam, Fenazaquin, Chinomethionate, Indoxacarb, Polynactin complexes, Milbemectin, Abamectin, Emamectin-benzoate, Spinosad, BT (*Bacillus thuringiensis*), Azadirachtin, Rotenone, Hydroxypropyl starch, Levamisole hydrochloride, Metam-sodium, Morantel tartrate, Dazomet, Trichlamide, Pasteuria, Monacrosporium-phymatophagum, etc.

Similarly, as the herbicides, there can be exemplified herbicides such as Glyphosate, Sulfosate, Glyfosinate, Bialaphos, Butamifos, Esprocarb, Prosulcarb, Benthiocarb, Pyributycarb, Asulam, Linuron, Dymron, Isouron, Bensulfuron methyl, Cyclosulfamuron, Cinosulfuron, Pyrazosulfuron ethyl, Azimsulfuron, Imazosulfuron, Tenylchlor, Alachlor, Pretilachlor, Clomeprop, Etobenzanid, Mefenacet, Pendimethalin, Bifenox, Acifluorfen, Lactfen, Cyhalofop-butyl, Ioxynil, Bromobutide, Alloxydim, Setoxydim, Napropamide, Indanofan, Pyrazolate, Benzofenap, Pyraflufen-ethyl, Imazapyl, Sulfentrazone, Cafenstrole, Bentoxazon, Oxadiazon, Paraquat, Diquat, Pyriminobac, Simazine, Atrazine, Dimethametryn, Triazyflam, Benflesate, Flutiacet-methyl, Quizalofop-ethyl, Bentazon, Calcium peroxide, etc.

EXAMPLES

The present invention is specifically explained in the following by referring to Examples, which are not to be construed as limitative as long as they do not depart from the scope of the invention.

Example 1

Production of N-[2-(2,4-dichloro-phenyl)-1-methylethyl]-2-trifluoromethylbenzamide (compound No. 1-32)

1-1)
A mixture of 2,4-dichlorobenzaldehyde (1.45 g, 8.3 mmol), ammonium acetate (0.64 g, 8.3 mmol) and nitroethane (6 g, 80 mmol) was heated under reflux for 6 hr. The mixture was allowed to cool to room temperature and ethyl acetate was added. The mixture was washed with water and saturated brine, dried over anhydrous magnesium sulfate, and concentrated. Recrystallization from ethanol gave 2,4-dichloro-1-(2-nitro-1-propenyl)benzene (yellow needle crystals, yield; 1.0 g, 52%).

1-2)
To a suspension of lithium aluminum hydride (0.33 g, 8.9 mmol) in tetrahydrofuran (20 ml) was added dropwise a solution of 2,4-dichloro-1-(2-nitro-1-propenyl)benzene (1.0 g, 4.3 mmol) in tetrahydrofuran (5 ml) at room temperature. Refluxing started slowly and the mixture was heated under reflux for 1 hr thereafter. The mixture was allowed to cool to room temperature and water (2 ml) was added under cooling in an ice bath. A 1N aqueous sodium hydroxide solution (5 ml) was added, and the insoluble material was removed by filtration through celite. Water was added to the filtrate, and the mixture was extracted with methyl t-butyl ether. The organic layer was washed with saturated brine, dried over anhydrous magnesium sulfate, and concentrated to give crude [2-(2,4-dichlorophenyl)-1-methylethyl]amine (yield; 0.8 g, 91%).

property; $^1$H-NMR [CDCl$_3$/TMS, δ value (ppm)] 7.38 (d, 1H), 7.18 (d, 1H), 7.17 (s, 1H), 3.24 (m, 1H), 2.80 (dd, 1H), 2.65 (dd, 1H), 1.23 (d, 3H)

1-3)

To a solution of crude [2-(2,4-dichlorophenyl)-1-methylethyl]amine (about 0.8 g, 3.9 mmol) and triethylamine (0.6 g, 5.9 mmol) in tetrahydrofuran (20 ml) was slowly added dropwise 2-trifluoromethylbenzoyl chloride (0.8 g, 3.8 mmol) at room temperature. After stirring at room temperature for 0.5 hr, water was added and the mixture was extracted with ethyl acetate. The organic layer was washed with 0.5N hydrochloric acid, saturated aqueous sodium hydrogen carbonate, and saturated brine, dried over anhydrous magnesium sulfate, and concentrated. The residue was purified by silica gel column chromatography and recrystallized from a mixed solvent of acetone/n-hexane to give a desired compound (white solid, yield; 0.4 g, 27%).

property; melting point 142° C.

Example 2

Production of N-[2-(2,4-dichlorophenyl)-1-methylethyl]-2-trifluoromethylpyrazine-3-carboxamide (compound No. 3-43)

To a solution of 2-trifluoromethylpyrazine-3-carboxylic acid (0.25 g, 1.3 mmol), [2-(2,4-dichlorophenyl)-1-methylethyl]amine (0.27 g, 1.3 mmol) and 4-dimethylaminopyridine (0.19 g, 1.6 mmol) in chloroform (10 ml) was added 1-ethyl-3-(3-dimethylaminopropyl)carbodiimide hydrochloride (0.3 g, 1.6 mmol) and the mixture was stirred at room temperature for 12 hrs. After adding water and chloroform, the mixture was partitioned, and the organic layer was washed successively with water and saturated brine and dried over anhydrous sodium sulfate. The mixture was concentrated under reduced pressure and the residue was purified by silica gel column chromatography (hexane:ethyl acetate=2:1) to give a desired compound (yield; 0.31 g, 63%).

property; melting point 163-164° C.

Example 3

Production of N-{1-[1-(2,4-dichlorophenyl)cyclopropyl]ethyl}-2-chloropyrazine-3-carboxamide (compound No. 3'-45)

3-1)

To a solution of 1-(2,4-dichlorophenyl)cyclopropanecarbonitrile (5.0 g, 23.6 mmol) in tetrahydrofuran (20 ml) was added methylmagnesium bromide (0.96 mol/l tetrahydrofuran solution; 30 ml) at room temperature. After heating under reflux for 1.5 hrs, the mixture was allowed to cool to room temperature, and 0.5M hydrochloric acid was added under cooling in an ice bath. The organic layer extracted with ethyl acetate was dried over anhydrous magnesium sulfate and concentrated to give crude 1-[1-(2,4-dichlorophenyl)cyclopropyl]ethanone (brown oil, yield; 3.4 g, 63%).

3-2)

A mixture of 1-[1-(2,4-dichlorophenyl)cyclopropyl]ethanone (3.4 g, 14.8 mmol), hydroxylamine hydrochloride (2.8 g), triethylamine (3.8 g) and ethanol (30 ml) was heated under reflux for 8 hrs. The mixture was allowed to cool to room temperature, ethanol was evaporated and ethyl acetate was added. After washing with water and saturated brine, the organic layer was dried over anhydrous magnesium sulfate, and concentrated. The residue was purified by silica gel column chromatography to give 1-[1-(2,4-dichlorophenyl)cyclopropyl]ethanoneoxime (white solid, yield; 3.4 g, 94%).

3-3)

A mixture of 1-[1-(2,4-dichlorophenyl)cyclopropyl]ethanoneoxime (2.6 g, 10.7 mmol), Raney-nickel (2.0 g) and ethanol (30 ml) was stirred under pressurization with hydrogen at room temperature for 30 hrs. Raney-nickel was removed by celite filtration, and the filtrate was concentrated. Ethyl acetate was added to the residue and the mixture was washed with water and saturated brine. The organic layer was dried over anhydrous magnesium sulfate and concentrated to give crude 1-[1-(2,4-dichlorophenyl)cyclopropyl]ethylamine (brown oil).

property; $^1$H-NMR [CDCl$_3$/TMS, δ value (ppm)] 7.37 (d, 1H), 7.29 (d, 1H), 7.18 (dd, 1H), 2.87 (q, 1H), 1.05 (d, 3H), 0.96 (br, 2H), 0.80 (d, 2H)

This was dissolved in methyl t-butyl ether (20 ml) and a solution of 4N hydrochloric acid in ethyl acetate was added dropwise thereto. A white precipitate was filtered, washed with methyl t-butyl ether and air dried to give 1-[1-(2,4-dichlorophenyl)cyclopropyl]ethylamine hydrochloride (white solid, yield; 2.0 g).

property; $^1$H-NMR [CDCl$_3$/TMS, δ value (ppm)] 8.35 (br, 3H), 7.45 (d, 1H), 7.39 (d, 1H), 7.19 (dd, 1H), 3.36 (br, 1H), 1.37 (d, 3H), 1.25-1.39 (m, 2H), 1.03 (m, 1H), 0.96 (m, 1H)

3-4)

To a solution of 2-chloropyrazine-3-carboxylic acid (0.15 g, 1.0 mmol), 1-[1-(2,4-dichlorophenyl)cyclopropyl]ethylamine hydrochloride (0.25 g, 0.94 mmol) and 4-dimethylaminopyridine (0.29 g, 2.4 mmol) in chloroform (10 ml) was added 1-ethyl-3-(3-dimethylaminopropyl)carbodiimide hydrochloride (0.22 g, 1.2 mmol) and the mixture was stirred at room temperature for 12 hrs. After adding water and chloroform, the mixture was separated, and the organic layer was washed successively with water and saturated brine and dried over anhydrous sodium sulfate. The mixture was concentrated under reduced pressure and the residue was purified by silica gel column chromatography (hexane:ethyl acetate=3:1) to give a desired compound (yield; 0.24 g, 69%).

property; $^1$H-NMR [CDCl$_3$/TMS, δ value (ppm)]: 8.53 (d, 1H), 8.47 (d, 1H), 7.55 (br, 1H), 7.37 (d, 1H), 7.32 (d, 1H), 7.19 (dd, 1H), 4.11 (m, 1H), 1.28 (m, 1H), 1.23 (d, 3H), 1.01 (m, 1H), 0.90 (m, 2H)

Typical formulation examples and experimental example of the present invention are described below but they should not be construed as limiting the scope of the invention.

As used in the examples, the terms "part" and "parts" means parts by weight.

Formulation Example 1

| | |
|---|---|
| compound of the present invention | 10 parts |
| Xylene | 70 parts |
| N-methylpyrrolidone | 10 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| | |
|---|---|
| compound of the present invention | 3 parts |
| Clay powder | 82 parts |
| Diatomaceous earth powder | 15 parts |

A dust was prepared by mixing uniformly and grinding the above ingredients.

Formulation Example 3

| | |
|---|---|
| compound of the present invention | 5 parts |
| Mixed powder of bentonite and clay | 90 parts |
| Calcium ligninsulfonate | 5 parts |

Granules were prepared by mixing the above ingredients uniformly, and kneading the resulting mixture together with a suitable amount of water, followed by granulation and drying.

Formulation Example 4

| | |
|---|---|
| compound of the present invention | 20 parts |
| Mixture of kaolin and synthetic high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

The following Experimental Examples show usefulness of the compound of the present invention as a pest controlling agent, particularly a plant disease controlling agent or nematocide. The compounds of the present invention are indicated with the compound numbers described in Table 1 to Table 11. As control compounds for comparison, the following four compounds were subjected to a similar evaluation.

comparison compound A; 2,6-dichloro-N-[2-{3-(trifluoromethyl)phenyl}ethyl]benzamide (compound No. 12 described in JP-A-1-151546)

comparison compound B; N-{2-[3-chloro-5-(trifluoromethyl)pyridin-2-yl]ethyl}-2-trifluoromethylbenzamide (compound No. A-20 described in WO04/016088)

comparison compound C; N-{2-[3-chloro-5-(trifluoromethyl)pyridin-2-yl]ethyl}-2-chloropyridine-3-carboxamide (compound No. R-1 described in WO04/074280)

comparison compound D; N-[3',4'-dichloro-(1,1-dimethyl)phenacyl]-3-methyl-2-thiophenecarboxamide (compound No. 1-20 described in WO06/016708)

Experimental Example 1

Test on the Controlling Efficacy Against Apple Tree Scab

A seedling of an apple tree (the variety: Ohrin) grown in a pot was subjected to foliar application with a diluted emulsion of the emulsifiable concentrate of the compound of the present invention prepared in accordance with Formulation Example 1, which diluted emulsion was produced by diluting the concentrate with water to the specifically determined volume. On the following day after the application, the seedling was inoculated by spraying with a spore suspension of the causal fungus of apple tree scab (*Venturia inaequalis*) as obtained by culture on the PSA medium and maintained at 20° C. under humid conditions.

Fourteen days after the inoculation, the protective value (%) was determined in accordance with the equation (1), and the controlling efficacy was assessed according the below-described criteria of judgment.

$$\text{Protective value (\%)} = \frac{\text{(Ratio of the lesion area in non-treated section)} - \text{(Ratio of the lesion in treated section)}}{\text{(Ratio of the lesion area in non-treated section)}} \times 100 \quad (1)$$

Criteria of Judgment:
  0: Less than 9% in protective value
  1: 10 to 19% in protective value
  2: 20 to 29% in protective value
  3: 30 to 39% in protective value
  4: 40 to 49% in protective value
  5: 50 to 59% in protective value
  6: 60 to 69% in protective value
  7: 70 to 79% in protective value
  8: 80 to 89% in protective value
  9: 90 to 99% in protective value
  10: 100% in protective value As a result of the above-mentioned experiment, the compound of the present invention exhibited a superior control effect at the active ingredient concentration of 50 ppm and the application emulsion amount of 50 mL and particularly, compound Nos. 1-16, 1-17, 1-20, 1-21, 1-22, 1-23, 1-28, 1-29, 1-30, 1-34, 1-37, 1-51, 1-65, 2-1, 2-53, 2-58, 3-4, 3-5, 3-6, 3-7, 3-8, 3-10, 3-11, 3-23, 3-30, 3-37, 3-43, 3-43-S, 3-50, 3-51, 3-53, 3-54, 3-58, 3-59, 3-60, 3-61, 3-62, 3-64, 3-65, 3-67, 3-75, 3-76, 3-77, 3-82, 3-86, 3-92, 3-94, 3-96, 3-100, 3-102, 3-103, 3-106, 3'-5,3'-6,3'-7,3'-11, 3'-30, 3'-44, 3'-61, 3'-62, 3"-5,3"-8,4-1, 5-4, 5-5, 5-7, 5-15, 5-20, 5-21, 5-26, 6-1, 6-2, 6-3, 6-5, 6-9, 6-22, 6-24, 6-26, 9-1 and 9-2 exhibited a high activity of 10 in the criteria of judgment. Comparison compound A showed no effect as evidenced by 0 in the criteria of judgment, even by a treatment at a 4-fold concentration as high as 200 ppm.

Experimental Example 2

Test on the Controlling Efficacy Against Gray Mold of Cucumber Plant

A one-leaf aged cucumber plant (cultivar: Suyou) raised as a seedling in a pot of 9 cm in diameter was subject to foliar application with a diluted emulsion of the emulsifiable concentrate of the compound of the present invention prepared in accordance with Formulation Example 1, which diluted emulsion was produced by diluting the concentrate with water to the specifically determined volume.

On the following day after the application, the cotyledon of the cucumber plant was inoculated by placing a paper disc of 6 mm in diameter soaked with a spore suspension of the causal fungus of gray mold of cucumber plant (*Botrytis*

*cinerea*) as obtained by culture on the PSA medium, and maintained at 20° C. under humid conditions.

Seven days after the inoculation, the protective value (%) was determined in accordance with the equation (2), and the controlling efficacy was assessed according the criteria of judgment as set forth in Experimental Example 1.

$$\text{Protective value (\%)} = \frac{\text{(Diameter of the lesion area in non-treated section)} - \text{(Diameter of the lesion in treated section)}}{\text{(Diameter of the lesion area in non-treated section)}} \times 100 \qquad (2)$$

As a result of the above-mentioned experiment, the compound of the present invention exhibited a superior control effect at the active ingredient concentration of 50 ppm and the application emulsion amount of 50 ml and particularly, compound Nos. 1-20, 2-1, 2-20, 2-25, 3-4, 3-5, 3-6, 3-7, 3-8, 3-9, 3-10, 3-11, 3-25, 3-30, 3-42, 3-43, 3-43-S, 3-51, 3-53, 3-61, 3-62, 3-64, 3-75, 3-77, 3-86, 3-89, 3-92, 3-93, 3-94, 3-96, 3-100, 3-102, 3-103, 3-104, 3-105, 3-106, 3'-5,3'-6,3'-7, 3'-11, 3'-30, 3'-42, 3'-43, 3'-44, 3"-5, 3"-8, 3"-42, 4-2, 5-21, 6-1, 6-3, 6-19, 6-22, 7-1 and 9-2 exhibited a high activity of 10 in the criteria of judgment. Comparison compound A, comparison compound B and comparison compound D showed no effect as evidenced by 0 in the criteria of judgment. Comparison compound A showed no effect as evidenced by 0 in the criteria of judgment, even by a treatment at a 4-fold concentration as high as 200 ppm.

Experimental Example 3

Test on the Controlling Efficacy Against Powdery Mildew of Barley Plant

A one-leaf aged barley plant (the cultivar: Kantoh No. 6) raised as a seedling in a pot of 6 cm in diameter was subjected to foliar application with a diluted emulsion of the emulsifiable concentrate of the compound of the present invention prepared in accordance with Formulation Example 1, which diluted emulsion was produced by diluting the concentrate with water to the specifically determined volume. On the following day after the application, the barley plant was inoculated by sprinkling with spores as obtained from the leaves of barley plants infected with the causal fungus of barley powdery mildew (*Blumeria graminis* f. sp. *hordei*), and maintained under glass house conditions. Seven days after the inoculation, the controlling efficacy was assessed according the criteria of judgment as set forth in Experimental Example 1.

As a result of the above-mentioned experiment, the compound of the present invention exhibited a superior control effect at the active ingredient concentration of 50 ppm and the application emulsion amount of 50 mL and particularly, compound Nos. 1-16, 1-25, 1-27, 1-29, 1-30, 1-32, 1-33, 1-34, 1-35, 1-37, 1-39, 1-51, 1-61, 1-63, 1-79, 2-18, 2-25, 2-26, 2-58, 3-4, 3-5, 3-7, 3-9, 3-10, 3-11, 3-25, 3-37, 3-42, 3-43, 3-43-S, 3-44, 3-50, 3-51, 3-53, 3-58, 3-60, 3-61, 3-62, 3-64, 3-75, 3-77, 3-86, 3-92, 3-93, 3-94, 3-96, 3-100, 3-102, 3-103, 3-104, 3'-5,3'-7,3'-11, 3'-42, 3'-43, 3'-45, 3'-61, 3'-65, 3"-42, 5-4, 5-6, 5-7, 5-15, 5-20, 5-21, 5-23, 6-1, 6-4, 6-11, 6-12, 6-13, 6-14, 6-15, 6-18, 6-20, 6-22, 6-23, 6-26 and 9-1 exhibited a high activity of 10 in the criteria of judgment. Comparison compound A, comparison compound B, comparison compound C and comparison compound D showed no effect as evidenced by 0 in the criteria of judgment.

Experimental Example 4

Test on the Controlling Efficacy Against Southern Root-Knot Nematode (*Meloidogyne incognita*)

An emulsion prepared by diluting an emulsifiable concentrate of the compound of the present invention, which was prepared in accordance with Formulation Example 1, to 500 ppm was irrigated to the plant foot of a pot-cultivated nursery plant raised from the seed of melon. One day after the irrigation, an aqueous suspension (about 500 nematodes/ml) of southern root-knot nematode was inoculated (soil irrigation) to a treated section and a non-treated section, and the pot was placed in a greenhouse at 25° C. Eight days after the inoculation, the root was washed with water, the number of root knots was counted, and the effect was assessed according to the following criteria of judgment.

Criteria of Judgment

A: No root knot.

B: Apparently smaller number of root knots than in non-treated section were present.

C: Root knots in the number equivalent to or higher than in non-treated section were present.

As a result of the above-mentioned experiment, the compound of the present invention exhibited a superior control effect at the active ingredient concentration of 500 ppm by the plant foot irrigation treatment, and compound Nos. 1-16, 1-34, 3'-43, 3'-44 and 3"-48 exhibited a high activity of not less than B in the criteria of judgment.

INDUSTRIAL APPLICABILITY

The compound of the present invention is useful as a pest controlling agent showing a low geoenvironmental impact, a broad control spectrum at a low dose, and a superior control efficacy.

This application is based on patent application Nos. 077752/2006 and 294810/2006 filed in Japan, the contents of which are hereby incorporated by reference.

While this invention has been shown and described with references to preferred embodiments thereof, it will be understood by those skilled in the art that various changes in form and details may be made therein without departing from the scope of the invention encompassed by the appended claims. All patents, patent publications and other publications identified or referenced herein are incorporated by reference in their entirety.

The invention claimed is:

1. A N-2-(hetero)arylethylcarboxamide compound represented by formula (I)

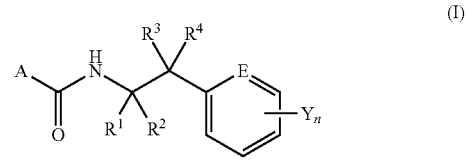

wherein $R^1$ and $R^2$ are each independently
a hydrogen atom; or
a $(C_1-C_3)$alkyl group,
or
$R^1$ and $R^2$ are optionally bonded to each other to form
a $(C_3-C_6)$cycloalkane,
$R^3$ and $R^4$ are each independently
a hydrogen atom;
a halogen atom; or
a $(C_1-C_6)$alkyl group, or
$R^3$ and $R^4$ are optionally bonded to each other to form
a $(C_3-C_6)$cycloalkane,
$R^3$ and $R^4$ optionally form an oxygen atom in combination,
each Y is independently
a halogen atom;
a cyano group;
a hydroxy group;
a $(C_1-C_6)$alkyl group optionally substituted by halogen atom(s);
a $(C_2-C_6)$alkenyl group optionally substituted by halogen atom(s);
a $(C_2-C_6)$alkynyl group optionally substituted by halogen atom(s);
a $(C_1-C_6)$alkoxy group optionally substituted by substituent(s) selected from the group consisting of a halogen atom and a $(C_1-C_6)$alkoxy group;
a $(C_2-C_6)$alkenyloxy group optionally substituted by halogen atom(s);
a $(C_2-C_6)$alkynyloxy group optionally substituted by halogen atom(s);
a $(C_1-C_6)$alkylthio group optionally substituted by halogen atom(s);
a $(C_1-C_6)$alkylsulfinyl group optionally substituted by halogen atom(s);
a $(C_1-C_6)$alkylsulfonyl group optionally substituted by halogen atom(s);
a $(C_1-C_6)$alkoxy-carbonyl group;
a $(C_1-C_6)$alkoxyimino$(C_1-C_3)$alkyl group;
a $(C_3-C_{30})$trialkylsilyl group;
a phenyl group optionally substituted by one or more substituents selected from substituent group Z;
a phenoxy group optionally substituted by one or more substituents selected from substituent group Z; or
heterocyclyloxy group optionally substituted by one or more substituents selected from substituent group Z,
n is an integer of 1 to 5,
two Y's that become adjacent when n is an integer of 2 to 5 are optionally bonded to each other to represent
a $(C_3-C_5)$alkylene group;
a $(C_3-C_5)$alkenylene group;
a $(C_2-C_4)$alkyleneoxy group; or
a $(C_1-C_3)$alkylenedioxy group optionally substituted by halogen atom(s),
substituent group Z is
a hydrogen atom;
a halogen atom;
a cyano group;
a $(C_1-C_6)$alkyl group optionally substituted by halogen atom(s);
a $(C_2-C_6)$alkenyl group optionally substituted by halogen atom(s);
a $(C_2-C_6)$alkynyl group optionally substituted by halogen atom(s);
a $(C_1-C_6)$alkoxy group optionally substituted by halogen atom(s);
a $(C_2-C_6)$alkenyloxy group optionally substituted by halogen atom(s);
a $(C_2-C_6)$alkynyloxy group optionally substituted by halogen atom(s);
a $(C_1-C_6)$alkylthio group optionally substituted by halogen atom(s);
a $(C_1-C_6)$alkylsulfinyl group optionally substituted by halogen atom(s);
a $(C_1-C_6)$alkylsulfonyl group optionally substituted by halogen atom(s);
a $(C_1-C_6)$alkoxy-carbonyl group;
a $(C_1-C_6)$alkoxyimino$(C_1-C_3)$alkyl group; or
a carbamoyl group,
A is a substituted cyclic group represented by the formula (A3),

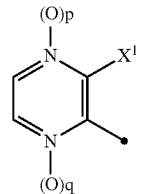

(A3)

wherein $X^1$ is
a halogen atom; or
a $(C_1-C_3)$alkyl group optionally substituted by halogen atom(s);
p and q are each 0, and
E is
C—H;
C—Y (Y is as defined above); or
a nitrogen atom,
or a salt thereof.

2. The N-2-(hetero)arylethylcarboxamide compound of claim 1, wherein
E is
C—H;
C—Y (Y is as defined below) or
a nitrogen atom,
$R^1$ and $R^2$ are each independently
a hydrogen atom; or
a $(C_1-C_3)$alkyl group, or
$R^1$ and $R^2$ are optionally bonded to each other to form
a $(C_3-C_6)$cycloalkane,
$R^3$ and $R^4$ are each independently
a hydrogen atom;
a halogen atom; or
a $(C_1-C_6)$alkyl group,
$R^3$ and $R^4$ are optionally bonded to each other to form
a $(C_3-C_6)$cycloalkane, or
$R^3$ and $R^4$ optionally form an oxygen atom in combination,
each Y is independently
a halogen atom;
a cyano group;
a hydroxy group;
a $(C_1-C_6)$alkyl group optionally substituted by halogen atom(s);
a $(C_1-C_6)$alkoxy group optionally substituted by halogen atom(s);
a $(C_2-C_6)$alkenyloxy group optionally substituted by halogen atom(s);
a $(C_1-C_6)$alkylthio group optionally substituted by halogen atom(s);
a $(C_1-C_6)$alkylsulfinyl group optionally substituted by halogen atom(s);

a $(C_1-C_6)$alkylsulfonyl group optionally substituted by halogen atom(s);

a phenyl group optionally substituted by the same or different one or more substituents selected from the group consisting of
(i) a halogen atom,
(ii) a $(C_1-C_6)$alkyl group optionally substituted by halogen atom(s) and
(iii) a $(C_1-C_6)$alkoxy group optionally substituted by halogen atom(s);

a phenoxy group optionally substituted by the same or different one or more substituents selected from the group consisting of
(i) a halogen atom,
(ii) a $(C_1-C_6)$alkyl group optionally substituted by halogen atom(s) and
(iii) a $(C_1-C_6)$alkoxy group optionally substituted by halogen atom(s); or a heterocyclyloxy group optionally substituted by the same or different one or more substituents selected from the group consisting of
(i) a halogen atom,
(ii) a $(C_1-C_6)$alkyl group optionally substituted by halogen atom(s) and
(iii) a $(C_1-C_6)$alkoxy group optionally substituted by halogen atom(s), n is an integer of 1 to 3, two Y's that become adjacent when n is an integer of 2 or 3 are optionally bonded to each other to show a $(C_3-C_5)$alkylene group;
a $(C_3-C_5)$alkenylene group;
a $(C_2-C_4)$alkyleneoxy group; or
a $(C_1-C_3)$alkylenedioxy group optionally substituted by halogen atom(s), $X^1$ is a halogen atom; or
a $(C_1-C_3)$alkyl group optionally substituted by halogen atom(s), and p and q are each 0, or a salt thereof.

3. The N-2-(hetero)arylethylcarboxamide compound of claim 2, wherein

E is C—H or C—Y (Y is as defined in claim 2), or a salt thereof.

4. A pest controlling agent comprising the N-2-(hetero)arylethylcarboxamide compound of claim 1, or a salt thereof as an active ingredient.

5. The pest controlling agent of claim 4, which is a plant disease controlling agent.

6. The pest controlling agent of claim 4, which is a nematocide.

7. A method of controlling pests, which comprises treating an objective crop plant or the soil used for cultivation of the plant with an effective amount of the pest controlling agent of claim 4.

* * * * *